(12) United States Patent
Wiegand et al.

(10) Patent No.: US 7,303,746 B2
(45) Date of Patent: Dec. 4, 2007

(54) METHODS OF TREATING EYE DISORDERS WITH MODIFIED CHIMERIC POLYPEPTIDES

(75) Inventors: Stanley J. Wiegand, Croton on Hudson, NY (US); Nicholas Papadopoulos, LaGrangeville, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 425 days.

(21) Appl. No.: 10/988,243

(22) Filed: Nov. 12, 2004

(65) Prior Publication Data

US 2005/0175610 A1   Aug. 11, 2005

Related U.S. Application Data

(63) Continuation-in-part of application No. 10/009,852, filed as application No. PCT/US00/14142 on May 23, 2000, now Pat. No. 7,070,959.

(60) Provisional application No. 60/138,133, filed on Jun. 8, 1999.

(51) Int. Cl.
*A61K 38/18* (2006.01)
*C07K 14/71* (2006.01)
*C12N 15/62* (2006.01)

(52) U.S. Cl. ............... 424/134.1; 424/192.1; 514/2; 514/12; 530/350; 530/387.3; 536/23.4

(58) Field of Classification Search .......... None
See application file for complete search history.

(56) References Cited

U.S. PATENT DOCUMENTS 5,712,380 A   1/1998   Kendall et al.
6,011,003 A   1/2000   Charnock-Jones et al.
2005/0260203 A1*  11/2005  Wiegand et al. .......... 424/145.1
2006/0030529 A1*   2/2006  Wiegand et al. .............. 514/12
2006/0172944 A1*   8/2006  Wiegand et al. .............. 514/12

FOREIGN PATENT DOCUMENTS

WO   WO97/44453   11/1997
WO   WO98/13071    4/1998
WO   WO99/03996    1/1999

OTHER PUBLICATIONS

Witmer et al. (2003). Vascular endothelial growth factors and angiogenesis in eye disease. Prog. Retin. Eye Res. 22:1-29.*
Terman, B. I., et al, "Identification of a new endothelial cell growth factor receptor tyrosine kinase", Oncogene (1991) 6:1677-1683.
Terman, B.I., et al, "Identification of the KDR tyrosine kinase as a receptor for vascular endothelial cell growth factor", Biochem Biophys Res Comm (1992) 187(3):1579-1586.
Davis-Smyth, T., et al., 1996, "The second immunoglobulin-like domain of the VEGF tyrosine kinase receptor Flt-1 determines ligand binding and may initiate a signal transduction cascade", The EMBO Journal 15(18):4919-4927.
Holash, J., et al., (2002) PNAS 99(17):11393-11398.
Heidaran, M.A., et al., (1990) J. Bio. Chem. 265(31):18741-18744.
Cunningham, S.A., et al., (1997) Biochem. Biophys. Res. Comm. 231:596-599.
Fuh, G., et al., (1998) J. Bio. Chem. 273(18):11197-11204.
Wiesmann, C., et al., (1997) Cell 91:695-704.
Barleon, B., et al., (1997) J. Bio. Chem. 272(16):10382-10388.
Davis-Smyth, T., et al., (1998) J. Bio. Chem. 273(6):3216-3222.

* cited by examiner

*Primary Examiner*—Christine J. Saoud
*Assistant Examiner*—Jon M. Lockard
(74) *Attorney, Agent, or Firm*—Valeta Gregg, Esq.

(57) ABSTRACT

Modified chimeric polypeptides with improved pharmacokinetics are disclosed useful for treating eye disorders, including age-related macular degeneration and diabetic retinopathy.

5 Claims, 21 Drawing Sheets

| Binding Stoichiometry of hVEGF165 to Flt1D2Flk1D3.FcΔC1(a) & VEGFR1R2-FcΔC1(a) | | |
|---|---|---|
| hVEGF165 (nM) | VEGF/Flt1D2Flk1D3.FcΔC1(a) | VEGF/VEGFR1R2-FcΔC1(a) |
| 1 | 0.93 | 0.98 |
| 10 | 0.97 | 0.94 |
| 50 | 1 | 0.99 |
| Average ± StDev | 0.96 ± 0.03 | 0.97 ± 0.02 |

Fig. 7

SEQUENCE LISTING

<160> NUMBER OF SEQ ID NOS: 35

<210> SEQ ID NO 1
<211> LENGTH: 1704
<212> TYPE: DNA
<213> ORGANISM: Homo sapiens

<400> SEQUENCE: 1

```
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca ggggggaagc agcccataaa     180
tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ctttcgtaga gatgtacagt     420
gaaatccccg aaattataca catgactgaa ggaagggagc tcgtcattcc ctgccggtt      480 acgtcaccta acatcactgt tactttaaaa aagtttccac ttgacacttt gatccctgat     540
ggaaaacgca taatctggga cagtagaaag ggcttcatca tatcaaatgc aacgtacaaa     600
gaaatagggc ttctgacctg tgaagcaaca gtcaatgggc atttgtataa gacaaactat     660
ctcacacatc gacaaaccaa tacaatcata gatgtccaaa taagcacacc acgcccagtc     720
aaattactta gaggccatac tcttgtcctc aattgtactg ctaccactcc cttgaacacg     780
agagttcaaa tgacctggag ttaccctgat gaaaaaaata agagagcttc cgtaaggcga     840
cgaattgacc aaagcaattc ccatgccaac atattctaca gtgttcttac tattgacaaa     900
atgcagaaca agacaaagg actttatact tgtcgtgtaa ggagtggacc atcattcaaa     960
```

-continued

```
tctgttaaca cctcagtgca tatatatgat aaagcaggcc cgggcgagcc caaatcttgt   1020
gacaaaactc acacatgccc accgtgccca gcacctgaac tcctgggggg accgtcagtc   1080
ttcctcttcc ccccaaaacc caaggacacc ctcatgatct cccggacccc tgaggtcaca   1140
tgcgtggtgg tggacgtgag ccacgaagac cctgaggtca agttcaactg gtacgtggac   1200
ggcgtggagg tgcataatgc caagacaaag ccgcgggagg agcagtacaa cagcacgtac   1260
cgtgtggtca gcgtcctcac cgtcctgcac caggactggc tgaatggcaa ggagtacaag   1320
tgcaaggtct ccaacaaagc cctcccagcc cccatcgaga aaaccatctc caaagccaaa   1380
gggcagcccc gagaaccaca ggtgtacacc ctgcccccat cccgggatga gctgaccaag   1440
aaccaggtca gcctgacctg cctggtcaaa ggcttctatc ccagcgacat cgccgtggag   1500
tgggagagca atgggcagcc ggagaacaac tacaagacca cgcctcccgt gctggactcc   1560
gacggctcct tcttcctcta cagcaagctc accgtggaca agagcaggtg gcagcagggg   1620
aacgtcttct catgctccgt gatgcatgag gctctgcaca accactacac gcagaagagc   1680 ctctcccctgt ctccgggtaa atga                                        1704
```

<210> SEQ ID NO 2
<211> LENGTH: 567
<212> TYPE: PRT
<213> ORGANISM: Homo sapienss

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240
```

```
Lys Leu Leu Arg Gly His Thr Leu Val Leu Asn Cys Thr Ala Thr Thr
            245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
    290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Gly Pro Gly Glu
            325                 330                 335
Pro Lys Ser Cys Asp Lys Thr His Thr Cys Pro Pro Cys Pro Ala Pro
            340                 345                 350
Glu Leu Leu Gly Gly Pro Ser Val Phe Leu Phe Pro Pro Lys Pro Lys
            355                 360                 365
Asp Thr Leu Met Ile Ser Arg Thr Pro Glu Val Thr Cys Val Val Val
370                 375                 380
Asp Val Ser His Glu Asp Pro Glu Val Lys Phe Asn Trp Tyr Val Asp
385                 390                 395                 400
Gly Val Glu Val His Asn Ala Lys Thr Lys Pro Arg Glu Glu Gln Tyr
                405                 410                 415
Asn Ser Thr Tyr Arg Val Val Ser Val Leu Thr Val Leu His Gln Asp
            420                 425                 430
Trp Leu Asn Gly Lys Glu Tyr Lys Cys Lys Val Ser Asn Lys Ala Leu
        435                 440                 445
Pro Ala Pro Ile Glu Lys Thr Ile Ser Lys Ala Lys Gly Gln Pro Arg
    450                 455                 460
Glu Pro Gln Val Tyr Thr Leu Pro Pro Ser Arg Asp Glu Leu Thr Lys
465                 470                 475                 480
Asn Gln Val Ser Leu Thr Cys Leu Val Lys Gly Phe Tyr Pro Ser Asp
            485                 490                 495
Ile Ala Val Glu Trp Glu Ser Asn Gly Gln Pro Glu Asn Asn Tyr Lys
            500                 505                 510
Thr Thr Pro Pro Val Leu Asp Ser Asp Gly Ser Phe Phe Leu Tyr Ser
            515                 520                 525
Lys Leu Thr Val Asp Lys Ser Arg Trp Gln Gln Gly Asn Val Phe Ser
        530                 535                 540
Cys Ser Val Met His Glu Ala Leu His Asn His Tyr Thr Gln Lys Ser
545                 550                 555                 560
Leu Ser Leu Ser Pro Gly Lys
                565

<210> SEQ ID NO 3
<211> LENGTH: 1674
<212> TYPE: DNA
<213> ORGANISM: Homo sapiens

<400> SEQUENCE: 3
atggtcagct actgggacac cggggtcctg ctgtgcgcgc tgctcagctg tctgcttctc    60
acaggatcta gttcaggttc aaaattaaaa gatcctgaac tgagtttaaa aggcacccag   120
cacatcatgc aagcaggcca gacactgcat ctccaatgca gggggaagc agcccataaa   180 tggtctttgc ctgaaatggt gagtaaggaa agcgaaaggc tgagcataac taatctgcc   240
```

-continued

```
tgtggaagaa atggcaaaca attctgcagt actttaacct tgaacacagc tcaagcaaac      300
cacactggct tctacagctg caaatatcta gctgtaccta cttcaaagaa gaaggaaaca      360
gaatctgcaa tctatatatt tattagtgat acaggtagac ctttcgtaga gatgtacagt      420
gaaatccccg aaattataca catgactgaa ggaagggagc tcgtcattcc ctgccgggtt      480
acgtcaccta acatcactgt tactttaaaa agtttccac ttgacacttt gatccctgat       540
ggaaaacgca taatctggga cagtagaaag ggcttcatca tatcaaatgc aacgtacaaa      600
gaaatagggc ttctgacctg tgaagcaaca gtcaatgggc atttgtataa gacaaactat      660
ctcacacatc gacaaaccaa tacaatcata gatgtccaaa taagcacacc acgcccagtc      720
aaattactta gaggccatac tcttgtcctc aattgtactg ctaccactcc cttgaacacg      780
agagttcaaa tgacctggag ttaccctgat gaaattgacc aaagcaattc ccatgccaac      840
atattctaca gtgttcttac tattgacaaa atgcagaaca aagacaaagg actttatact      900
tgtcgtgtaa ggagtggacc atcattcaaa tctgttaaca cctcagtgca tatatatgat      960
aaagcaggcc cggcgagcc caaatcttgt gacaaaactc acacatgccc accgtgccca     1020
gcacctgaac tcctgggggg accgtcagtc ttcctcttcc ccccaaaacc caaggacacc     1080
ctcatgatct cccggacccc tgaggtcaca tgcgtggtgg tggacgtgag ccacgaagac     1140
cctgaggtca agttcaactg gtacgtggac ggcgtggagg tgcataatgc caagacaaag     1200
ccgcgggagg agcagtacaa cagcacgtac cgtgtggtca gcgtcctcac cgtcctgcac     1260
caggactggc tgaatggcaa ggagtacaag tgcaaggtct ccaacaaagc cctcccagcc     1320
cccatcgaga aaaccatctc caaagccaaa gggcagcccc gagaaccaca ggtgtacacc     1380
ctgcccccat cccgggatga gctgaccaag aaccaggtca gcctgacctg cctggtcaaa     1440
ggcttctatc ccagcgacat cgccgtggag tgggagagca atgggcagcc ggagaacaac     1500
tacaagacca cgcctcccgt gctggactcc gacggctcct tcttcctcta cagcaagctc     1560
accgtggaca gagcaggtg gcagcagggg aacgtcttct catgctccgt gatgcatgag     1620
gctctgcaca accactacac gcagaagagc ctctccctgt ctccgggtaa atga          1674
```

<210> SEQ ID NO 4
<211> LENGTH: 557
<212> TYPE: PRT
<213> ORGANISM: Homo sapiens

<400> SEQUENCE: 4

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
```

```
                115                 120                 125
Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Ile
            260                 265                 270

Asp Gln Ser Asn Ser His Ala Asn Ile Phe Tyr Ser Val Leu Thr Ile
        275                 280                 285

Asp Lys Met Gln Asn Lys Asp Lys Gly Leu Tyr Thr Cys Arg Val Arg
    290                 295                 300

Ser Gly Pro Ser Phe Lys Ser Val Asn Thr Ser Val His Ile Tyr Asp
305                 310                 315                 320

Lys Ala Gly Pro Gly Glu Pro Lys Ser Cys Asp Lys Thr His Thr Cys
                325                 330                 335

Pro Pro Cys Pro Ala Pro Glu Leu Leu Gly Gly Pro Ser Val Phe Leu
            340                 345                 350

Phe Pro Pro Lys Pro Lys Asp Thr Leu Met Ile Ser Arg Thr Pro Glu
        355                 360                 365

Val Thr Cys Val Val Val Asp Val Ser His Glu Asp Pro Glu Val Lys
    370                 375                 380

Phe Asn Trp Tyr Val Asp Gly Val Glu Val His Asn Ala Lys Thr Lys
385                 390                 395                 400

Pro Arg Glu Glu Gln Tyr Asn Ser Thr Tyr Arg Val Val Ser Val Leu
                405                 410                 415

Thr Val Leu His Gln Asp Trp Leu Asn Gly Lys Glu Tyr Lys Cys Lys
            420                 425                 430

Val Ser Asn Lys Ala Leu Pro Ala Pro Ile Glu Lys Thr Ile Ser Lys
        435                 440                 445

Ala Lys Gly Gln Pro Arg Glu Pro Gln Val Tyr Thr Leu Pro Pro Ser
    450                 455                 460

Arg Asp Glu Leu Thr Lys Asn Gln Val Ser Leu Thr Cys Leu Val Lys
465                 470                 475                 480

Gly Phe Tyr Pro Ser Asp Ile Ala Val Glu Trp Glu Ser Asn Gly Gln
                485                 490                 495

Pro Glu Asn Asn Tyr Lys Thr Thr Pro Pro Val Leu Asp Ser Asp Gly
            500                 505                 510

Ser Phe Phe Leu Tyr Ser Lys Leu Thr Val Asp Lys Ser Arg Trp Gln
        515                 520                 525

Gln Gly Asn Val Phe Ser Cys Ser Val Met His Glu Ala Leu His Asn
    530                 535                 540
```

His Tyr Thr Gln Lys Ser Leu Ser Leu Ser Pro Gly Lys
545                 550                 555

<210> SEQ ID NO 5
<211> LENGTH: 1359
<212> TYPE: DNA
<213> ORGANISM: Homo sapiens

<400> SEQUENCE: 5

```
atggtcagct actgggacac cggggtcctg ctgtgcgcgc tgctcagctg tctgcttctc    60
acaggatcta gttccggagg tagacctttc gtagagatgt acagtgaaat ccccgaaatt   120
atacacatga ctgaaggaag ggagctcgtc attccctgcc gggttacgtc acctaacatc   180
actgttactt taaaaaagtt tccacttgac actttgatcc ctgatggaaa acgcataatc   240
tgggacagta gaaagggctt catcatatca atgcaacgt acaaagaaat agggcttctg    300
acctgtgaag caacagtcaa tgggcatttg tataagacaa actatctcac acatcgacaa   360
accaatacaa tcatagatgt ccaaataagc acaccacgcc cagtcaaatt acttagaggc   420
catactcttg tcctcaattg tactgctacc actcccttga acacgagagt tcaaatgacc   480
tggagttacc ctgatgaaat tgaccaaagc aattcccatg ccaacatatt ctacagtgtt   540
cttactattg acaaaatgca gaacaaagac aaaggacttt atacttgtcg tgtaaggagt   600
ggaccatcat tcaaatctgt aacacctca gtgcatatat atgataaagc aggcccgggc   660
gagcccaaat cttgtgacaa aactcacaca tgcccaccgt gcccagcacc tgaactcctg   720
gggggaccgt cagtcttcct cttccccca aacccaagg acaccctcat gatctcccgg    780
acccctgagg tcacatgcgt ggtggtggac gtgagccacg aagaccctga ggtcaagttc   840
aactggtacg tggacggcgt ggaggtgcat aatgccaaga caaagccgcg ggaggagcag   900
tacaacagca cgtaccgtgt ggtcagcgtc ctcaccgtcc tgcaccagga ctggctgaat   960
ggcaaggagt acaagtgcaa ggtctccaac aaagccctcc cagcccccat cgagaaaacc  1020
atctccaaag ccaagggca gccccgagaa ccacaggtgt acaccctgcc cccatcccgg   1080
gatgagctga ccaagaacca ggtcagcctg acctgcctgg tcaaaggctt ctatcccagc  1140
gacatcgccg tggagtggga gagcaatggg cagccggaga caactacaa gaccacgcct   1200
cccgtgctgg actccgacgg ctccttcttc ctctacagca agctcaccgt ggacaagagc  1260
aggtggcagc aggggaacgt cttctcatgc tccgtgatgc atgaggctct gcacaaccac  1320
tacacgcaga agagcctctc cctgtctccg ggtaaatga                          1359
```

<210> SEQ ID NO 6
<211> LENGTH: 452
<212> TYPE: PRT
<213> ORGANISM: Homo sapiens

<400> SEQUENCE: 6

Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
                20                  25                  30

Met Tyr Ser Glu Ile Pro Glu Ile Ile His Met Thr Glu Gly Arg Glu
            35                  40                  45

Leu Val Ile Pro Cys Arg Val Thr Ser Pro Asn Ile Thr Val Thr Leu
        50                  55                  60

Lys Lys Phe Pro Leu Asp Thr Leu Ile Pro Asp Gly Lys Arg Ile Ile

```
             65                  70                  75                  80
Trp Asp Ser Arg Lys Gly Phe Ile Ile Ser Asn Ala Thr Tyr Lys Glu
                     85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Gln
            115                 120                 125

Ile Ser Thr Pro Arg Pro Val Lys Leu Leu Arg Gly His Thr Leu Val
    130                 135                 140

Leu Asn Cys Thr Ala Thr Thr Pro Leu Asn Thr Arg Val Gln Met Thr
145                 150                 155                 160

Trp Ser Tyr Pro Asp Glu Ile Asp Gln Ser Asn Ser His Ala Asn Ile
                165                 170                 175

Phe Tyr Ser Val Leu Thr Ile Asp Lys Met Gln Asn Lys Asp Lys Gly
            180                 185                 190

Leu Tyr Thr Cys Arg Val Arg Ser Gly Pro Ser Phe Lys Ser Val Asn
            195                 200                 205

Thr Ser Val His Ile Tyr Asp Lys Ala Gly Pro Gly Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 7
<211> LENGTH: 1389
<212> TYPE: DNA
<213> ORGANISM: Homo sapiens
```

<400> SEQUENCE: 7

```
atggtcagct actgggacac cggggtcctg ctgtgcgcgc tgctcagctg tctgcttctc        60
acaggatcta gttccggagg tagacctttc gtagagatgt acagtgaaat ccccgaaatt       120
atacacatga ctgaaggaag ggagctcgtc attccctgcc gggttacgtc acctaacatc       180
actgttactt taaaaaagtt tccacttgac actttgatcc ctgatggaaa acgcataatc       240
tgggacagta gaaagggctt catcatatca aatgcaacgt acaaagaaat agggcttctg       300
acctgtgaag caacagtcaa tgggcatttg tataagacaa actatctcac acatcgacaa       360
accaatacaa tcatagatgt ccaaataagc acaccacgcc cagtcaaatt acttagaggc       420
catactcttg tcctcaattg tactgctacc actcccttga acacgagagt tcaaatgacc       480
tggagttacc ctgatgaaaa aaataagaga gcttccgtaa ggcgacgaat tgaccaaagc       540
aattcccatg ccaacatatt ctacagtgtt cttactattg acaaaatgca gaacaaagac       600
aaaggacttt atacttgtcg tgtaaggagt ggaccatcat tcaaatctgt taacacctca       660
gtgcatatat atgataaagc aggcccgggc gagcccaaat cttgtgacaa aactcacaca       720
tgcccaccgt gcccagcacc tgaactcctg gggggaccgt cagtcttcct cttccccca       780
aaacccaagg acaccctcat gatctcccgg acccctgagg tcacatgcgt ggtggtggac       840
gtgagccacg aagaccctga ggtcaagttc aactggtacg tggacggcgt ggaggtgcat       900
aatgccaaga caaagccgcg ggaggagcag tacaacagca cgtaccgtgt ggtcagcgtc       960
ctcaccgtcc tgcaccagga ctggctgaat ggcaaggagt acaagtgcaa ggtctccaac      1020
aaagccctcc cagcccccat cgagaaaacc atctccaaag ccaaagggca gccccgagaa      1080
ccacaggtgt acaccctgcc cccatcccgg gatgagctga ccaagaacca ggtcagcctg      1140
acctgcctgg tcaaaggctt ctatcccagc gacatcgccg tggagtggga gagcaatggg      1200
cagccggaga acaactacaa gaccacgcct cccgtgctgg actccgacgg ctccttcttc      1260
ctctacagca agctcaccgt ggacaagagc aggtggcagc aggggaacgt cttctcatgc      1320
tccgtgatgc atgaggctct gcacaaccac tacacgcaga agagcctctc cctgtctccg      1380
ggtaaatga                                                             1389
```

<210> SEQ ID NO 8
<211> LENGTH: 462
<212> TYPE: PRT
<213> ORGANISM: Homo sapiens

<400> SEQUENCE: 8

```
Met Val Ser Tyr Trp Asp Thr Gly Val Leu Leu Cys Ala Leu Leu Ser
  1               5                  10                  15

Cys Leu Leu Leu Thr Gly Ser Ser Gly Gly Arg Pro Phe Val Glu
                 20                  25                  30

Met Tyr Ser Glu Ile Pro Glu Ile His Met Thr Glu Gly Arg Glu
             35                  40                  45

Leu Val Ile Pro Cys Arg Val Thr Ser Pro Asn Ile Thr Val Thr Leu
 50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
                100                 105                 110
```

-continued

```
Thr Asn Tyr Leu Thr His Arg Gln Thr Asn Thr Ile Ile Asp Val Gln
            115                 120                 125
Ile Ser Thr Pro Arg Pro Val Lys Leu Leu Arg Gly His Thr Leu Val
        130                 135                 140
Leu Asn Cys Thr Ala Thr Thr Pro Leu Asn Thr Arg Val Gln Met Thr
145                 150                 155                 160
Trp Ser Tyr Pro Asp Glu Lys Asn Lys Arg Ala Ser Val Arg Arg Arg
                165                 170                 175
Ile Asp Gln Ser Asn Ser His Ala Asn Ile Phe Tyr Ser Val Leu Thr
            180                 185                 190
Ile Asp Lys Met Gln Asn Lys Asp Lys Gly Leu Tyr Thr Cys Arg Val
        195                 200                 205
Arg Ser Gly Pro Ser Phe Lys Ser Val Asn Thr Ser Val His Ile Tyr
    210                 215                 220
Asp Lys Ala Gly Pro Gly Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
            325                 330                 335
Lys Val Ser Asn Lys Ala Leu Pro Ala Pro Ile Glu Lys Thr Ile Ser
        340                 345                 350
Lys Ala Lys Gly Gln Pro Arg Glu Pro Gln Val Tyr Thr Leu Pro Pro
    355                 360                 365
Ser Arg Asp Glu Leu Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
    450                 455                 460

<210> SEQ ID NO 9
<211> LENGTH: 1704
<212> TYPE: DNA
<213> ORGANISM: Homo sapiens

<400> SEQUENCE: 9
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
```

```
cacatcatgc aagcaggcca gacactgcat ctccaatgca ggggggaagc agcccataaa    180
tggtctttgc ctgaaatggt gagtaaggaa agcgaaaggc tgagcataac taaatctgcc    240
tgtggaagaa atggcaaaca attctgcagt actttaacct tgaacacagc tcaagcaaac    300
cacactggct tctacagctg caaatatcta gctgtaccta cttcaaagaa gaaggaaaca    360
gaatctgcaa tctatatatt tattagtgat acaggtagac ctttcgtaga gatgtacagt    420
gaaatccccg aaattataca catgactgaa ggaagggagc tcgtcattcc ctgccgggtt    480
acgtcaccta acatcactgt tactttaaaa agtttccac ttgacacttt gatccctgat    540
ggaaaacgca taatctggga cagtagaaag ggcttcatca tcaaatgc aacgtacaaa    600 gaaatagggc ttctgacctg tgaagcaaca gtcaatgggc atttgtataa gacaaactat    660
ctcacacatc gacaaaccaa tacaatcata gatgtccaaa taagcacacc acgcccagtc    720
aaattactta gaggccatac tcttgtcctc aattgtactg ctaccactcc cttgaacacg    780
agagttcaaa tgacctggag ttaccctgat gaaaaaaata gaacgcttc cgtaaggcga    840 cgaattgacc aaagcaattc ccatgccaac atattctaca gtgttcttac tattgacaaa    900
atgcagaaca aagacaaagg actttatact tgtcgtgtaa ggagtggacc atcattcaaa    960
tctgttaaca cctcagtgca tatatatgat aaagcaggcc cggcgagcc caaatcttgt    1020 gacaaaactc acacatgccc accgtgccca gcacctgaac tcctggggg accgtcagtc    1080 ttcctcttcc ccccaaaacc caaggacacc ctcatgatct cccggacccc tgaggtcaca    1140
tgcgtggtgg tggacgtgag ccacgaagac cctgaggtca agttcaactg gtacgtggac    1200
ggcgtggagg tgcataatgc caagacaaag ccgcgggagg agcagtacaa cagcacgtac    1260
cgtgtggtca gcgtcctcac cgtcctgcac caggactggc tgaatggcaa ggagtacaag    1320
tgcaaggtct ccaacaaagc cctcccagcc cccatcgaga aaaccatctc caaagccaaa    1380
gggcagcccc gagaaccaca ggtgtacacc ctgcccccat cccgggatga gctgaccaag    1440
aaccaggtca gcctgacctg cctggtcaaa ggcttctatc ccagcgacat cgccgtggag    1500
tgggagagca atgggcagcc ggagaacaac tacaagacca cgcctcccgt gctggactcc    1560
gacggctcct tcttcctcta cagcaagctc accgtggaca agagcaggtg gcagcagggg    1620
aacgtcttct catgctccgt gatgcatgag gctctgcaca accactacac gcagaagagc    1680
ctctccctgt ctccgggtaa atga                                          1704
```

<210> SEQ ID NO 10
<211> LENGTH: 567
<212> TYPE: PRT
<213> ORGANISM: Homo sapiens

<400> SEQUENCE: 10

```
Met Val Ser Tyr Trp Asp Thr Gly Val Leu Leu Cys Ala Leu Leu Ser
  1               5                  10                  15

Cys Leu Leu Leu Thr Gly Ser Ser Ser Gly Ser Lys Leu Lys Asp Pro
                 20                  25                  30

Glu Leu Ser Leu Lys Gly Thr Gln His Ile Met Gln Ala Gly Gln Thr
             35                  40                  45

Leu His Leu Gln Cys Arg Gly Glu Ala Ala His Lys Trp Ser Leu Pro
         50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95
```

```
Ala Gln Ala Asn His Thr Gly Phe Tyr Ser Cys Lys Tyr Leu Ala Val
            100                 105                 110
Pro Thr Ser Lys Lys Glu Thr Glu Ser Ala Ile Tyr Ile Phe Ile
        115                 120                 125
Ser Asp Thr Gly Arg Pro Phe Val Glu Met Tyr Ser Glu Ile Pro Glu
    130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
        195                 200                 205
Ala Thr Val Asn Gly His Leu Tyr Lys Thr Asn Tyr Leu Thr His Arg
    210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Asn Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
    290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Gly Pro Gly Glu
                325                 330                 335
Pro Lys Ser Cys Asp Lys Thr His Thr Cys Pro Pro Cys Pro Ala Pro
            340                 345                 350
Glu Leu Leu Gly Gly Pro Ser Val Phe Leu Phe Pro Pro Lys Pro Lys
        355                 360                 365
Asp Thr Leu Met Ile Ser Arg Thr Pro Glu Val Thr Cys Val Val Val
    370                 375                 380
Asp Val Ser His Glu Asp Pro Glu Val Lys Phe Asn Trp Tyr Val Asp
385                 390                 395                 400
Gly Val Glu Val His Asn Ala Lys Thr Lys Pro Arg Glu Glu Gln Tyr
                405                 410                 415
Asn Ser Thr Tyr Arg Val Val Ser Val Leu Thr Val Leu His Gln Asp
            420                 425                 430
Trp Leu Asn Gly Lys Glu Tyr Lys Cys Lys Val Ser Asn Lys Ala Leu
        435                 440                 445
Pro Ala Pro Ile Glu Lys Thr Ile Ser Lys Ala Lys Gly Gln Pro Arg
    450                 455                 460
Glu Pro Gln Val Tyr Thr Leu Pro Pro Ser Arg Asp Glu Leu Thr Lys
465                 470                 475                 480
Asn Gln Val Ser Leu Thr Cys Leu Val Lys Gly Phe Tyr Pro Ser Asp
                485                 490                 495
Ile Ala Val Glu Trp Glu Ser Asn Gly Gln Pro Glu Asn Asn Tyr Lys
            500                 505                 510
```

Thr Thr Pro Pro Val Leu Asp Ser Asp Gly Ser Phe Phe Leu Tyr Ser
            515                 520                 525

Lys Leu Thr Val Asp Lys Ser Arg Trp Gln Gln Gly Asn Val Phe Ser
        530                 535                 540

Cys Ser Val Met His Glu Ala Leu His Asn His Tyr Thr Gln Lys Ser
545                 550                 555                 560

Leu Ser Leu Ser Pro Gly Lys
                565

<210> SEQ ID NO 11
<211> LENGTH: 1453
<212> TYPE: DNA
<213> ORGANISM: Homo sapiens

<400> SEQUENCE: 11

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg ttacgtcac     240
ctaacatcac tgttacttta aaaagtttc cacttgacac tttgatccct gatggaaaac     300
gcataatctg gacagtaga aagggcttca tcatatcaaa tgcaacgtac aaagaaatag     360
ggcttctgac ctgtgaagca acagtcaatg gcatttgta taagacaaac tatctcacac     420
atcgacaaac caatacaatc atagatgtgg ttctgagtcc gtctcatgga attgaactat     480
ctgttggaga aagcttgtc ttaaattgta cagcaagaac tgaactaaat gtggggattg     540
acttcaactg gaatacccct tcttcgaagc atcagcataa gaaacttgta aaccgagacc     600
taaaaaccca gtctgggagt gagatgaaga atttttgag caccttaact atagatggtg     660
taacccggag tgaccaagga ttgtacacct gtgcagcatc cagtgggctg atgaccaaga     720
agaacagcac atttgtcagg gtccatgaaa agggcccggg cgacaaaact cacacatgcc     780
caccgtgccc agcacctgaa ctcctggggg gaccgtcagt cttcctcttc cccccaaaac     840
ccaaggacac cctcatgatc tcccggaccc ctgaggtcac atgcgtggtg gtggacgtga     900
gccacgaaga ccctgaggtc aagttcaact ggtacgtgga cggcgtggag gtgcataatg     960
ccaagacaaa gccgcgggag gagcagtaca acagcacgta ccgtgtggtc agcgtcctca    1020
ccgtcctgca ccaggactgg ctgaatggca aggagtacaa gtgcaaggtc tccaacaaag    1080
ccctcccagc ccccatcgag aaaaccatct ccaaagccaa agggcagccc cgagaaccac    1140
aggtgtacac cctgccccca tcccgggatg agctgaccaa gaaccaggtc agcctgacct    1200
gcctggtcaa aggcttctat cccagcgaca tcgccgtgga gtgggagagc aatgggcagc    1260
cggagaacaa ctacaagacc acgcctcccg tgctggactc cgacggctcc ttcttcctct    1320
atagcaagct caccgtggac aagagcaggt ggcagcaggg gaacgtcttc tcatgctccg    1380
tgatgcatga ggctctgcac aaccactaca cgcagaagag cctctccctg tctccgggta    1440
aatgagcggc cgc                                                       1453
```

<210> SEQ ID NO 12
<211> LENGTH: 458
<212> TYPE: PRT
<213> ORGANISM: Homo sapiens

<400> SEQUENCE: 12

Met Val Ser Tyr Trp Asp Thr Gly Val Leu Leu Cys Ala Leu Leu Ser

```
  1               5                   10                  15
Cys Leu Leu Thr Gly Ser Ser Gly Gly Arg Pro Phe Val Glu
            20                  25              30

Met Tyr Ser Glu Ile Pro Glu Ile Ile His Met Thr Glu Gly Arg Glu
            35                  40              45

Leu Val Ile Pro Cys Arg Val Thr Ser Pro Asn Ile Thr Val Thr Leu
            50                  55              60

Lys Lys Phe Pro Leu Asp Thr Leu Ile Pro Asp Gly Lys Arg Ile Ile
65                      70              75                  80

Trp Asp Ser Arg Lys Gly Phe Ile Ile Ser Asn Ala Thr Tyr Lys Glu
                    85                  90              95

Ile Gly Leu Leu Thr Cys Glu Ala Thr Val Asn Gly His Leu Tyr Lys
                100                 105             110

Thr Asn Tyr Leu Thr His Arg Gln Thr Asn Thr Ile Ile Asp Val Val
            115                 120             125

Leu Ser Pro Ser His Gly Ile Glu Leu Ser Val Gly Glu Lys Leu Val
            130                 135             140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170             175

Asp Leu Lys Thr Gln Ser Gly Ser Glu Met Lys Lys Phe Leu Ser Thr
            180                 185             190

Leu Thr Ile Asp Gly Val Thr Arg Ser Asp Gln Gly Leu Tyr Thr Cys
            195                 200             205

Ala Ala Ser Ser Gly Leu Met Thr Lys Lys Asn Ser Thr Phe Val Arg
            210                 215             220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
            245                 250             255

Lys Pro Lys Asp Thr Leu Met Ile Ser Arg Thr Pro Glu Val Thr Cys
            260                 265             270

Val Val Val Asp Val Ser His Glu Asp Pro Glu Val Lys Phe Asn Trp
            275                 280             285

Tyr Val Asp Gly Val Glu Val His Asn Ala Lys Thr Lys Pro Arg Glu
            290                 295             300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330             335

Lys Ala Leu Pro Ala Pro Ile Glu Lys Thr Ile Ser Lys Ala Lys Gly
            340                 345             350

Gln Pro Arg Glu Pro Gln Val Tyr Thr Leu Pro Pro Ser Arg Asp Glu
            355                 360             365

Leu Thr Lys Asn Gln Val Ser Leu Thr Cys Leu Val Lys Gly Phe Tyr
            370                 375             380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410             415

Leu Tyr Ser Lys Leu Thr Val Asp Lys Ser Arg Trp Gln Gln Gly Asn
            420                 425             430
```

Val Phe Ser Cys Ser Val Met His Glu Ala Leu His Asn His Tyr Thr
            435                 440                 445

Gln Lys Ser Leu Ser Leu Ser Pro Gly Lys
    450                 455

<210> SEQ ID NO 13
<211> LENGTH: 1444
<212> TYPE: DNA
<213> ORGANISM: Homo sapiens

<400> SEQUENCE: 13

| | | | | | | |
|---|---|---|---|---|---|---|
| aagcttgggc | tgcaggtcga | tcgactctag | aggatcgatc | cccgggcgag | ctcgaattcg | 60 |
| caaccaccat | ggtcagctac | tgggacaccg | ggtcctgct | gtgcgcgctg | ctcagctgtc | 120 |
| tgcttctcac | aggatctagt | tccggaggta | gacctttcgt | agagatgtac | agtgaaatcc | 180 |
| ccgaaattat | acacatgact | gaaggaaggg | agctcgtcat | tccctgccgg | ttacgtcac | 240 |
| ctaacatcac | tgttactta | aaaagtttc | cacttgacac | tttgatccct | gatggaaaac | 300 |
| gcataatctg | ggacagtaga | aagggcttca | tcatatcaaa | tgcaacgtac | aaagaaatag | 360 |
| ggcttctgac | ctgtgaagca | acagtcaatg | gcatttgta | taagacaaac | tatctcacac | 420 |
| atcgacaaac | caatacaatc | atagatatcc | agctgttgcc | caggaagtcg | ctggagctgc | 480 |
| tggtagggga | gaagctggtc | ctcaactgca | ccgtgtgggc | tgagttaac | tcaggtgtca | 540 |
| cctttgactg | ggactaccca | gggaagcagg | cagagcgggg | taagtgggtg | cccgagcgac | 600 |
| gctcccaaca | gacccacaca | gaactctcca | gcatcctgac | catccacaac | gtcagccagc | 660 |
| acgacctggg | ctcgtatgtg | tgcaaggcca | caacggcat | ccagcgattt | cgggagagca | 720 |
| ccgaggtcat | tgtgcatgaa | aatggcccgg | cgacaaaac | tcacacatgc | ccaccgtgcc | 780 |
| cagcacctga | actcctgggg | ggaccgtcag | tcttcctctt | ccccccaaaa | cccaaggaca | 840 |
| cctcatgat | ctcccggacc | cctgaggtca | catgcgtggt | ggtggacgtg | agccacgaag | 900 |
| accctgaggt | caagttcaac | tggtacgtgg | acggcgtgga | ggtgcataat | gccaagacaa | 960 |
| agccgcggga | ggagcagtac | aacagcacgt | accgtgtggt | cagcgtcctc | accgtcctgc | 1020 |
| accaggactg | gctgaatggc | aaggagtaca | agtgcaaggt | ctccaacaaa | gccctcccag | 1080 |
| cccccatcga | gaaaaccatc | tccaaagcca | aagggcagcc | ccgagaacca | caggtgtaca | 1140 |
| ccctgccccc | atcccgggat | gagctgacca | agaaccaggt | cagcctgacc | tgcctggtca | 1200 |
| aaggcttcta | tcccagcgac | atcgccgtgg | agtgggagag | caatgggcag | ccggagaaca | 1260 |
| actacaagac | cacgcctccc | gtgctggact | ccgacggctc | cttcttcctc | tatagcaagc | 1320 |
| tcaccgtgga | caagagcagg | tggcagcagg | ggaacgtctt | ctcatgctcc | gtgatgcatg | 1380 |
| aggctctgca | caaccactac | acgcagaaga | gcctctccct | gtctccgggt | aaatgagcgg | 1440 |
| ccgc | | | | | | 1444 |

<210> SEQ ID NO 14
<211> LENGTH: 455
<212> TYPE: PRT
<213> ORGANISM: Homo sapiens

<400> SEQUENCE: 14

Met Val Ser Tyr Trp Asp Thr Gly Val Leu Leu Cys Ala Leu Leu Ser
  1               5                  10                  15

Cys Leu Leu Thr Gly Ser Ser Ser Gly Gly Arg Pro Phe Val Glu
            20                  25                  30

```
Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
        50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Ile Gln
            115                 120                 125

Leu Leu Pro Arg Lys Ser Leu Glu Leu Leu Val Gly Glu Lys Leu Val
        130                 135                 140

Leu Asn Cys Thr Val Trp Ala Glu Phe Asn Ser Gly Val Thr Phe Asp
145                 150                 155                 160

Trp Asp Tyr Pro Gly Lys Gln Ala Glu Arg Gly Lys Trp Val Pro Glu
                165                 170                 175

Arg Arg Ser Gln Gln Thr His Thr Glu Leu Ser Ser Ile Leu Thr Ile
            180                 185                 190

His Asn Val Ser Gln His Asp Leu Gly Ser Tyr Val Cys Lys Ala Asn
        195                 200                 205

Asn Gly Ile Gln Arg Phe Arg Glu Ser Thr Glu Val Ile Val His Glu
        210                 215                 220

Asn Gly Pro Gly Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
```

<210> SEQ ID NO 15
<211> LENGTH: 1377
<212> TYPE: DNA
<213> ORGANISM: Homo sapiens

<400> SEQUENCE: 15

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata gaaacttgt aaaccgagac     540
ctaaaaaccc agtctgggag tgagatgaag aaattttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta acagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga      1377
```

<210> SEQ ID NO 16
<211> LENGTH: 458
<212> TYPE: PRT
<213> ORGANISM: Homo sapiens

<400> SEQUENCE: 16

```
Met Val Ser Tyr Trp Asp Thr Gly Val Leu Leu Cys Ala Leu Leu Ser
  1               5                  10                  15

Cys Leu Leu Thr Gly Ser Ser Ser Gly Ser Asp Thr Gly Arg Pro
             20                  25                  30

Phe Val Glu Met Tyr Ser Glu Ile Pro Glu Ile Ile His Met Thr Glu
         35                  40                  45

Gly Arg Glu Leu Val Ile Pro Cys Arg Val Thr Ser Pro Asn Ile Thr
     50                  55                  60

Val Thr Leu Lys Lys Phe Pro Leu Asp Thr Leu Ile Pro Asp Gly Lys
 65                  70                  75                  80
```

```
Arg Ile Ile Trp Asp Ser Arg Lys Gly Phe Ile Ile Ser Asn Ala Thr
            85                  90                  95

Tyr Lys Glu Ile Gly Leu Leu Thr Cys Glu Ala Thr Val Asn Gly His
        100                 105                 110

Leu Tyr Lys Thr Asn Tyr Leu Thr His Arg Gln Thr Asn Thr Ile Ile
            115                 120                 125

Asp Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
            195                 200                 205

Tyr Thr Cys Ala Ala Ser Ser Gly Leu Met Thr Lys Lys Asn Ser Thr
        210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 17
<211> LENGTH: 4
<212> TYPE: PRT
<213> ORGANISM: Homo sapiens

<400> SEQUENCE: 17
```

-continued

Val Val Leu Ser
1

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
gactagcagt ccggaggtag acctttcgta gagatg                                36

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
cggactcaga accacatcta tgattgtatt ggt                                   33

<210> SEQ ID NO 20
<211> LENGTH: 7
<212> TYPE: PRT
<213> ORGANISM: Homo sapiens

<400> SEQUENCE: 20

Gly Arg Pro Phe Val Glu Met
1               5

<210> SEQ ID NO 21
<211> LENGTH: 35
<212> TYPE: DNA
<213> ORGANISM: Artificial Sequence
<220> FEATURE:
<223> OTHER INFORMATION: Primer

<400> SEQUENCE: 21
acaatcatag atgtggttct gagtccgtct catgg                                 35

<210> SEQ ID NO 22
<211> LENGTH: 38
<212> TYPE: DNA
<213> ORGANISM: Artificial Sequence
<220> FEATURE:
<223> OTHER INFORMATION: Primer

<400> SEQUENCE: 22
gataatgccc gggcccttttt catggaccct gacaaatg                             38

<210> SEQ ID NO 23
<211> LENGTH: 6
<212> TYPE: PRT
<213> ORGANISM: Homo sapiens

<400> SEQUENCE: 23

Val Arg Val His Glu Lys
1               5

<210> SEQ ID NO 24
<211> LENGTH: 36
<212> TYPE: DNA
<213> ORGANISM: Artificial Sequence

```
<220> FEATURE:
<223> OTHER INFORMATION: Primer

<400> SEQUENCE: 24
gactagcagt ccggaggtag acctttcgta gagatg                         36

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
ttcctgggca acagctggat atctatgatt gtattggt                       38

<210> SEQ ID NO 26
<211> LENGTH: 6
<212> TYPE: DNA
<213> ORGANISM: Artificial Sequence
<220> FEATURE:
<223> OTHER INFORMATION: Mutant

<400> SEQUENCE: 26 tccgga                                                          6

<210> SEQ ID NO 27
<211> LENGTH: 39
<212> TYPE: DNA
<213> ORGANISM: Artificial Sequence
<220> FEATURE:
<223> OTHER INFORMATION: Primer

<400> SEQUENCE: 27
atccagctgt tgcccaggaa gtcgctggag ctgctggta                      39

<210> SEQ ID NO 28
<211> LENGTH: 39
<212> TYPE: DNA
<213> ORGANISM: Artificial Sequence
<220> FEATURE:
<223> OTHER INFORMATION: Primer

<400> SEQUENCE: 28
attttcatgc acaatgacct cggtgctctc ccgaaatcg                      39

<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
tcatagatat ccagctgttg cccaggaagt cgctggag                       38

<210> SEQ ID NO 30
<211> LENGTH: 39
<212> TYPE: DNA
<213> ORGANISM: Artificial Sequence
<220> FEATURE:
<223> OTHER INFORMATION: Primer

<400> SEQUENCE: 30
gataatgccc gggccatttt catgcacaat gacctcggt                      39
```

```
<210> SEQ ID NO 31
<211> LENGTH: 6
<212> TYPE: PRT
<213> ORGANISM: Homo sapiens

<400> SEQUENCE: 31

Val Ile Val His Glu Asn
1               5

<210> SEQ ID NO 32
<211> LENGTH: 10
<212> TYPE: PRT
<213> ORGANISM: Homo sapiens

<400> SEQUENCE: 32

Lys Asn Lys Arg Ala Ser Val Arg Arg Arg
1               5                   10

<210> SEQ ID NO 33
<211> LENGTH: 8
<212> TYPE: PRT
<213> ORGANISM: Homo sapiens

<400> SEQUENCE: 33

Asn Ala Ser Val Asn Gly Ser Arg
1               5

<210> SEQ ID NO 34
<211> LENGTH: 10
<212> TYPE: PRT
<213> ORGANISM: Homo sapiens

<400> SEQUENCE: 34

Lys Asn Lys Cys Ala Ser Val Arg Arg Arg
1               5                   10

<210> SEQ ID NO 35
<211> LENGTH: 4
<212> TYPE: PRT
<213> ORGANISM: Homo sapiens

<400> SEQUENCE: 35

Ser Lys Leu Lys
1
```

METHODS OF TREATING EYE DISORDERS WITH MODIFIED CHIMERIC POLYPEPTIDES

CROSS-REFERENCE TO RELATED APPLICATIONS

This application is a continuation-in-part of application Ser. No. 10/009,852 filed 6 Dec. 2001, now U.S. Pat. No. 7,070,959, which is the National Stage of International Application No. PCT/US00/14142 filed 23 May 2000, which claims the benefit under 35 USC § 119(e) of U.S. Provisional 60/138,133 filed 8 Jun. 1999, which applications are herein specifically incorporated by reference in their entireties.

BACKGROUND

STATEMENT REGARDING RELATED ART

A class of cell-derived dimeric mitogens with selectivity for vascular endothelial cells has been identified and designated vascular endothelial cell growth factor (VEGF). VEGF is a dimer with an apparent molecular mass of about 46 kDa with each subunit having an apparent molecular mass of about 23 kDa. The membrane-bound tyrosine kinase receptor, known as Flt (also known as VEGFR2), was shown to be a VEGF receptor (DeVries et al. (1992) Science 255:989991). Another form of the VEGF receptor, designated KDR or Flk-1 (also known as VEGFR3), is also known to bind VEGF and induce mitogenesis (Terman et al. (1991) Oncogene 6:1677-1683; Terman et al. (1992) Biochem. Biophys. Res. Comm. 187:1579-1586).

U.S. Pat. No. 6,011,003 describes an altered, soluble form of Flt polypeptide capable of binding to VEGF comprising five or fewer complete immunoglobulin domains. WO 97/44453 describes chimeric VEGF receptor proteins comprising amino acid sequences derived from VEGF receptors Flt1 and KDR.

BRIEF SUMMARY OF THE INVENTION

In a first aspect, the invention provides an isolated nucleic acid molecule, comprising (a) a nucleotide sequence encoding a vascular endothelial growth factor (VEGF) receptor component consisting essentially of an immunoglobulin-like (Ig) domain 2 of a first VEGF receptor and Ig domain 3 of a second VEGF receptor; and (b) a nucleotide sequence encoding a multimerizing component, wherein the first VEGF receptor is Flt1, the second VEGF receptor is Flk1 or Flt4, and the VEGF receptor component is the only VEGF receptor component of the fusion polypeptide. In one embodiment, the nucleotide sequence encoding Ig domain 2 of the extracellular domain of the first VEGF receptor is upstream of the nucleotide sequence encoding Ig domain 3 of the extracellular domain of the second VEGF receptor. In another embodiment, the nucleotide sequence encoding Ig domain 2 of the extracellular domain of the first VEGF receptor is downstream of the nucleotide sequence encoding Ig domain 3 of the extracellular domain of the second VEGF receptor. In one embodiment, the multimerizing component comprises an immunoglobulin domain. Preferably, the immunoglobulin domain is the Fc domain of IgG or the heavy chain of IgG. In specific embodiments, the nucleotide sequence is selected from the group consisting of the nucleotide sequence of SEQ ID NO:11, 13, and 15, or a nucleotide sequence which, as a result of the degeneracy of the genetic code, differs from the nucleotide sequence of SEQ ID NO:11, 13, and 15.

The components of the fusion polypeptide encoded by the nucleic acid molecule of the invention are arranged as 1,2,3; 1,3,2; 2,1,3; 2,3,1; 3,1,2; or 3,2,1, wherein 1 is the first VEGF receptor component, 2 is the second VEGF receptor component, and 3 is the multimerizing component.

In a second aspect, the invention features a vector comprises a nucleic acid molecule of the invention. In a more specific embodiment, the vector is an expression vector comprising the nucleic acid molecule of the invention operatively linked to an expression control sequence.

In a third aspect, the invention features a host-vector system for the production of a fusion polypeptide which comprises the expression vector of the invention in a suitable host cell. The suitable host cell may be a bacterial cell, yeast cell, insect cell, or mammalian cell. In a preferred embodiment, the host cell is an *E. coli* cell or a CHO cell.

In a fourth aspect, the invention features a method of producing a fusion polypeptide which comprises growing cells of the host-vector system of the invention under conditions permitting production of the fusion polypeptide and recovering the fusion polypeptide so produced.

In a fifth aspect, the invention features a dimeric vascular endothelial growth factor (VEGF) antagonist, comprising two fusion polypeptides, each fusion polypeptide comprising (a) a VEGF receptor component consisting essentially of an immunoglobulin-like (Ig) domain 2 of an Flt-1 VEGF receptor and Ig domain 3 of an Flk-1 or Flt-4 VEGF receptor; and (b) a multimerizing component, wherein the VEGF receptor component is the only VEGF receptor component of each fusion protein. In specific embodiments, the dimeric VEGF antagonist is modified by acetylation or pegylation.

In a sixth aspect, the invention features a fusion polypeptide, comprising (a) a VEGF receptor component consisting essentially of an immunoglobulin-like (Ig) domain 2 of an Flt-1 VEGF receptor and Ig domain 3 of an Flk-1 or Flt-4 VEGF receptor; and (b) a multimerizing component, wherein the VEGF receptor component is the only VEGF receptor component of the fusion polypeptide. In one embodiment, the multimerizing component comprises an immunoglobulin domain. More specifically, the multimerizing component is an immunoglobulin domain which is one of the Fc domain of IgG or the heavy chain of IgG. In specific embodiments, the fusion polypeptide comprises an amino acid sequence selected from the group consisting of SEQ ID NO:12 (Flt1D2. Flk1D3FcΔC1(a)), SEQ ID NO:14 (Flt1D2VEGFR3D3FcΔC1(a)), and SEQ ID NO:16 (VEGFR1R2 FcΔC1(a)).

In a seventh aspect, the invention features a pharmaceutical composition comprising the fusion polypeptide of the invention and a pharmaceutically acceptable carrier.

In an eighth aspect, the invention features a therapeutic method for treating or ameliorating an eye disorder, comprising administering the pharmaceutical composition of the invention to a patient in need thereof. In one embodiment, the eye disorder treated is age related macular degeneration. In another embodiment, the eye disorder treated is diabetic retinopathy Other objects and advantages will become apparent from a review of the ensuing detailed description.

BRIEF DESCRIPTION OF THE FIGURES

FIG. 6. Biacore analysis of binding stoichiometry. Binding stoichiometry was calculated as a molar ratio of bound VEGF165 to the immobilized Flt1D2Flk1D3. FcΔC1(a) or VEGFR1R2-FcΔC1(a), using the conversion factor of 1000 RU equivalent to 1 ng/ml.

DETAILED DESCRIPTION OF THE INVENTION

Figure 1:
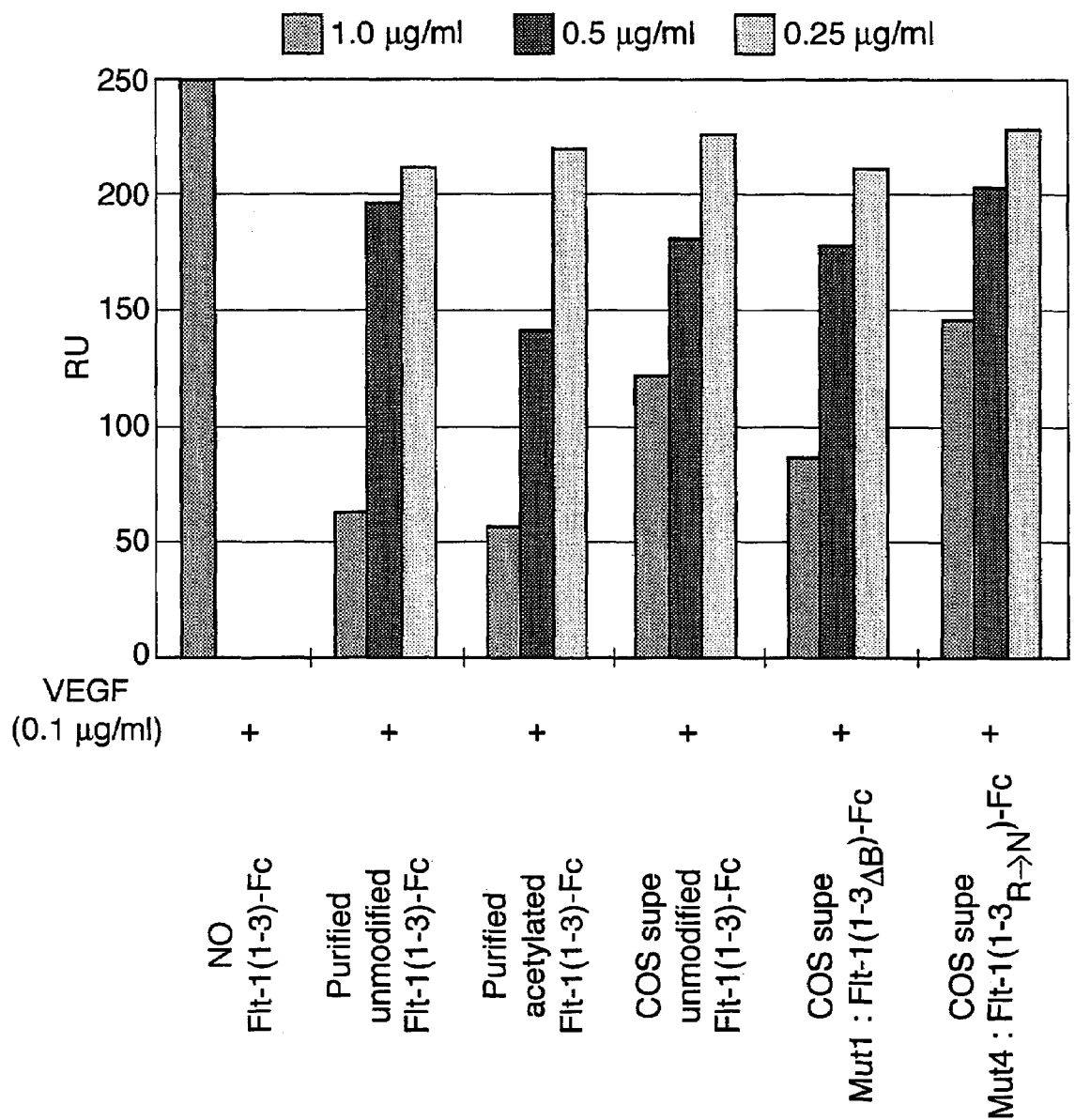
FIG. 1. Binding of unmodified Flt1(1-3)-Fc, basic region deletion mutant Flt1(1-3)-Fc, and Flt1(1-$^3$)$_{R\rightarrow N}$ mutant proteins in a Biacore-based assay.

It has been a long standing problem in the art to produce a receptor based VEGF antagonist that has a pharmacokinetic profile that is appropriate for consideration of the antagonist as a therapeutic candidate. Applicants describe herein, for the first time, a chimeric polypeptide molecule, capable of antagonizing VEGF activity, that exhibits improved pharmacokinetic properties as compared to other known receptor-based VEGF antagonists. The chimeric polypeptide molecules described herein thus provide for the first time appropriate molecules for use in therapies in which antagonism of VEGF is a desired result.

The extracellular ligand binding domain is defined as the portion of a receptor that, in its native conformation in the cell membrane, is oriented extracellularly where it can contact with its cognate ligand. The extracellular ligand binding domain does not include the hydrophobic amino acids associated with the receptor's transmembrane domain or any amino acids associated with the receptor's intracellular domain. Generally, the intracellular or cytoplasmic domain of a receptor is usually composed of positively charged or polar amino acids (i.e. lysine, arginine, histidine, glutamic acid, aspartic acid). The preceding 15-30, predominantly hydrophobic or apolar amino acids (i.e. leucine, valine, isoleucine, and phenylalanine) comprise the transmembrane domain. The extracellular domain comprises the amino acids that precede the hydrophobic transmembrane stretch of amino acids. Usually the transmembrane domain is flanked by positively charged or polar amino acids such as lysine or arginine. von Heijne has published detailed rules that are commonly referred to by skilled artisans when determining which amino acids of a given receptor belong to the extracellular, transmembrane, or intracellular domains (See, von Heijne (1995) BioEssays 17:25.

Nucleic Acid Constructs

The present invention provides for the construction of nucleic acid molecules encoding chimeric polypeptide molecules that are inserted into a vector that is able to express the chimeric polypeptide molecules when introduced into an appropriate host cell. Appropriate host cells include, but are not limited to, bacterial cells, yeast cells, insect cells, and mammalian cells. Any of the methods known to one skilled in the art for the insertion of DNA fragments into a vector may be used to construct expression vectors encoding the chimeric polypeptide molecules under control of transcriptional/translational control signals. These methods may include in vitro recombinant DNA and synthetic techniques and in vivo recombinations (See Sambrook, et al., Molecular Cloning, A Laboratory Manual, Cold Spring Harbor Laboratory; Current Protocols in Molecular Biology, Eds. Ausubel, et al., Greene Publ. Assoc., Wiley-Interscience, N.Y.).

Expression of nucleic acid molecules encoding the chimeric polypeptide molecules may be regulated by a second nucleic acid sequence so that the chimeric polypeptide molecule is expressed in a host transformed with the recombinant DNA molecule. For example, expression of the chimeric polypeptide molecules described herein may be controlled by any promoter/enhancer element known in the art. Promoters which may be used to control expression of the chimeric polypeptide molecules include, but are not limited to, the long terminal repeat as described in Squinto et al., (1991, Cell 65:1-20); the SV40 early promoter region (Bernoist et al. (1981) Nature 290:304-310), the CMV promoter, the M-MuLV 5' terminal repeat the promoter contained in the 3' long terminal repeat of Rous sarcoma virus (Yamamoto et al. (1980) Cell 22:787-797), the herpes thymidine kinase promoter (Wagner et al. (1981) Proc. Natl. Acad. Sci. U.S.A. 78:144-1445), the regulatory sequences of the metallothionine gene (Brinster et al. (1982) Nature 296:39-42); prokaryotic expression vectors such as the β-lactamase promoter (Villa-Kamaroff et al. (1978) Proc. Natl. Acad. Sci. U.S.A. 75:3727-3731), or the tac promoter (DeBoer et al. (1983) Proc. Natl. Acad. Sci. U.S.A. 80:21-25); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (see for example, Swift et al. (1984) Cell 38:639-646); insulin gene control region which is active in pancreatic beta cells (Hanahan (1985) Nature 315:115-122), immunoglobulin gene control region which is active in lymphoid cells (Grosschedl et al. (1984) Cell 38:647-658), mouse mammary tumor virus control region which is active in testicular, breast, lymphoid and mast cells (Leder et al. (1986) Cell 45:485-495), albumin gene control region which is active in liver (Pinkert et al. (1987) Genes Devel. 1:268-276), alpha-fetoprotein gene control region which is active in liver (Krumlauf et al. (1985) Mol. Cell. Biol. 5:1639-1648); alpha 1-antitrypsin gene control region which is active in the liver (Kelsey et al. (1987) Genes Devel. 1:161-171), beta-globin gene control region which is active in myeloid cells (Mogram et al. (1985) Nature 315:338-340); myelin basic protein gene control region which is active in oligodendrocyte cells in the brain (Readhead et al. (1987) Cell 48:703-712); myosin light chain-2 gene control region which is active in skeletal muscle (Shani (1985) Nature 314:283-286), and gonadotropic releasing hormone gene control region which is active in the hypothalamus (Mason et al. (1986) Science 234:1372-1378).

Thus, according to the invention, expression vectors capable of being replicated in a bacterial or eukaryotic host comprising chimeric polypeptide molecule-encoding nucleic acid as described herein, are used to transfect the host and thereby direct expression of such nucleic acids to produce the chimeric polypeptide molecules, which may then be recovered in a biologically active form. As used herein, a biologically active form includes a form capable of binding to VEGF. Expression vectors containing the chimeric nucleic acid molecules described herein can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to the inserted chimeric polypeptide molecule sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the chimeric polypeptide molecule DNA sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of the chimeric polypeptide molecules.

Cells of the present invention may transiently or, preferably, constitutively and permanently express the chimeric polypeptide molecules.

The chimeric polypeptide molecules may be purified by any technique which allows for the subsequent formation of a stable, biologically active chimeric polypeptide molecule. For example, and not by way of limitation, the factors may be recovered from cells either as soluble proteins or as inclusion bodies, from which they may be extracted quantitatively by 8M guanidinium hydrochloride and dialysis (see, for example, U.S. Pat. No. 5,663,304). In order to further purify the factors, conventional ion exchange chromatography, hydrophobic interaction chromatography, reverse phase chromatography or gel filtration may be used.

Therapeutic Methods

The present invention also has diagnostic and therapeutic utilities. In particular embodiments of the invention, methods of detecting aberrancies in the function or expression of the chimeric polypeptide molecules described herein may be used in the diagnosis of disorders. In other embodiments, manipulation of the chimeric polypeptide molecules or agonists or antagonists which bind the chimeric polypeptide molecules may be used in the treatment of diseases. In further embodiments, the chimeric polypeptide molecule is utilized as an agent to block the binding of a binding agent to its target.

By way of example, but not limitation, the method of the invention may be useful in treating clinical conditions that are characterized by vascular permeability, edema or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy.

Specific Embodiments

The eye comprises several structurally and functionally distinct vascular beds, which supply ocular components critical to the maintenance of vision. These include the retinal and choroidal vasculatures, which supply the inner and outer portions of the retina, respectively, and the limbal vasculature located at the periphery of the cornea. Injuries and diseases that impair the normal structure or function of these vascular beds are among the leading causes of visual impairment and blindness. For example, diabetic retinopathy is the most common disease affecting the retinal vasculature, and is the leading cause of vision loss among the working age population in the United States, while the wet form of age-related macular degeneration (AMD) is the most common form of choroidal neovascularization and a leading cause of blindness in the elderly. Vascularization of the cornea secondary to injury or disease is yet another category of ocular vascular disease that can lead to severe impairment of vision.

Each of the above conditions is characterized by pathological neovascularization, associated with or preceded by abnormal, excessive vascular permeability that often leads to pronounced edema in the affected tissue (cornea or retina). The production of abnormally high levels of VEGF has been implicated as a principal cause of the increased vascular permeability, as well as pathological angiogenesis (Aiello et al. (1994) N. Engl. J. Med. 331:1480-1487). Moreover, both the edema associated with abnormal vascular permeability and pathological neovascularization contribute directly to the impairments of vision. Therefore, inhibition of VEGF action is one strategy now being explored for the treatment of ocular vascular diseases such as diabetic retinopathy and AMD.

Other features of the invention will become apparent in the course of the following descriptions of exemplary embodiments which are given for illustration of the invention and are not intended to be limiting thereof.

EXAMPLES

Example 1

Expression of Flt1(1-3)-Fc Protein in CHO K1 Cells

Using standard molecular biology techniques (see Sambrook et al. supra), the gene encoding Flt1(1-3)-Fc was inserted into the expression vector pEE14.1 (Lonza Biologics) at a multiple cloning site downstream of the CMV promoter. CHO K1 cells were transfected with the pEE14.1/Flt1(1-3)-Fc DNA construct using lipofectamine (Gaithersburg, Md.). The transfected CHO K1 cells were grown in glutamine-free DMEM (JRH, Kansas City, Mo.) containing 25 µM methionine sulfoximine (MSX) from Sigma Inc., St. Louis, Mo., and high recombinant protein expressors were obtained by screening the CHO K1 cell supernatants from over 100 hand-picked colony isolates using a standard immunoassay which captures and detects human Fc. The selected hand-picked clone was amplified in the presence of 100 µM MSX followed by a second round of screening of the amplified clones. The highest producing clone had a specific productivity of recombinant Flt1(1-3)-Fc protein of 55 pg/cell/day.

The selected clone was expanded in 225 $cm^2$ T-flasks (Corning, Acton, Mass.) and then into 8.5 L roller bottles (Corning, Acton, Mass.) using the cell culture media described supra. Cells were removed from the roller bottles by standard trypsinization and put into 3.5 L of suspension medium. The suspension medium is comprised of glutamine-free ISCHO medium (Irvine Scientific, Santa Ana, Calif.) containing 5% fetal bovine serum (FBS from Hyclone Labs, Logan, Utah), 100 µM MSX and GS supplement (JRH Scientific, Kansas City, Mo.) in a 5 L Celligen bioreactor (New Brunswick Scientific, New Brunswick, N.J.) at a density of $0.3 \times 10^6$ cells/mL. After the cells reached a density of $3.6 \times 10^6$/mL and were adapted to suspension they were transferred to a 60 L bioreactor (ABEC, Allentown, Pa.) at a density of $0.5 \times 10^6$ cells/mL in 20 L of ISCHO medium with 5% fetal bovine serum. After two days an additional 20 L of ISCHO+5% fetal bovine serum was added to the bioreactor. The cells were allowed to grow for an additional two days reaching a final density of $3.1 \times 10^6$ cells/mL, and a final Flt1(1-3)-Fc concentration at harvest was 95 mg/L. At harvest the cells were removed by tangential flow filtration using 0.45 µm Prostak Filters (Millipore, Inc., Bedford, Mass.).

Example 2

Purification of Flt1(1-3)-Fc Protein Obtained from CHO K1 Cells

Flt1(1-3)-Fc protein was initially purified by affinity chromatography. A Protein A column was used to bind, with high specificity, the Fc portion of the molecule. This affinity-purified protein was then concentrated and passed over a SEC column. The protein was then eluted into the formulation buffer. The following describes these procedures in detail.

Materials and Methods. All chemicals were obtained from J. T. Baker, Phillipsburg, N.J. with the exception of PBS, which was obtained as a 10× concentrate from Life Technologies, Gaithersburg, Md. Protein A Fast Flow and Superdex 200 preparation grade resins were obtained from Pharmacia, Piscataway, N.J. Equipment and membranes for protein concentration were obtained from Millipore, Bedford, Mass.

Approximately 40 L of 0.45 µm-filtered CHO conditioned media containing Flt1(1-3)-Fc protein was applied to a 290 mL Protein A Fast Flow column (10 cm diameter) that had been equilibrated with PBS. The column was washed with PBS containing 350 mM NaCl and 0.02% CHAPS and the bound protein was eluted with 20 mM Citric Acid containing 10 mM $Na_2HPO_4$. The single peak in the elution was collected and its pH was raised to neutrality with 1M NaOH. The eluate fractions was concentrated to approximately 9 mg/mL using 10K regenerated cellulose membranes by both tangential flow filtration and by stirred cell concentration. To remove aggregates and other contaminants, the concentrated protein was applied to a column packed with Superdex 200 preparation grade resin (10 cm×55 cm) and run in PBS containing 5% glycerol. The main peak fractions were pooled, sterile filtered, aliquoted and stored at −80° C.

Example 3

Acetylation of Flt1(1-3)-Fc Protein

Two milligrams of Flt1(1-3)-Fc protein were acetylated as described in the instruction manual provided with the sulfo-NHS-acetate modification kit (Pierce Chemical Co., Rockford, Ill., Cat.#26777).

Example 4

Characterization of Acetylation of Flt1(1-3)-Fc Protein

IEF analysis: Flt1(1-3)-Fc and acetylated Flt1(1-3)-Fc were analyzed by standard IEF analysis. Flt1(1-3)-Fc protein is not able to migrate into the gel and therefore must have a pI greater than 9.3, the highest pI in the standard. However, acetylated Flt1(1-3)-Fc is able to migrate into the gel and equilibrate at a pI of approximately 5.2. This result demonstrates that acetylation reduces the net positive charge of the protein and therefore its pI considerably.

Binding to extracellular matrix components. To test for binding to extracellular matrix components, Flt1(1-3)-Fc and acetylated Flt1(1-3)-Fc where tested in an assay designed to mimic the interaction with extracellular matrix components. In this assay, 96-well tissue culture plates are coated with Matrigel (Biocoat MATRIGEL® matrix thin layer 96 well plate, Catalog #40607, Becton Dickinson Labware, Bedford, Mass.). The plates are incubated with varying concentrations of either Flt1(1-3)-Fc, acetylated Flt1(1-3)-Fc, or rTie2-Fc (an irrelevant control) protein are added to the wells. The plates are incubated for 1-2 hours at either room temperature or 37° C. degrees and then detection of bound proteins is accomplished by adding a secondary alkaline phosphatase-conjugated anti-human Fc antibody to the wells. Finally, alkaline phosphatase substrate is added to the wells and optical density is measured. Like the irrelevant control protein rTie2-Fc, acetylated Flt1(1-3)-Fc does not exhibit any binding to the Matrigel coated plate, whereas the non-acetylated Flt1(1-3)-Fc protein exhibits significant binding. This result indicates that acetylation of basic amino acid residues is an effective way to interfere with the charge interactions that exist between positively charged proteins and the negatively charged extracellular matrix components they are exposed to in vivo.

Example 5

Pegylation of Flt1(1-3)-Fc Protein

Materials and Methods. Purified Flt1(1-3)-Fc derived from CHO cells (see supra) was used in the following pegylation experiments. Functionalized PEGs were obtained from Shearwater Polymers, Huntsville, Ala.; Bicine from Sigma, St Louis, Mo.; Superose 6 column from Pharmacia, Piscataway, N.J.; PBS as a 10× concentrate from Life Technologies, Gaithersburg, Md.; Glycerol from J. T. Baker, Phillipsburg, N.J.; and Bis-Tris precast gels from Novex, Calif.

20K PEG strands functionalized with amine-specific terminal moieties were used in small-scale reaction studies that were set-up to evaluate different reaction conditions in which the PEG:protein stoichiometry was varied. Based on these reactions and the analyses of samples on standard SDS-PAGE, Flt1(1-3)-Fc at a concentration of 1.5 mg/mL was reacted at pH 8.1 with 20K SPA-PEG (PEG succinimidyl propionate) molecules at a PEG-to-Flt1(1-3)-Fc monomer molar ratio of 1:6. The reaction was allowed to proceed at 8° C. overnight. For initial purification, the reaction products were applied to a 10 mm×30 cm Superose 6 column equilibrated with PBS containing 5% Glycerol. The column appeared to separate pegylated Flt1(1-3)-Fc molecules based on the extent of pegylation. Fractions corresponding to what appeared to be primarily mono-pegylated and di-pegylated dimeric Flt1(1-3)-Fc, as judged by banding patterns on reducing and non-reducing SDS-PAGE gels were pooled. The protein concentration was determined by measuring absorbance at 280 nm. The pegylated Flt1(1-3)-Fc protein was sterile filtered, aliquoted and stored at −40° C.

Example 6

Binding of Unmodified, Acetylated, and Pegylated Flt1(1-3)-Fc

Unmodified, acetylated, and pegylated Flt1(1-3)-Fc proteins were tested in a Biacore-based assay to evaluate their ability to bind to the Flt1 ligand, VEGF. In this assay, unmodified Flt1(1-3)-Fc protein was immobilized on the surface of a Biacore chip (see Biacore Instruction Manual, Pharmacia, Inc., Piscataway, N.J., for standard procedures) and a sample containing 0.2 µg/ml VEGF and either unmodified Flt1(1-3)-Fc, acetylated Flt1(1-3)-Fc or pegylated Flt1(1-3)-Fc (each at 25 µg/ml) was passed over the Flt1(1-3)-Fc-coated chip. To minimize the effects of non-specific binding, the bound samples were washed with a 0.5M NaCl wash. In one sample, unmodified Flt1(1-3)-Fc was mixed with heparin. Heparin is a negatively charged molecule and the Flt1(1-3)-Fc protein is a positively charged molecule, so when the two molecules are mixed together, they should interact through their respective charges. This essentially neutralizes Flt1(1-3)-Fc's inherent positive charge making the molecule behave as if it has been chemically or genetically modified so as to reduce its charge and its tendency to bind via charge interactions. Acetylated, pegylated, and heparin-treated Flt1(1-3)-Fc are each able to completely compete with the Biacore chip-bound Flt1(1-3)-Fc for VEGF binding as compared to control and irrelevant protein. Unmodified Flt1(1-3)-Fc appeared to only partially compete with Biacore chip-bound Flt1(1-3)-Fc for VEGF binding. However, washing the bound samples with 0.5M NaCl resulted in a binding profile similar to the modified forms of Flt1(1-3)-Fc, indicating that the unmodified protein was exhibiting non-specific binding to the chip that could be eliminated by the salt wash.

Example 7

Binding of Unmodified, Acetylated, and Pegylated Flt1(1-3)-Fc in an ELISA-Based Assay Unmodified, acetylated, and pegylated Flt1(1-3)-Fc proteins were tested in a standard ELISA-based assay to evaluate their ability to bind the Flt1 receptor ligand VEGF. Both pegylated and acetylated Flt1(1-3)-Fc proteins are capable of binding to VEGF, demonstrating that modifying the protein either by pegylation or acetylation does not destroy its ability to bind its ligand.

Example 8

Pharmacokinetic Analysis of Unmodified Flt1(1-3)-Fc, Acetylated Flt1(1-3)-Fc, and Pegylated Flt1(1-3)-Fc In vivo experiments were designed to assess the pharmacokinetic profiles of unmodified Flt1(1-3)-Fc, acetylated Flt1(1-3)-Fc, and pegylated Flt1(1-3)-Fc protein. Balb/c mice (23-28 g; 3 mice/group) were injected subcutaneously with 4 mg/kg of unmodified, acetylated, or pegylated Flt1(1-3)-Fc. The mice were tail bled at 1, 2, 4, 6, 24 hours, 2 days, and 3 days after injection of protein. The sera were assayed in a standard ELISA-based assay designed to detect Flt1(1-3)-Fc protein. Briefly, the assay involves coating an ELISA plate with VEGF, binding the unmodified, acetylated, or pegylated Flt1(1-3)-Fc-containing sera, and reporting with an anti-Fc antibody linked to alkaline phosphatase. The Tmax for all of the Flt1(1-3)-Fc proteins was between the 6 hour and 24 hour time points. The Cmax for the different proteins was as follows: Unmodified: 0.06 µ/ml-0.15 µg/ml; acetylated: 1.5 µg/ml-4.0 µg/ml; and pegylated: approximately 5 µg/ml.

Example 9

Step-Acetylation of Flt1(1-3)-Fc

To determine what minimal amount of acetylation is necessary to eliminate binding to extracellular matrix components, an experiment was designed that acetylated the Flt1(1-3)-Fc protein in a step-wise fashion by using increasing amounts of molar excess of acetylation reagent in the acetylation reaction mixture. The range of molar excess was as follows: 0, 10, 20, 30, 40, 50, 60, 70, 80, 90, and 100 moles of acetylation reagent per 1 mole of Flt1(1-3)-Fc monomer. The reactions were performed as detailed in the instruction manual provided with the sulfo-NHS-Acetate modification kit (Pierce Chemical Co., Rockford, Ill., Cat. #26777).

Example 10

Characterization of Step-Acetylated Flt1(1-3)-Fc

IEF analysis. Unmodified Flt1(1-3)-Fc and step-acetylated Flt1(1-3)-Fc proteins were analyzed by standard IEF analysis. Unmodified Flt1(1-3)-Fc protein was not able to migrate into the gel due to its extremely high pI (greater than 9.3). However, most of the step-acetylated Flt1(1-3)-Fc samples (30-100 fold molar excess samples) were able to migrate into the gel and equilibrate at pIs ranging between 4.55-8.43, depending on the degree of acetylation of the protein. This result demonstrates that acetylation can change the positive charge of the protein in a dose-dependent manner and that reduction of the pI can be controlled by controlling the degree of acetylation.

Binding of step-acetylated Flt1(1-3)-Fc to extracellular matrix components. To test for binding to extracellular matrix components, Flt1(1-3)-Fc and step-acetylated Flt1(1-3)-Fc where tested in the above-described assay designed to mimic the interaction with extracellular matrix components. Varying concentrations of either unmodified Flt1(1-3)-Fc, step-acetylated Flt1(1-3)-Fc (10, 20, and 30 fold molar excess samples), or rTie2-Fc (an irrelevant control) protein were added to the wells. The plates were incubated for 1-2 hours at room temperature or 37° C. and then detection of bound proteins was accomplished by adding a secondary alkaline phosphatase-conjugated anti-human Fc antibody to the wells. Alkaline phosphatase substrate was subsequently added to the wells and optical density measured. Like the irrelevant control protein rTie2-Fc, step-acetylated Flt1(1-3)-Fc (20 and 30 fold molar excess samples) did not exhibit any significant binding to the Matrigel coated plate, whereas the non-acetylated Flt1(1-3)-Fc protein exhibited significant binding. The binding is saturable, indicating that the Flt1 (1-3)-Fc protein may be binding to specific sites, rather than a more general charge-mediated interaction that might not be saturable. The 10 fold molar excess sample showed reduced binding, but the degree of acetylation was not enough to completely block binding to extracellular matrix components. The 20 fold molar excess and higher samples displayed no detectable binding, despite the fact that by IEF analysis the lower molar excess samples still had a large net positive charge. This result demonstrates that it is not necessary to completely acetylate all available basic amino acids in order to eliminate binding to extracellular matrix components.

Binding of step-acetylated Flt1(1-3)-Fc in a Biacore-based assay. Unmodified and step-acetylated Flt1(1-3)-Fc proteins where tested in a Biacore-based assay to evaluate their ability to bind to the Flt1 ligand, VEGF. In this assay, unmodified Flt1(1-3)-Fc protein (0.5, 1.0, or 5.0 μg/ml) was immobilized on the surface of a Biacore chip (see Biacore Instruction Manual, Pharmacia, Inc., Piscataway, N.J., for standard procedures) and a solution containing 0.2 μg/ml VEGF and either unmodified Flt1(1-3)-Fc (at either 0.5, 1.0, or 5.0 μg/ml) or 10 different step-acetylated Flt1(1-3)-Fc samples (at 0.5, 1.0, or 5.0 μg/ml each) were passed over the Flt1(1-3)-Fc-coated chip. At a sub-stoichiometric ratio (0.5 μg/ml of either unmodified Flt1(1-3) or step-acetylated Flt1(1-3)-Fc vs. 0.2 μg/ml VEGF), there is not enough Flt1(1-3)-Fc (either unmodified or step-acetylated) in the solution to completely bind the VEGF. At 1.0 μg/ml, which approximates a 1:1 stoichiometric ratio, both unmodified and step-acetylated Flt1(1-3)-Fc are better able to compete for VEGF binding, but there is still insufficient Flt1(1-3)-Fc protein (either unmodified or step-acetylated) to completely bind the available VEGF. However, at 5.0 μg/ml, which is several times greater than a 1:1 stoichiometric ratio, both the Flt1(1-3)-Fc and the step-acetylated Flt1(1-3)-Fc proteins are able to bind the VEGF, regardless of the degree of acetylation. This clearly demonstrates that acetylation does not alter Flt1(1-3)-Fc's ability to bind VEGF.

Pharmacokinetic analysis of step-acetylated Flt1(1-3)-Fc. In vivo experiments were designed to assess the pharmacokinetic profiles of unmodified Flt1(1-3)-Fc and step-acetylated Flt1(1-3)-Fc protein. Balb/c mice (23-28 g) were injected subcutaneously with 4 mg/kg of unmodified or 10, 20, 40, 60 and 100 fold molar excess samples of step-acetylated Flt1(1-3)-Fc (3 mice for unmodified, 10, 20 and 40 fold molar excess samples and 2 mice for 60 and 100 fold molar excess samples). The mice were tail bled at 1, 2, 4, 6, 24 hours, 2 days and 3 days after injection. The sera were assayed in an ELISA-based assay designed to detect Flt1 (1-3)-Fc (described supra). The Tmax for all of the Flt1(1-3)-Fc proteins tested was at the 6 hour time point but the Cmax was as follows: unmodified Flt1(1-3)-Fc: 0.06 μg/ml; 10 fold molar excess sample: –0.7 μg/ml; 20 fold molar excess sample: 2 μg/ml; 40 fold molar excess sample: 4 μg/ml; 60 fold molar excess sample: 2 μg/ml; 100 fold molar excess sample: 1 μg/ml. This results demonstrates that acetylation or pegylation of Flt1(1-3)-Fc significantly improves its pharmacokinetic profile.

Example 11

Construction of Flt1 (1-3)-Fc Basic Region Deletion Mutant Designated Mut1: Flt1($1\text{-}3_{\Delta B}$)-Fc Based on the observation that acetylated Flt1(1-3)-Fc, which has a pl below 6, has much better pharmacokinetics than the highly positive unmodified Flt1(1-3)-Fc (pl>9.3), it was asked whether the difference in pharmacokinetics could be attributed to the net charge of the protein, which made it stick to negatively charged extracellular matrix components, or whether there were perhaps specific locations on the surface of the Flt1(1-3)-Fc protein that constituted specific binding sites for extracellular matrix components. Referring to the nucleic acid and amino acid sequence of SEQ ID NO:1 and 2, the signal sequence for secretion is located at the beginning of the sequence and extends to the glycine coded for by nucleotides 76-78. The mature protein begins with Ser-Lys-Leu-Lys (SEQ ID NO:35), starting at nucleotide 79 of the nucleic acid sequence. Flt1 Ig domain 1 extends from nucleotide 79 to 393, ending with the amino acids Ser-Asp-Thr. Flt1 Ig domain 2 extends from nucleotide 394 to 687 (encoding Gly-Arg-Pro to Asn-Thr-Ile), and Flt1 Ig domain 3 extends from nucleotides 688 to 996 (encoding Ile-Asp-Val to Asp-Lys-Ala). There is a bridging amino acid sequence, Gly-Pro-Gly, encoded by nucleotides 997-1005, followed by the nucleotide sequence encoding human Fc (nucleotides 1006-1701 or amino acids Glu-Pro-Lys to Pro-Gly-Lys-stop).

A more detailed analysis of the Flt1 amino acid sequence reveals that there is a cluster, namely, amino acid residues 272-281 of SEQ ID NO:2, in which 6 out of 10 amino acid residues are basic. This sequence is located in Flt1 Ig domain 3 of the receptor, which is not itself essential for binding of VEGF ligand, but which confers a higher affinity binding to ligand. An alignment of the sequence of Ig domain 3 with that of Ig domain 2 reveals that in this region, there is very poor alignment between the two Ig domains, and that there are about 10 additional amino acids in Ig domain 3. An analysis of the hydrophilicity profiles (MacVector computer software) of these two domains clearly indicates the presence of a hydrophilic region in the protein. These observations raised the possibility that the actual three dimensional conformation of Flt1 Ig domain 3 allowed for some type of protrusion that is not in Flt1 Ig domain 2. To test this hypothesis, the 10 additional amino acids were deleted and the resulting protein was tested to see whether the deletion would affect the pharmacokinetics favorably without seriously compromising the affinity of the receptor for VEGF. This DNA construct, which was constructed using standard molecular biology techniques in the mammalian expression vector pMT21 (Genetics Institute, Inc., Cambridge, Mass.), is referred to as Mut1: Flt1(1-3$_{AB}$)-Fc. The Mut1: Flt1(1-3$_{AB}$)-Fc construct (SEQ ID NO:3-4) was derived from Flt1(1-3)-Fc by deletion of nucleotides 814-843 of SEQ ID NO:1, which deletes the highly basic 10-amino acid residue sequence from Flt1 Ig domain 3. The final DNA construct was sequence-verified using an ABI 373A DNA sequencer and Taq Dideoxy Terminator Cycle Sequencing Kit (Applied Biosystems, Inc., Foster City, Calif.).

Example 12

Construction of Flt1(1-3)-Fc Basic Region Deletion Mutant Designated Mut2: Flt1(2-3$_{AB)-Fc}$ A second deletion mutant construct, designated Mut2: Flt1(2-3$_{AB}$)-Fc (SEQ ID NO:5-6), was derived from the Mut1: Flt1(1-3$_{AB}$)-Fc construct by deletion of Flt1 Ig domain 1 encoded by nucleotides 79-393 (SEQ ID NO:1); for convenience, nucleotides 73-78 were changed (TCCGGA; SEQ ID NO:26). This introduced a restriction site (BspE1) without altering the associated amino acid sequence, Ser-Gly.

Example 13

Construction of Flt1(1-3)-Fc Deletion Mutant Designated Mut3: Flt1(2-3)-Fc

A third deletion mutate construct, designated Mut3: Flt1(2-3)-Fc (SEQ ID NO:7-8), was constructed the same way as the Mut2: Flt1(2-3$_{AB}$)-Fc construct, except that Flt1 Ig domain 3 was left intact (the basic region amino acids were not deleted).

Example 14

Construction of Flt(1-3)-Fc Basic Region N-Glycosylation Mutant Designated Mut4: Flt1(1-3$_{R->N}$)-Fc A construct was made in which a N-glycosylation site was introduced into the middle of the basic region of Flt1 Ig domain 3. This construct was designated Mut4: Flt1(1-3$_{R->N}$)-Fc (SEQ ID NO:9-10) and was made by changing nucleotides 824-825 of SEQ ID NO:1 from GA to AC, consequently changing the coded Arg residue (AGA) into an Asn residue (AAC). The resulting amino acid sequence is therefore changed from Arg-Ala-Ser to Asn-Ala-Ser, which matches the canonical signal (Asn-Xxx-Ser/Thr) for the addition of a N-glycosylation site at the Asn residue.

Example 15

Figure 2:
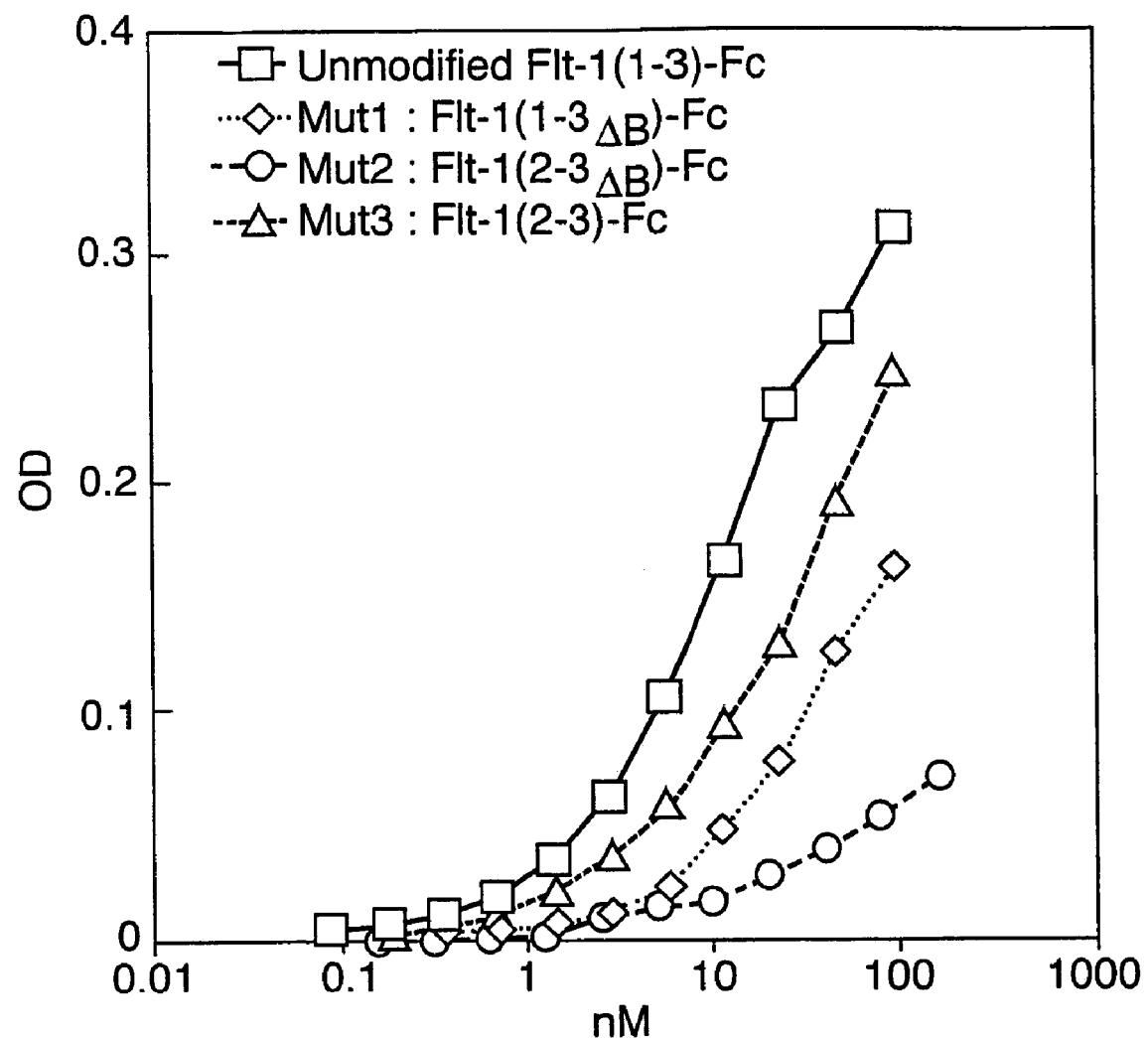
FIG. 2. Binding of unmodified Flt1(1-3)-Fc, Mut1: Flt1(1-3$_{AB}$)-Fc, Mut2: Flt1(2-3$_{AB}$)-Fc, and Flt1(2-3) mutant proteins to Matrigel® coated plates.

Characterization of Acetylated Flt1(1-3)-Fc, Mut1: Flt1(1-3$_{AB}$)-Fc, and Mut4: Flt1(1-3$_{R->N}$)-Fc Mutants Binding to extracellular matrix components. To determine whether the three modified proteins were more or less likely to have improved pharmacokinetic properties, Matrigel coated 96-well dishes were incubated with varying concentrations of the mutant proteins and detected with anti-human Fc/alkaline-phosphatase conjugated antibodies. As shown in FIG. 2, this experiment showed that while the unmodified Flt1(1-3)-Fc protein could bind avidly to these wells, the Mut3: Flt1(2-3)-Fc protein bound somewhat more weakly, the Mut1: Flt1(1-3$_{AB}$)-Fc protein bound more weakly still, and the Mut2: Flt1(2-3$_{AB}$)-Fc protein showed the best profile, binding more weakly than any of the other mutant proteins. The Mut4: Flt1(1-3$_{R->N}$)-Fc glycosylation mutant protein showed only marginal benefit on the Matrigel assay. These results confirm the hypothesis that a linear sequence of positive amino acids can be deleted from the primary sequence resulting in a decrease in charge interaction with extracellular matrix components.

Binding of Mut1 and Mut4 in a Biacore-based assay. Unmodified and acetylated Flt1(1-3)-Fc and genetically modified Mut1: Flt1(1-3$_{AB}$)-Fc and Mut4: Flt1(1-3$_{R->N}$)-Fc proteins where tested in a Biacore-based assay to evaluate their ability to bind to the Flt1 ligand, VEGF. In this assay, unmodified Flt1(1-3)-Fc protein (0.25, 0.5, or 1.0 µg/ml) was immobilized on the surface of a Biacore chip and a solution containing 0.1 µg/ml VEGF and either purified or COS cell supernatant containing unmodified Flt1(1-3)-Fc (at approximately (0.25, 0.5, or 1.0 µg/ml), purified acetylated Flt1(1-3)-Fc (at (0.25, 0.5, or 1.0 µg/ml), COS cell supernatant containing Mut1: Flt1(1-3$_{AB}$)-Fc (at approximately (0.25, 0.5, or 1.0 µg/ml), or COS cell supernatant containing Mut4: Flt1(1-3$_{R->N}$)-Fc (at approximately (0.25, 0.5, or 1.0 µg/ml) were passed over the Flt1(1-3)-Fc-coated chip. As shown in FIG. 1, at the sub-stoichiometric ratio (0.25 µg/ml Flt1(1-3)-Fc of unmodified, acetylated or genetically modified samples vs. 01. µg/ml VEGF), there is insufficient Flt1(1-3)-Fc protein to block binding of VEGF to the Flt1(1-3)-Fc immobilized on the Biacore chip. At 0.5 µg/ml of unmodified, acetylated or genetically modified Flt1(1-3)-Fc proteins, the stoichiometric ratio approximates 1:1 and there is an increased ability to block VEGF binding to the Biacore chip. At 1.0 µg/ml of unmodified, acetylated or genetically modified Flt1(1-3)-Fc proteins, which is approximately a 10:1 stoichiometric ratio, the Flt1(1-3)-Fc proteins are able to block binding of VEGF to the Biacore chip, but they are not equivalent. Unmodified, acetylated, and Mut1: Flt1(1-3$_{AB}$)-Fc are essentially equal in their ability to block VEGF binding, whereas Mut4: Flt1(1-3$_{R->N}$)-Fc is somewhat less efficient at blocking binding. These results confirm the hypothesis that it is possible to reduce the non-specific binding of a positively charged molecule by genetically removing a linear sequence of predominantly negatively charged amino acids.

Figure 3:
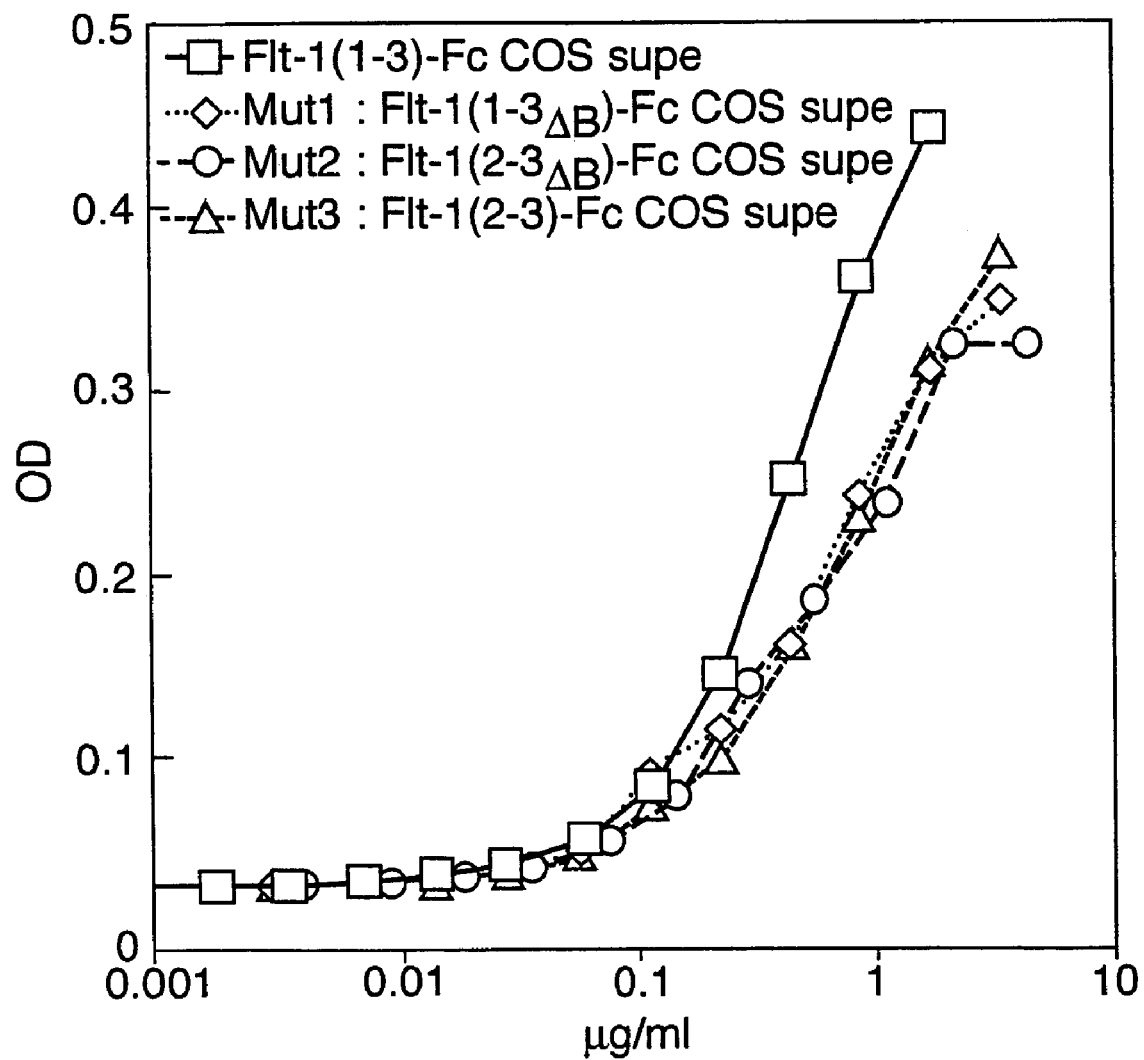
FIG. 3. Binding of unmodified Flt1(1-3)-Fc, Mut1: Flt1(1-3$_{AB}$)-Fc, Mut2: Flt1(2-3$_{AB}$)-Fc, and Flt1(2-3) mutant proteins in an ELISA-based assay.

Binding of Mut1. Mut2 and Mut3 in an ELISA-based assay. To determine whether the three mutant proteins could bind the Flt1 ligand VEGF, binding experiments were done in which 96-well plates coated with VEGF were incubated with varying concentrations of the respective mutant protein, and after washing, the amount bound was detected by incubating with an alkaline phosphatase conjugated anti-human Fc antibody and quantitated colorimetrically by the addition of an appropriate alkaline phosphatase substrate. As shown in FIG. 3, this experiment showed that all the mutant proteins could bind VEGF similarly, at the concentrations tested.

Example 16

Figure 4:
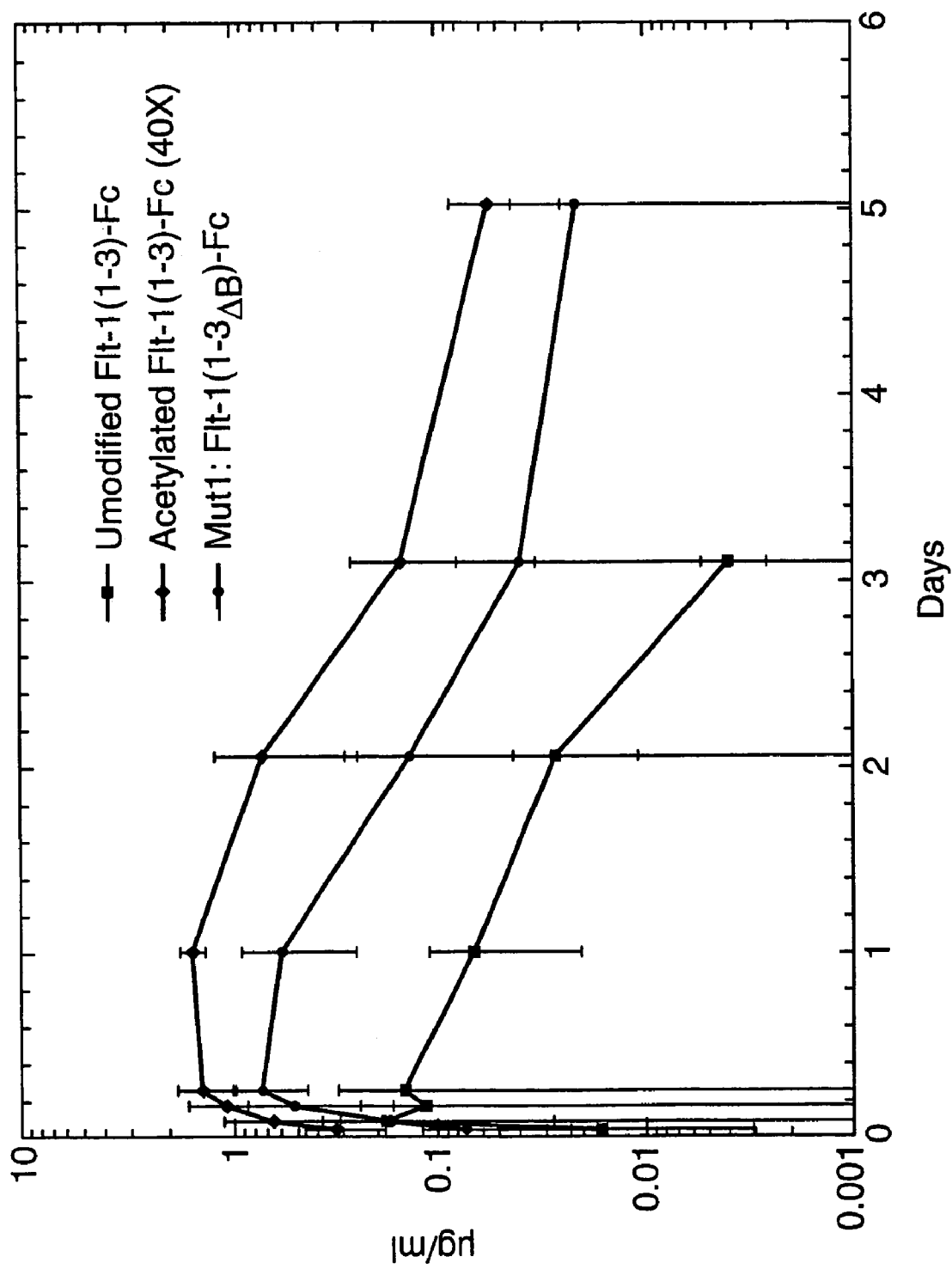
FIG. 4. Pharmacokinetic profiles of unmodified Flt1(1-3)-Fc, Mut1: Flt1(1-3$_{AB}$)-Fc, Mut2: Flt1(2-3$_{AB}$)-Fc, and Flt1(2-3) mutant proteins.

Pharmacokinetic Analysis of Acetylated Flt1(1-3)-Fc, Mut1, and Unmodified Flt1(1-3)-Fc In vivo experiments were designed to assess the pharmacokinetic profiles of unmodified Flt1(1-3)-Fc, Mut1: Flt1(1-$3_{AB}$)-Fc, and 40 fold molar excess acetylated Flt1(1-3)-Fc protein. Balb/c mice (25-30 g) were injected subcutaneously with 4 mg/kg of unmodified Flt1(1-3)-Fc, 40 fold molar excess acetylated Flt1(1-3)-Fc, and Mut1: Flt1(1-$3_{AB}$)-Fc proteins (4 mice each). These mice were tail bled at 1, 2, 4, 6, 24 hours, 2 days, 3 days, and 5 days after injection. The sera were assayed in an ELISA designed to detect Flt1(1-3)-Fc protein which involves coating an ELISA plate with VEGF, binding the Flt1(1-3)-Fc and reporting with an anti-Fc antibody linked to alkaline phosphatase. As shown in FIG. 4, the Cmax for these reagents was as follows: Unmodified Flt1(1-3)-Fc -0.15 μg/ml; 40 fold molar excess acetylated Flt1(1-3)-Fc—1.5 μg/ml; and Mut1: Flt1(1-$3_{AB}$)-Fc—0.7 μg/ml.

Example 17

Modified Flt1 Receptor Vector Construction

Chimeric molecules were constructed, denoted R1R2 (Flt1. D2. Flk1D3. FcΔC1(a) and VEGFR1R2-FcΔC1(a) and R1R3(Flt1D2. VEGFR3D3-FcΔC1(a) and VEGFR1R3-FcΔC1(a) respectively, wherein R1 and Flt1D2=Ig domain 2 of Flt1 (VEGFR1); R2 and Flk1D3=Ig domain 3 of Flk1 (VEGFR2); and R3 and VEGFR3D3=Ig domain 3 of Flt4 (VEGFR3)) were much less sticky to ECM, as judged by an in vitro ECM binding assay and had greatly improved PK as described herein. In addition, these molecules were able to bind VEGF tightly and block phosphorylation of the native Flk1 receptor expressed in endothelial cells.

Construction of the expression plasmid pFlt1D2. Flk1D3. FcΔC1(a). Expression plasmids pMT21. Flt1(1-3).Fc (6519 bp) and pMT21. Flk-1(1-3).Fc (5230 bp) are plasmids that encode ampicillin resistance and Fc-tagged versions of Ig domains 1-3 of human Flt1 and human Flk1, respectively. These plasmids were used to construct a DNA fragment consisting of a fusion of Ig domain 2 of Flt1 with Ig domain 3 of Flk1, using PCR amplification of the respective Ig domains followed by further rounds of PCR to achieve fusion of the two domains into a single fragment. For Ig domain 2 of Flt1, the 5' and 3' amplification primers were as follows: 5': bsp/flt1D2 (5'-GACTAGCAGTCCGG-AGG-TAGACCTTTCGTAGAGATG-3') (SEQ ID NO:18), 3': Flt1D2-Flk1D3. as (5'-CGGACTCAGAACCACATCTAT-GATTGTATTGGT-3') (SEQ ID NO:19). The 5' amplification primer encodes a BspE1 restriction enzyme site upstream of Ig domain 2 of Flt1, defined by the amino acid sequence GRPFVEM (SEQ ID NO:20) corresponding to amino acids 27-33 of SEQ ID NO:12. The 3' primer encodes the reverse complement of the 3' end of Flt1 Ig domain 2 fused directly to the 5' beginning of Flk1 Ig domain 3, with the fusion point defined as TIID of Flt1 (corresponding to amino acids 123-126 of SEQ ID NO:12) and continuing into VVLS (SEQ ID NO:17) (corresponding to amino acids 127-130 of SEQ ID NO:12) of Flk1.

For Ig domain 3 of Flk1, the 5' and 3' amplification primers were as follows:5': Flt1D2-Flk1D3. s (5=-ACAAT-CATAGATGTGGTTCTGAGTCCGTCTCATGG-3') (SEQ ID NO:21); 3': Flk1D3/apa/srf.as (5'-GATAATGC-CCGGGCCCTTTTCATGGACCCTGACAAATG-3') (SEQ ID NO:22). The 5' amplification primer encodes the end of Flt1 Ig domain 2 fused directly to the beginning of Flk1 Ig domain 3, as described above. The 3' amplification primer encodes the end of Flk1 Ig domain 3, defined by the amino acids VRVHEK (SEQ ID NO:23) (corresponding to amino acids 223-228 of SEQ ID NO:12), followed by a bridging sequence that includes a recognition sequence for the restriction enzyme Srfl, and encodes the amino acids GPG. The bridging sequence corresponds to amino acids 229-231 of SEQ ID NO:12.

After a round of PCR amplification to produce the individual domains, the products were combined in a tube and subjected to a further round of PCR with the primers bsp/flt1D2 and Flk1D3/apa/srf.as (described supra) to produce the fusion product. This PCR product was subsequently digested with the restriction enzymes BspEI and SmaI and the resulting 614 bp fragment was subcloned into the BspEI to Srfl restriction sites of the vector pMT21/ΔB2. Fc, to create the plasmid pMT21/Flt1D2. Flk1D3. Fc. The nucleotide sequence of the Flt1D2-Flk1D3 gene fusion insert was verified by standard sequence analysis. This plasmid was then digested with the restriction enzymes EcoRI and Srfl and the resulting 702 bp fragment was transferred into the EcoRI to Srfl restriction sites of the plasmid pFlt1(1-3)B2-FcΔC1(a) to produce the plasmid pFlt1D2. Flk1D3. FcΔC1 (a). The complete DNA and deduced amino acid sequences of the Flt1D2. Flk1D3. FcΔC1(a) chimeric molecule is shown in SEQ ID NO:11-12.

Construction of the expression plasmid pFlt1D2VEGFR3D3FcΔC1(a). The expression plasmid pMT21. Flt1(1-3).Fc (6519 bp) encodes ampicillin resistance and an Fc-tagged version of Ig domains 1-3 of human Flt1 receptor. This plasmid was used to produce a DNA fragment containing Ig domain 2 of Flt1 by PCR. RNA from the cell line HEL921.7 was used to produce Ig domain 3 of Flk1, using standard RT-PCR methodology. A further round of PCR amplification was used to achieve fusion of the two Ig domains into a single fused fragment. For Ig domain 2 of Flt1, the 5' and 3' amplification primers were as follows: 5': bsp/flt1D2 (5'-GACTAGCAGTCCGGAGGTAGAC-CTTTCGTAGAGATG-3') (SEQ ID NO:24), 3': Flt1D2. VEGFR3D3. as(TTCCTGGGCAACAGCTGGATATCTAT-GATTGTATTGGT) (SEQ ID NO:25). The 5' amplification primer encodes a BspE1 restriction site upstream of Ig domain 2 of Flt1, defined by the amino acid sequence GRPFVEM (SEQ ID NO:20) (corresponding to amino acids 27-33 of SEQ ID NO:11-12). The 3' amplification primer encodes the reverse complement of the end of Flt1 Ig domain 2 fused directly to the beginning of VEGFR3 Ig domain 3, with the fusion point defined as TIID of Flt1 (corresponding to amino acids 123-126 of SEQ ID NO:14) and continuing into IQLL of VEGFR3 (corresponding to amino acids 127-130 of SEQ ID NO:14).

For Ig domain 3 of VEGFR3, the 5' and 3' primers used for RT-PCR were as follows: 5': R3D3. s (ATCCAGCTGT-TGCCCAGGAAGTCGCTGGAGCTGCTGGTA) (SEQ ID NO:27), 3': R3D3. as (ATTTTCATGCACAATGACCTCG-GTGCTCTCCCGAAATCG) (SEQ ID NO:28). Both the 5' and 3' amplification primers match the sequence of VEGFR3. The 296 bp amplification product of this RT-PCR reaction was isolated by standard techniques and subjected to a second round of PCR to add suitable sequences to allow for fusion of the Flt1D2 with the Flk1D3 domains and fusion of the Flk1D3 and Fc domains via a GPG bridge (see below). The amplification primers were as follows: 5': Flt1D2. VEGFR3D3. s(TCATAGATATCCAGCTGTTGCCCAG-GAAGTCGCTGGAG) (SEQ ID NO:29), 3': VEGFR3D3/srf.as (GATAATGCCCGGGCCATTTTCATGCA-CAATGACCTCGGT) (SEQ ID NO:30). The 5' amplification primer encodes the 3' end of Flt1 Ig domain 2 fused directly to the beginning (5' end) of VEGFR3 Ig domain 3, as described above. The 3' amplification primer encodes the 3' end of VEGFR3 Ig domain 3, defined by the amino acids VIVHEN (SEQ ID NO:31) (corresponding to amino acids 221-226 of SEQ ID NO:14), followed by a bridging sequence that includes a recognition sequence for Srf1, and encodes the amino acids GPG. The bridging sequence corresponds to amino acids 227-229 of SEQ ID NO:14.

After one round (for Flt1 Ig domain 2) or two rounds (for Flt4 Ig domain 3) of PCR to produce the individual Ig domains, the PCR products were combined in a tube and subjected to a further round of PCR amplification with the amplification primers bsp/flt1D2 and VEGFR3D3/srf.as described supra, to produce the fusion product. This PCR product was subsequently digested with the restriction enzymes BspEI and SmaI and the resulting 625 bp fragment was subcloned into the BspEI to SrfI restriction sites of the vector pMT21/Flt1ΔB2. Fc (described supra), to create the plasmid pMT21/Flt1D2. VEGFR3D3. Fc. The sequence of the Flt1D2-VEGFR3D3 gene fusion insert was verified by standard sequence analysis. This plasmid was then digested with the restriction enzymes EcoRI and SrfI and the resulting 693 bp fragment was subcloned into the EcoRI to SrfI restriction sites of the plasmid pFlt1(1-3)ΔB2-FcΔC1(a) to produce the plasmid designated pFlt1D2. VEGFR3D3. FcΔC1(a). The complete DNA deduced amino acid sequence of the Flt1D2. VEGFR3D3. FcΔC1(a) chimeric molecule is shown in SEQ ID NO:13-14.

Example 18

Extracellular Matrix Binding (ECM) Binding Assay

Figure 5:
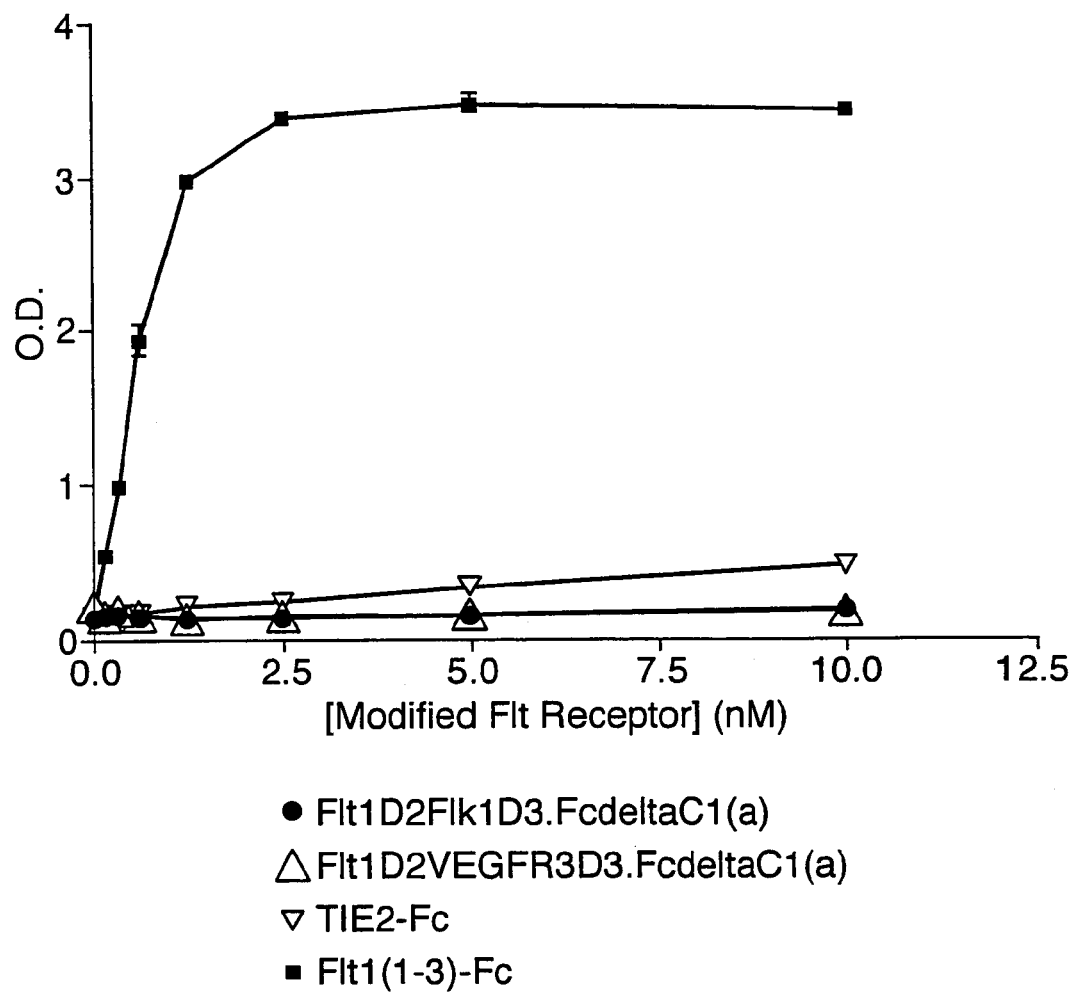
FIG. 5. Extra cellular matrix (ECM) assay of Flt1D2. Flk1D3. FcΔC1(a) and Flt1D2. VEGFR3D3. FcΔC1(a).

ECM-coated plates (Becton Dickinson catalog #35-4607) were rehydrated with warm DME supplemented with glutamine (2 mM), 100 U penicillin, 100 U streptomycin, and 10% BCS for at least 1 hr. before adding samples. The plates were then incubated for 1 hr. at room temperature with varying concentrations of Flt1D2. Flk1D3. FcΔC1(a) and Flt1D2. VEGFR3D3. FcΔC1(a) starting at 10 nM with subsequent 2-fold dilutions in PBS plus 10% BCS. The plates were then washed 3 times with PBS plus 0.1% Triton-X and incubated with alkaline phosphatase-conjugated anti-human Fc antibody (Promega, 1:4000 in PBS plus 10% BCS) for 1 hr. at room temperature. The plates were then washed 4 times with PBS 0.1% Triton-X and alkaline phosphatase buffer/pNPP solution (Sigma) was added for color development. Plates were read at I=405-570 nm. The results of this experiment are shown in FIG. 5 and demonstrate that the Flt1D2. Flk1D3. FcΔC1(a) and Flt1D2. VEGFR3D3. FcΔC1(a) proteins are considerably less sticky to the ECM as compared to the Flt1(1-3)-Fc protein.

Example 19

Transient Expression of pFlt1D2. Flk1D3. FcΔC1(a) in CHO-K1 (E1A) Cells

A large scale (2 L) culture of *E. coli* DH10B cells carrying the pFlt1D2. Flk1D3. FcΔC1(a) plasmid described supra in Example 17(a) was grown overnight in Terrific Broth (TB) plus 100 µg/ml ampicillin. The next day, the plasmid DNA was extracted using a QIAgen Endofree Megaprep kit following the manufacturer's protocol. The concentration of the purified plasmid DNA was determined by standard techniques using a UV spectrophotometer and fluorometer. The plasmid DNA was verified by standard restriction enzyme digestion of aliquots using the restriction enzymes EcoRI plus NotI and AseI. All restriction enzyme digest fragments corresponded to the predicted sizes when analyzed on a 1% agarose gel.

Forty 15 cm petri plates were seeded with CHO-K1/E1A cells at a density of 4×106 cells/plate. Plating media was Gibco Ham's F-12 supplemented with 10% Hyclone Fetal Bovine Serum (FBS), 100 U penicillin/100 U streptomycin and glutamine (2 mM). The following day each plate of cells was transfected with 6 µg of the pFlt1D2. Flk1D3. FcΔC1(a) plasmid DNA using Gibco Optimem and Gibco Lipofectamine in 12 ml volume, following the manufacturer's protocol. Four hours after adding the transfection mix to the cells, 12 ml/plate of Optimem supplemented with 10% FBS was added. Plates were incubated at 37° C. in a 5% $CO_2$ incubator overnight. The following day the media was removed from each plate and 25 ml expression media (Gibco CHO-S-SFM II supplemented with glutamine (2 mM) and 1 mM sodium butyrate) was added. The plates were incubated at 37° C. for 3 days. After 3 days of incubation, the media was aspirated from each plate and centrifuged at 400 rpm in a swinging bucket rotor to pellet cells. The supernatant was decanted into sterile 1 L bottles and purification of the expressed protein was performed as described infra.

Example 20

Construction pVEGFR1R2-FcΔC1(a) Expression Vector

The pVEGFR1R2. FcΔC1(a) (SEQ ID NO:15-16) expression plasmid was constructed by insertion of DNA encoding amino acids SDT (corresponding to amino acids 27-29 of SEQ ID NO:16) between Flt1d2-Flk1d3-FcΔC1(a) amino acids 26 and 27 of SEQ ID NO:12 (GG) and removal of DNA encoding amino acids GPG corresponding to amino acids 229-231. The SDT amino acid sequence is native to the Flt1 receptor and was added back in to decrease the likelihood of heterogeneous N-terminal processing. The GPG (bridging sequence) was removed so that the Flt1 and Flk1 Ig domains were fused directly to one another. The complete DNA and deduced amino acid sequences of the pVEGFR1R2. FcΔC1(a) chimeric molecule is shown in SEQ ID NO:15-16.

Example 21

Cell Culture Process Used to Produce Modified Flt1 Receptors

Cell Culture Process Used to Produce Flt1D2. Flk1D3. FcΔC1(a). The process for production of Flt1D2. Flk1D3.

FcΔC1(a) protein using the expression plasmid pFlt1D2. Flk1D3.FcΔC1(a) described supra in Example 1 involves suspension culture of recombinant Chinese hamster ovary (CHO K1/E1A) cells which constitutively express the protein product. The cells are grown in bioreactors and the protein product is isolated and purified by affinity and size exclusion chromatography.

Cell Expansion. Two confluent T-225 cm² flasks containing the Flt1 D2. Flk1D3. FcΔC1(a) expressing cell line were expanded by passaging cells into eight T-225 cm² flasks in medium (GMEM+10% serum, GIBCO) and incubated at 37° C. and 5% $CO_2$. When the flasks approached confluence (approximately 3 to 4 days) the cells were detached using trypsin. Fresh medium was added to protect the cells from further exposure to the trypsin. The cells were centrifuged and resuspended in fresh medium then transferred to eight 850 cm² roller bottles and incubated at 37° C. and 5% $CO_2$ until confluent.

Suspension Culture in Bioreactors. Cells grown in roller bottles were trypsinized to detach them from the surface and washed with suspension culture medium. The cells are aseptically transferred to a 5 L bioreactor (New Brunswick Celligen Plus) where the cells are grown in 3.5 L of suspension culture. The suspension culture medium was a glutamine-free low glucose modification of IS-CHO (Irvine Scientific) to which 5% fetal bovine serum (Hyclone), GS supplement (Life Technologies) and 25 μM methionine sulfoximine (Sigma) was added. The pH was controlled at 7.2 by addition of carbon dioxide to the inlet gas or by addition of a liquid solution of sodium carbonate to the bioreactor. Dissolved oxygen level was maintained at 30% of saturation by addition of oxygen or nitrogen to the inlet gas and temperature controlled at 37° C. When a density of $4 \times 10^6$ cells/mL was reached the cells were transferred to a 40 L bioreactor containing the same medium and setpoints for controlling the bioreactor. The temperature setpoint was reduced to 34° C. to slow cell growth and increase the relative rate of protein expression.

Cell Culture Process Used to Produce Flt1D2. VEGFR3D3. FcΔC1(a). The same methodologies as described supra for Flt1D2. Flk1D3. FcΔC1(a) were used to produce Flt1D2. VEGFR3D3. FcΔC1(a).

Example 22

Harvest and Purification of Modified Flt1 Receptors

Harvest and Purification of Flt1D2. Flk1D3. FcΔC1(a). The product protein was aseptically harvested from the bioreactor while retaining cells using Millipore Prostak tangential-flow filtration modules and a low-shear mechanical pump (Fristam). Fresh medium was added to the bioreactor to replace that removed during the harvest filtration. Approximately 40 L of harvest filtrate was then loaded onto a 400 mL column containing Protein A Sepharose resin (Amersham Pharmacia). After loading the resin was washed with buffer containing 10 mM sodium phosphate, 500 mM sodium chloride, pH 7.2 to remove any unbound contaminating proteins. Flt1D2. Flk1D3. FcΔC1(a) protein was eluted with a pH 3.0 citrate buffer. The eluted protein was neutralized by addition of Tris base and frozen at −20° C.

Several frozen lots of Flt1D2. Flk1D3. FcΔC1(a) protein from the Protein A step above were thawed, pooled and concentrated using a Millipore 30 kD nominal molecular weight cutoff (NMWCO) tangential flow filtration membrane. The protein was transferred to a stirred cell concentrator (Millipore) and further concentrated to 30 mg/mL using a 30 kD NMWCO membrane. The concentrated protein was loaded onto a size exclusion column packed with Superdex 200 resin (Amersham Pharmacia) that was equilibrated with phosphate buffered saline plus 5% glycerol. The same buffer was used to run the column. The fractions corresponding to Flt1D2. Flk1D3. FcΔC1(a) dimer were pooled, sterile filtered through a 0.22 micron filter, aliquoted and frozen.

Harvest and Purification of Flt1D2. VEGFR3D3. FcΔC1 (a). The same methodologies as described supra for Flt1D2. Flk1D3. FcΔC1(a) were used to harvest and purify Flt1D2. VEGFR3D3. FcΔC1(a).

Example 23

Phosphorylation Assay for Transiently Expressed VEGFR2

Primary human umbilical vein endothelial cells (HU-VECs), passage 4-6, were starved for 2 hrs in serum-free DME high glucose media. Samples containing 40 ng/ml (1 nM) human VEGF165, which is a ligand for the VEGF receptors Flt1, Flk1 and Flt4(VEGFR3) were prepared and were preincubated for 1 hr. at room temperature with varying amounts of the modified Flt1 receptors Flt1(1-3)-Fc, Flt1(1-3)-Fc (A40), Flt1D2Flk1D3. FcΔC1(a) and Flt1D2VEGFR3D3. FcΔC1(a) in serum-free DME-high glucose media containing 0.1% BSA. Cells were challenged for 5 minutes with the samples prepared above +/−VEGF165, followed by whole cell lysis using complete lysis buffer. Cell lysates were immunoprecipitated with an antibody directed against the C-terminus of VEGFR2 receptor. The immunoprecipitated lysates were loaded onto 4-12% SDS-PAGE Novex gel and then transferred to PVDF membrane using standard transfer methodologies. Detection of phosphorylated VEGFR2 was done by immunoblotting with the anti-phospho Tyrosine mAb called 4G10 (UBI) and developed using ECL-reagent (Amersham). Detection by Western blot of tyrosine phosphorylated VEGFR2(Flk1) by VEGF165 ligand stimulation shows that cell-surface receptors are phosphorylated to varying levels depending on which modified Flt1receptor is used during the preincubations with VEGF. At a 1.5 molar excess of either Flt1(1-3)-Fc, Flt1(1-3)-Fc (A40) or transient Flt1D2Flk1D3. FcΔC1 (a) there is complete blockage of receptor stimulation by these three modified Flt1 receptors as compared to control media challenge. In contrast, transient Flt1D2VEGFR3D3. FcΔC1(a) does not show significant blockage at this molar excess, as compared with VEGF positive control challenge. Where the modified Flt receptors are in a 3-fold molar excess to VEGF165 ligand and modified Flt1 receptors are in a 6-fold molar excess to VEGF165 ligand, transient Flt1D2VEGFR3D3. FcΔC1(a) can now be shown to be partially blocking VEGF165-induced stimulation of cell-surface receptors.

Detection by Western blot of tyrosine phosphorylated VEGFR2(Flk1) by VEGF165 ligand stimulation shows that cell-surface receptors are not phosphorylated by challenge samples which have VEGF165 preincubated with 1 and 2 fold molar excess or 3 and 4 fold molar excess of either transient Flt1D2Flk1D3FcΔC1(a), stable Flt1D2Flk1D3FcΔC1(a), or transient VEGFR1R2-FcΔC1 (a). At all modified Flt1 receptor concentrations tested there is complete binding of VEGF165 ligand during the preincubation, resulting in no detectable stimulation of cell-surface receptors by unbound VEGF165 as compared to control media challenge.

Example 24

Cell Proliferation Bioassay

The test cell population is MG87 cells that have been stably transfected with a expression plasmid that contains a DNA insert encoding the VEGFR2(Flk1) extracellular domain fused to the TrkB intracellular kinase domain, thus producing a chimeric molecule. The reason the TrkB intracellular kinase domain was used rather than the native VEGFR2(Flk1) intracellular kinase domain is that the intracellular kinase domain of VEGFR2(Flk1) does not cause a strong proliferative response when stimulated by VEGF165 in these cells. It is known that MG87 cells containing full length TrkB receptor give a robust proliferative response when stimulated with BDNF, so the TrkB intracellular kinase domain was engineered to replace the intracellular kinase domain of VEGFR2(Flk1) to take advantage of this proliferative response capability.

Figure 6:
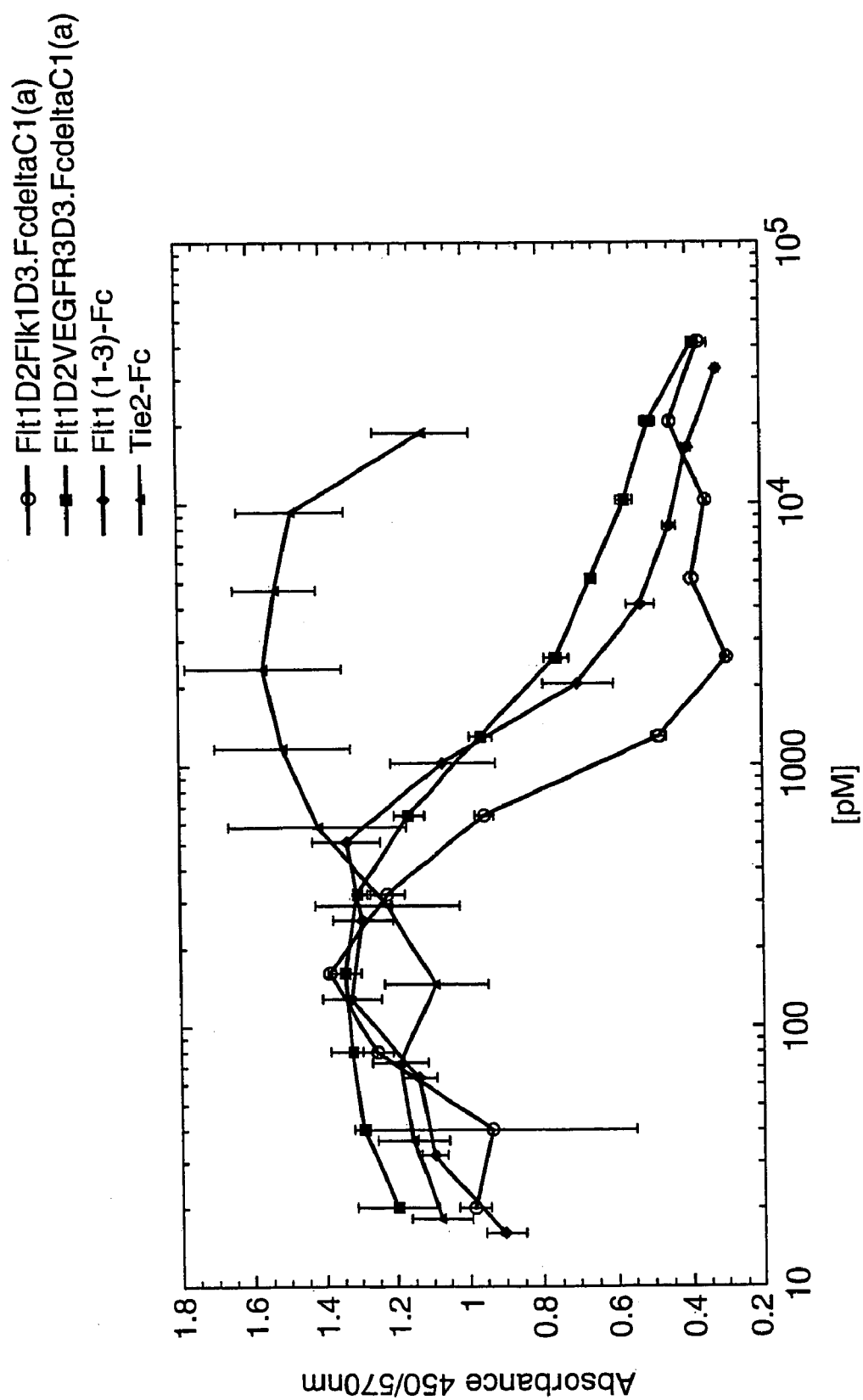
FIG. 6. MG/R2 Cell proliferation assay. Modified Flt receptors Flt1(1-3)-Fc, Flt1D2. Flk1D3. FcΔC1(a) and Flt1D2. VEGFR3D3. FcΔC1(a), plus an irrelevant receptor termed Tie2-Fc as a negative control, were titrated from 40 nM to 20 pM and incubated on the cells for 1 hr at 37° C.

$5 \times 10^3$ cells/well were plated in a 96 well plate and allowed to settle for 2 hrs at 37° C. The following modified Flt receptors Flt1(1-3)-Fc, Flt1D2Flk1D3FcΔC1(a) and Flt1D2. VEGFR3D3. FcΔC1(a), plus an irrelevant receptor termed Tie2-Fc as a negative control, were titrated from 40 nM to 20 pM and incubated on the cells for 1 hr at 37° C. Human recombinant VEGF165 in defined media was then added to all the wells at a concentration of 1.56 nM. The plates were incubated for 72 hrs at 37° C. and then MTS (Owen's reagent, Promega) added and the plates were incubated for an additional for 4 hrs. Finally, the plates were read on a spectrophotometer at 450/570 nm. The results of this experiment are shown in FIG. 6. The control receptor Tie2-Fc does not block VEGF165-induced cell proliferation at any concentration whereas Flt1D2. Flk1D3. FcΔC1(a) blocks 1.56 nM VEGF165 with a half maximal dose of 0.8 nM. Flt1(1-3)-Fc and Flt1D2. VEGFR3D3. FcΔC1(a) are less effective in blocking VEGF165 in this assay with a half maximal dose of ~2 nM. VEGF165 alone gives a reading of 1.2 absorbance units and the background is 0.38 absorbance units.

Example 25

Binding Stoichiometry of Modified Flt Receptors to VEGF165

BIAcore Analysis. The stoichiometry of Flt1D2Flk1D3. FcΔC1(a) and VEGFR1R2-FcΔC1(a) interaction with human VEGF165 was determined by measuring either the level of VEGF saturation binding to the Flt1D2Flk1D3. FcΔC1(a) or VEGFR1R2-FcΔC1(a) surfaces or measuring concentration of VEGF165 needed to completely prevent binding of Flt1D2Flk1D3. FcΔC1(a) or VEGFR1R2-FcΔC1 (a) to VEGF BIAcore chip surface.

Modified Flt receptors Flt1D2Flk1D3. FcΔC1(a) and VEGFR1R2-FcΔC1(a), were captured with an anti-Fc specific antibody that was first immobilized on a Biacore chip (BIACORE) using amine-coupling chemistry. A blank antibody surface was used as a negative control. VEGF165 was injected at a concentration of 1 nM, 10 nM, and 50 nM over the Flt1D2Flk1D3. FcΔC1(a) and VEGFR1R2-FcΔC1(a) surfaces at 10 μl/min for one hour. A real-time binding signal was recorded and saturation binding was achieved at the end of each injection. Binding stoichiometry was calculated as a molar ratio of bound VEGF165 to the immobilized Flt1D2Flk1D3. FcΔC1(a) or VEGFR1R2-FcΔC1(a), using the conversion factor of 1000 RU equivalent to 1 ng/ml. The results indicated binding stoichiometry of one VEGF165 dimeric molecule per one Flt1D2Flk1D3. FcΔC1(a) or VEGFR1R2-FcΔC1(a) molecule (FIG. 7).

In solution, Flt1D2Flk1D3. FcΔC1(a) or VEGFR1R2-FcΔC1(a) at a concentration of 1 nM (estimated to be 1000 times higher than the KD of the Flt1D2Flk1D3. FcΔC1(a) or VEGFR1R2-FcΔC1(a)/VEGF165 interaction) were mixed with varied concentrations of VEGF165. After one hour incubation, concentrations of the free Flt1D2Flk1D3. FcΔC1(a) in solution were measured as a binding signal to an amine-coupled VEGF165 surface. A calibration curve was used to convert the Flt1D2Flk1D3. FcΔC1(a) BIAcore binding signal to its molar concentration. The data showed that the addition of 1 nM VEGF165 into the Flt1D2Flk1D3. FcΔC1(a) solution completely blocked Flt1D2Flk1D3. FcΔC1(a) binding to the VEGF165 surface. This result suggested the binding stoichiometry of one VEGF165 molecule per one Flt1D2Flk1D3. FcΔC1(a) molecule. When the concentration of Flt1D2Flk1D3. FcΔC1(a) was plotted as a function of added concentration of VEGF165, the slope of the linear portion was −1.06 for Flt1D2Flk1D3. FcΔC1(a) and −1.07 for VEGFR1R2-FcΔC1(a). The magnitude of the slope, very close to negative one, was indicative that one molecule of VEGF165 bound to one molecule of either Flt1D2Flk1D3. FcΔC1(a) or VEGFR1R2-FcΔC1(a).

Size Exclusion Chromatography. Flt1D2Flk1D3. FcΔC1(a) was mixed with a 3-fold excess of VEGF165 and the receptor-ligand complex was purified using a Pharmacia Superose 6 size exclusion chromatography column. The receptor-ligand complex was then incubated in a buffer containing 6M guanidine hydrochloride in order to dissociate it into its component proteins. Flt1D2Flk1D3. FcΔC1(a) was separated from VEGF165 using Superose 6 size exclusion chromatography column run in 6M guanidium chloride. In order to determine complex stoichiometry, several injections of Flt1D2Flk1D3. FcΔC1(a) and VEGF165 were made and peak height or peak integrated intensity was plotted as a function of the concentration of injected protein. The calibration was done under condition identical to one used in separating components of Flt1D2Flk1D3. FcΔC1(a)/VEGF complex. Quantification of the Flt1D2Flk1D3. FcΔC1(a)/VEGF complex composition was based on the calibration curves. The results of this experiment (FIG. 7) shows the ratio of VEGF165 to Flt1D2Flk1D3. FcΔC1(a) in a complex to be 1:1.

Example 26

Determination of the Binding Stoichiometry of Flt1D2Flk1D3. FcΔC1(a)/VEGF165 Complex by Size Exclusion Chromatography Flt1D2Flk1D3. FcΔC1(a)/VEGF165 Complex Preparation. VEGF165 (concentration=3.61 mg/ml) was mixed with CHO cell transiently expressed Flt1D2. Flk1D3. FcΔC1(a) (concentration=0.9 mg/ml) in molar ratio of 3:1 (VEGF165:Flt1D2. Flk1D3. FcΔC1(a)) and incubated overnight at 4° C.

Size Exclusion Chromatography (SEC) under native conditions. To separate the complex from excess of unbound VEGF165, 50 μl of the complex was loaded on a Pharmacia Superose 12 PC 3.2/30 which was equilibrated in PBS buffer. The sample was eluted with the same buffer at flow rate 40 μl/min. at room temperature. Peak #1 represents the complex and peak #2 represents unbound VEGF165. Fractions eluted between 1.1 and 1.2 ml were combined and guanidinium hydrochloride (GuHCl) was added to a final concentration 4.5M to dissociate the complex.

Size Exclusion Chromatography (SEC) under dissociative conditions. To separate the components of the receptor-ligand complex and to determine their molar ratio, 50 µl of dissociated complex as described supra was loaded onto a Superose 12 PC 3.2/30 equilibrated in 6M GuHCl and eluted with the same solution at a flow rate 40 µl/min. at room temperature.

Calculation of Flt1D2Flk1D3. FcΔC1(a):VEGF165 Complex Stoichiometry. The stoichiometry of the receptor-ligand complex was determined from the peak area or the peak height of the components. Concentrations of VEGF165 and Flt1D2Flk1D3. FcΔC1(a) corresponding to the peak height or peak area, respectively, were obtained from the standard curves for VEGF165 and Flt1D2Flk1D3. FcΔC1(a). To obtain a standard curve, four different concentrations (0.04 mg/ml –0.3 mg/ml) of either component were injected onto a Pharmacia Superose 12 PC 3.2/30 column equilibrated in 6M guanidinium chloride and eluted with the same solution at flow rate 40 µl/min. at room temperature. The standard curve was obtained by plotting peak area or peak height vs protein concentration. The molar ratio of VEGF165: Flt1D2Flk1D3. FcΔC1(a) determined from the peak area of the components was 1.16. The molar ratio of VEGF165: Flt1D2Flk1D3. FcΔC1(a) determined from the peak height of the components was 1.10.

Example 27

Determination of the Stoichiometry of the Flt1D2Flk1D3. FcΔC1(a)/VEGF165 Complex by Size Exclusion Chromatography with On-Line Light Scattering Complex preparation. VEGF165 was mixed with CHO transiently expressed Flt1D2. Flk1D3. FcΔC1(a) protein in molar ratio of 3:1 (VEGF165:Flt1D2Flk1D3. FcΔC1(a)) and incubated overnight at 4° C.

Size Exclusion Chromatography (SEC) with On-Line Light Scattering. Size exclusion chromatography column with a MiniDawn on-line light scattering detector (Wyatt Technology, Santa Barbara, Calif.) and refractive index (RI) detectors (Shimadzu, Kyoto, Japan) was used to determine the molecular weight (MW) of the receptor-ligand complex. Samples were injected onto a Superose 12 HR 10/30 column (Pharmacia) equilibrated in PBS buffer and eluted with the same buffer at flow rate 0.5 ml/min. at room temperature. The elution profile shows two peaks. Peak #1 represents the receptor-ligand complex and peak #2 represents the unbound VEGF165. MW was calculated from LS and RI signals. The same procedure was used to determine MW of the individual components of the receptor-ligand complex. The results of these determinations are as follows: MW of the Flt1D2Flk1D3. FcΔC1(a)/VEGF165 complex at the peak position is 157 300, the MW of VEGF165 at the peak position is 44 390 and the MW of R1R2 at the peak is 113 300.

These data indicated that the stoichiometry of the Flt1D2Flk1D3. FcΔC1(a)/VEGF complex is 1:1 as its corresponds to the sum of molecular weights for Flt1D2Flk1D3. FcΔC1(a) and VEGF165. Importantly, this method conclusively proved that the Flt1D2Flk1D3. FcΔC1 (a)/VEGF165 complex was indeed composed of only one molecule of VEGF165 ligand and only one molecule of the Flt1D2Flk1D3. FcΔC1(a).

Example 28

Peptide Mapping of Flt1D2. Flk1D3. FcΔC1(a)

The disulfide structures and glycosylation sites in Flt1D2. Flk1D3. FcΔC1(a) were determined by a peptide mapping method. In this method, the protein was first cleaved with trypsin. Tryptic fragments were analyzed and identified by HPLC coupled with mass spectrometry, in addition to an N-terminal sequencing technique. Reduction of the tryptic digest was employed to help identify disulfide-bond-containing fragments. Treatment of the tryptic digest with PNGase F (Glyko, Novato, Calif.) was employed to help identify fragments with N-linked glycosylation sites.

There are a total of ten cysteines in Flt1D2. Flk1D3. FcΔC1(a); six of them belong to the Fc region. Cys27 has-been confirmed to be disulfide bonded to Cys76. Cys121 is confirmed to be disulfide bonded to Cys 182. The first two cysteines in the Fc region (Cys211 and Cys214) form an intermolecular disulfide bond with the same two cysteines in another Fc chain. However, because these two cysteines can not be separated enzymatically from each other, it can not be determined whether disulfide bonding is occurring between same cysteines (Cys211 to Cys211, for example) or between Cys211 and Cys214. Cys216 is confirmed to be disulfide bonded to Cys306. Cys 352 is confirmed to be disulfide bonded to Cys410.

There are five possible N-linked glycosylation sites in Flt1D2. Flk1D3. FcΔC1(a). All five of them are found to be glycosylated to varying degrees. Complete glycosylation was observed at Asn33 (amino acid sequence NIT), Asn193 (amino acid sequence NST), and Asn282 (amino acid sequence NST). In addition, partial glycosylation is observed on Asn65 and Asn120.

Example 29

Pharmacokinetic Analysis of Modified Flt Receptors

Figure 8:
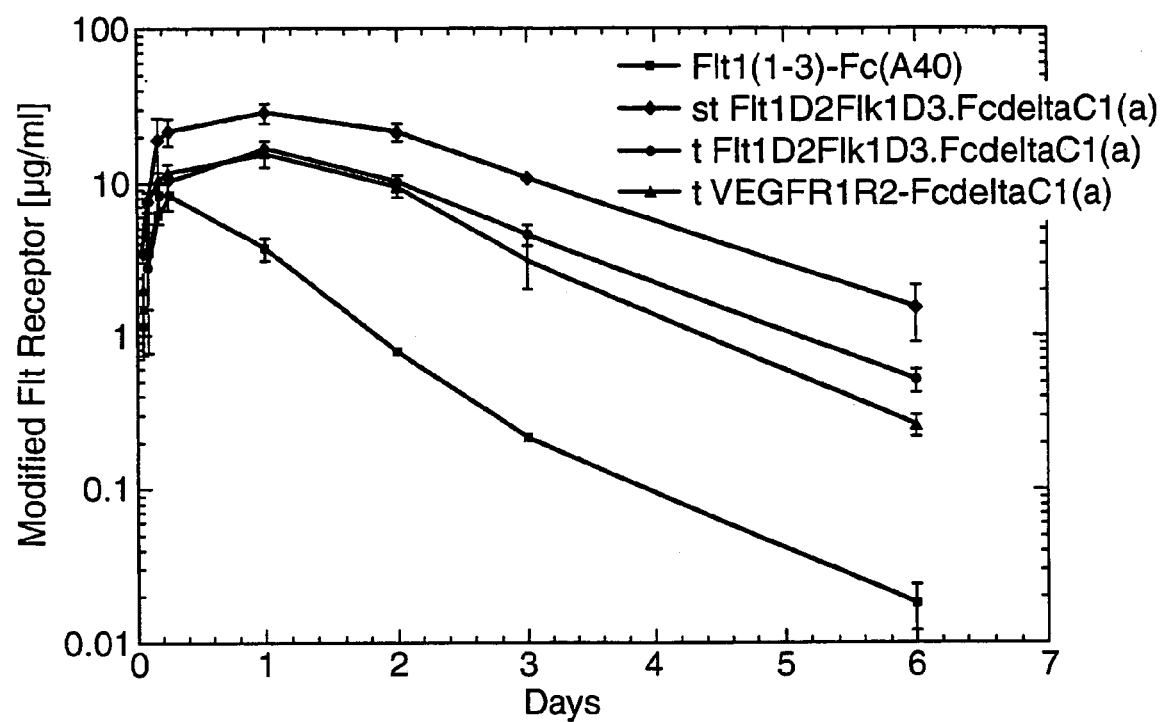
FIG. 8. Pharmacokinetics of Flt1(1-3)-Fc (A40), Flt1D2. Flk1D3. FcΔC1(a) and VEGFR1R2-FcΔC1(a).

Pharmacokinetic analysis of Flt1(1-3)-Fc (A40). Flt1D2. Flk1D3. FcΔC1(a) and VEGFR1R2-FcΔC1(a). Balb/c mice (25-30 g) were injected subcutaneously with 4 mg/kg of Flt1(1-3)-Fc (A40), CHO transiently expressed Flt1D2. Flk1D3. FcΔC1(a), CHO stably expressed Flt1D2. Flk1D3. FcΔC1(a), and CHO transiently expressed VEGFR1R2-FcΔC1(a). The mice were tail bled at 1, 2, 4, 6, 24 hrs, 2 days, 3 days and 6 days after injection. The sera were assayed in an ELISA designed to detect Flt1(1-3)-Fc (A40), Flt1D2. Flk1D3. FcΔC1(a) or VEGFR1R2-FcΔC1(a). The ELISA involves coating an ELISA plate with VEGF165, binding the detect Flt1(1-3)-Fc (A40), Flt1D2. Flk1D3. FcΔC1(a) or VEGFR1R2-FcΔC1(a) and reporting with an anti-Fc antibody linked to horse radish peroxidase. The results of this experiments are shown in FIG. 8. The $T_{max}$ for Flt1(1-3)-Fc (A40) was at 6 hrs while the $T_{max}$ for the transient and stable Flt1D2. Flk1D3. FcΔC1(a) and the transient VEGFR1R2-FcΔC1(a) was 24 hrs. The $C_{max}$ for Flt1(1-3)-Fc (A40) was 8 µg/ml. For both transients (Flt1D2. Flk1D3FcΔC1(a) and VEGFR1R2-FcΔC1(a)) the $C_{max}$ was 18 µg/ml and the $C_{max}$ for the stable VEGFR1R2-FcΔC1(a) was 30 µg/ml.

Figure 9:
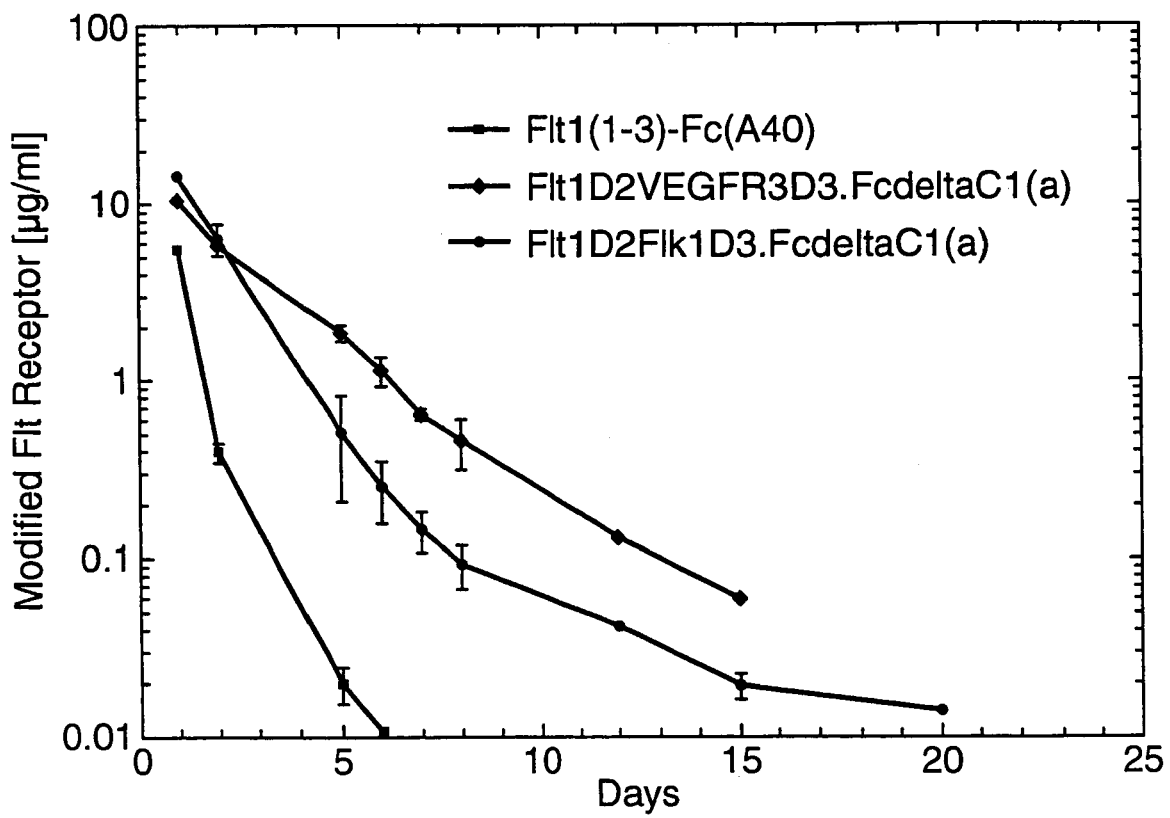
FIG. 9. Pharmacokinetics of Flt1(1-3)-Fc (A40), Flt1D2. Flk1D3. FcΔC1(a) and Flt1D2. VEGFR3D3. FcΔC1(a).

Pharmacokinetic analysis of Flt1(1-3)-Fc (A40). Flt1D2. Flk1D3. FcΔC1(a) and Flt1D2. VEGFR3D3. FcΔC1(a). Balb/c mice (25-30 g) were injected subcutaneously with 4 mg/kg of Flt1(1-3)-Fc (A40), CHO transiently expressed Flt1D2Flk1D3FcΔC1(a) and CHO transiently expressed Flt1D2. VEGFR3D3. FcΔC1(a). The mice were tail bled at 1, 2, 5, 6, 7, 8, 12, 15 and 20 days after injection. The sera were assayed in an ELISA designed to detect Flt1(1-3)-Fc, Flt1D2. Flk1D3. FcΔC1(a) and Flt1D2. VEGFR3D3. FcΔC1(a). The ELISA involves coating an ELISA plate with 165, binding the Flt1(1-3)-Fc, Flt1D2. Flk1D3. FcΔC1(a) or Flt1D2. VEGFR3D3. FcΔC1(a) and reporting with an anti-Fc antibody linked to horse radish peroxidase. Flt1(1-3)-Fc (A40) could no longer be detected in the serum after day 5 whereas, Flt1D2. Flk1D3. FcΔC1(a) and Flt1D2VEGFR3D3FcΔC1(a) were detectable for 15 days or more. The results of this experiment are shown in FIG. 9.

Example 30

Figure 10:
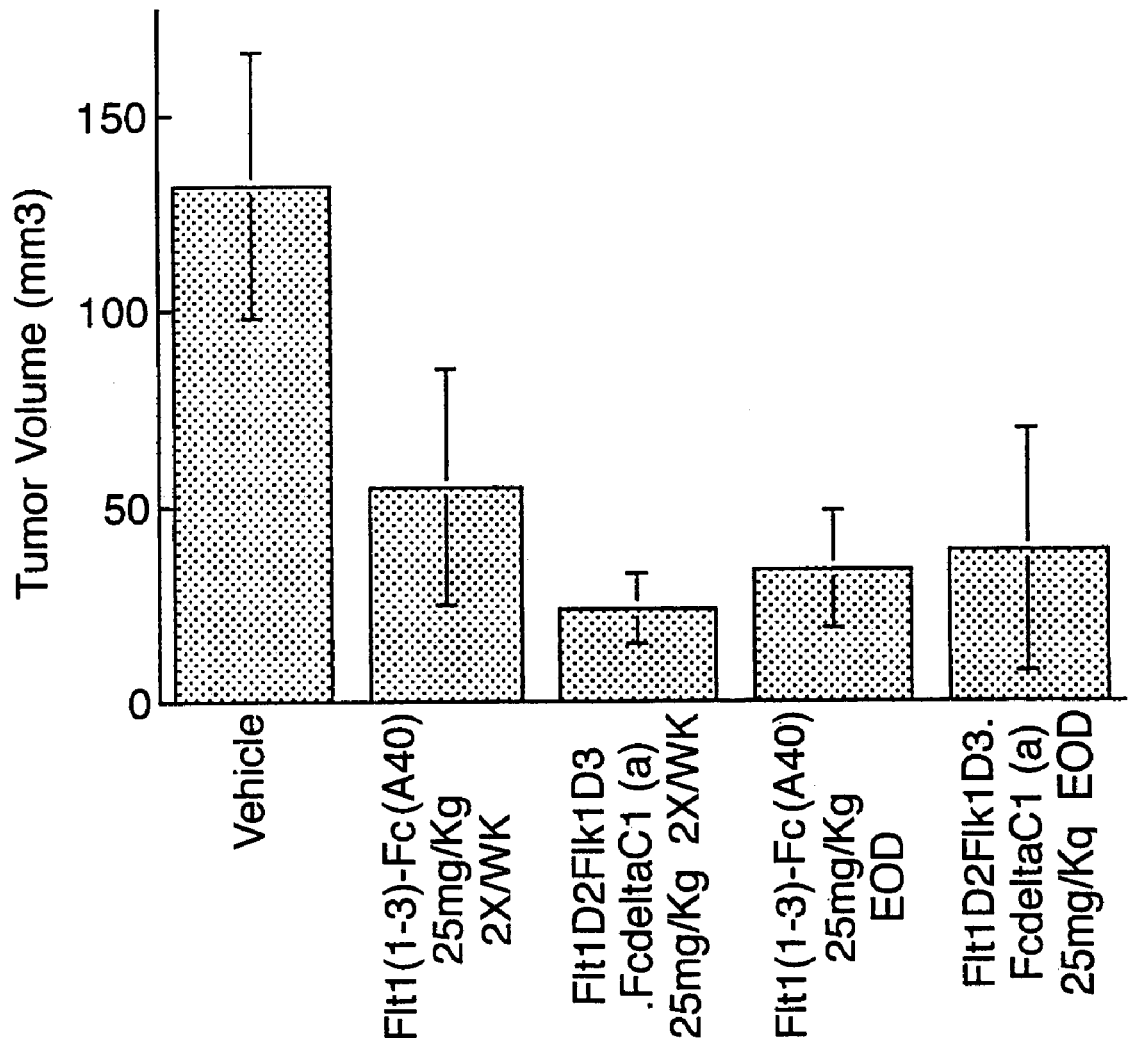
FIG. 10. The ability of Flt1D2. Flk1D3. FcΔC1(a) to inhibit HT-1080 fibrosarcoma tumor growth in vivo.
Figure 11:
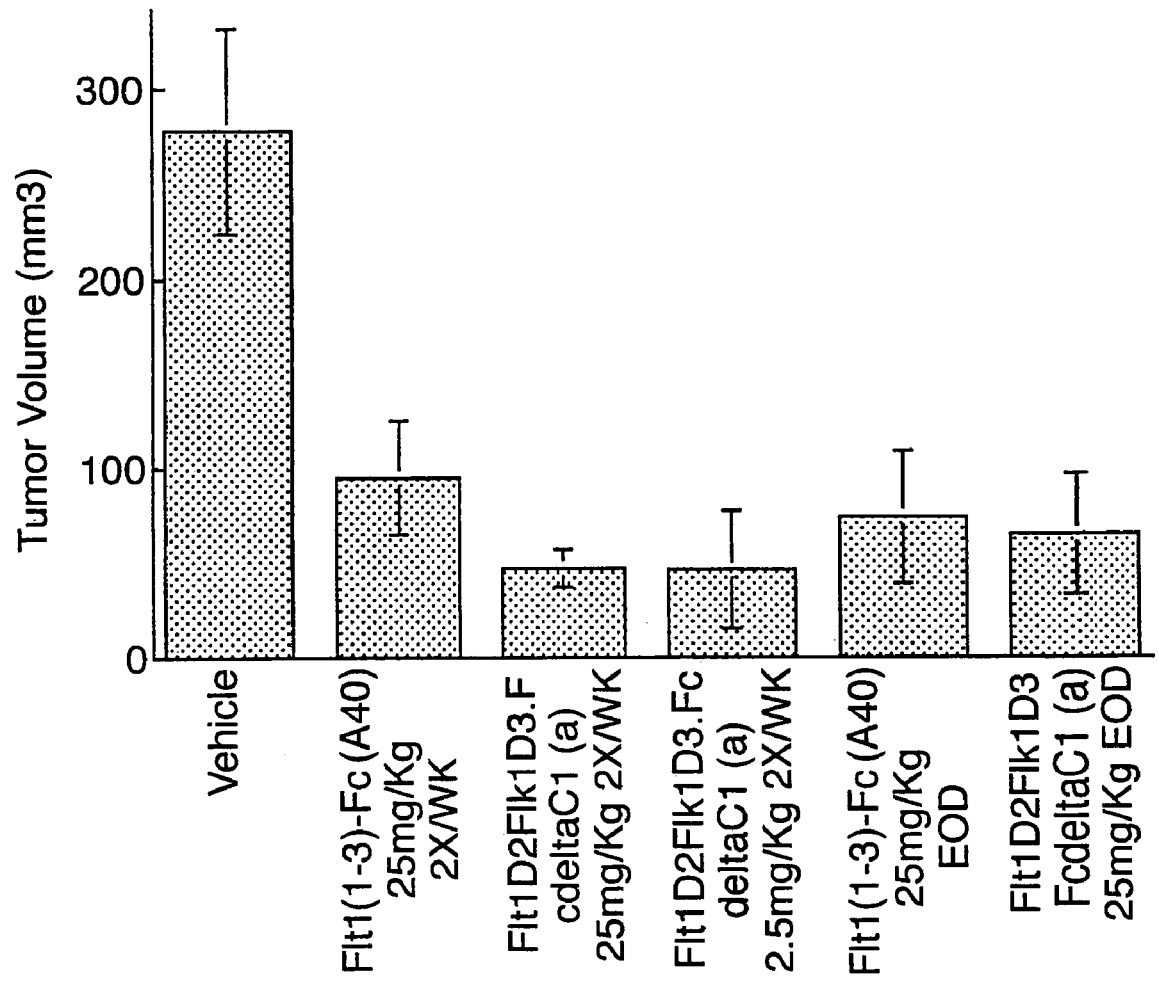
FIG. 11. The ability of Flt1D2. Flk1D3. FcΔC1(a) to inhibit C6 glioma tumor growth in vivo.

Evaluation of the Ability of Flt1D2. Flk1D3. FcΔC1(a) to Inhibit Tumor Growth In Vivo To evaluate the ability of Flt1D2. Flk1D3. FcΔC1(a) to inhibit tumor growth in vivo a model in which tumor cell suspensions are implanted subcutaneously on the right flank of male severe combined immunodeficiency (SCID) mice was employed. Two cell lines, the human HT-1080 fibrosarcoma cell line (ATCC accession no. CCL-121) and the rat C6 glioma cell line (ATCC accession no. CCL-107), each of which exhibit distinctly different morphologies and growth characteristics, were used in the assay. The first dose of Flt1D2. Flk1D3. FcΔC1(a) (at 25 mg/Kg or as indicated in FIG. 10-11) was given on the day of tumor implantation. Animals subsequently received subcutaneous injections of Flt1(1-3)-Fc (A40), Flt1D2. Flk1D3. FcΔC1(a) or vehicle either every other day (EOD) or two times per week (2×/wk) for a period of 2 weeks. After 2 weeks, animals were perfused with fixative, tumors were removed and samples were blinded. Tumor volume was determined by measuring the length and width of visible subcutaneous tumors. Both of Flt1(1-3)-Fc (A40) and Flt1D2. Flk1D3. FcΔC1(a) significantly reduced the growth of tumors formed by HT-1080 and C6 cells.

Example 31

The Effect of VEGF165 and Modified Flt Receptors in Female Reproductive System

The stereotypic pattern of vascular remodeling which occur in the uterus and ovary over the course of the reproductive cycle has been well characterized, making these tissues particularly well suited to the study of mechanisms which regulate angiogenesis, vascular remodeling and vascular regression. Indeed, in situ hybridization studies in the reproductive tissues provided the first clear evidence that VEGF acts as a mediator of physiological angiogenesis in mature rodents, as well as humans and non-human primates. As cyclic angiogenesis and vascular remodeling are prominent features of the normal ovary and uterus, it is not surprising that abnormal blood vessel growth and/or vascular dysfunction have been found to characterize many pathological conditions which affect these organs. Furthermore, these pathogenic vascular abnormalities are thought to be caused or perpetuated by the dysregulated expression of one or more angiogenic or anti-angiogenic factors, most prominently VEGF.

For example, abnormal angiogenesis is characteristic of polycystic ovary disease, endometriosis and endometrial carcinoma, and in each case VEGF is over expressed in the affected tissue. Overexpression of VEGF is also thought to play a pathogenic role in the establishment of systemic vascular hyperpermeability in ovarian hyperstimulation syndrome and preeclampsia. In addition, VEGF has been implicated as the permeability factor responsible for the production of ascites associated with ovarian carcinoma and other tumors. Agents which effectively neutralize the biological actions of VEGF can reasonably be anticipated to be of therapeutic benefit in the above and related conditions.

Angiogenesis and vascular remodeling are also hallmarks of blastocyst implantation and placental development. VEGF is strongly expressed both in the maternal decidua and in embryonic trophoblasts, where it is thought to first stimulate expansion and hyperpermeability of the uterine vasculature during the peri-implantation period and subsequently mediate formation of both the maternal and embryonic components of the placental vasculature. VEGF is also required for luteal angiogenesis and associated progesterone secretion necessary to prepare the uterus for implantation. Thus, agents which inhibit the biological actions of VEGF may prove to be useful as contraceptive agents (by preventing implantation), or as an abortifacients in the early stages of gestation. The latter application might find particular use as a non-surgical intervention for the termination of ectopic pregnancies.

While the expression of VEGF receptors is largely confined to the vascular endothelium in normal reproductive tissues, Flt1 is also expressed by trophoblasts in the placenta in both humans and animals where it has been proposed to play a role in trophoblast invasion. Interestingly, both Flt1 and KDR (Flk1) are expressed by choriocarcinoma cell line BeWo, and VEGF has been shown to promote DNA synthesis and tyrosine phosphorylation of MAP kinase in these cells. Furthermore, primary and metastatic ovarian carcinomas not only to express high levels of VEGF, but—in addition to the vascular endothelium—the tumor cells themselves express KDR and/or Flt1. These findings suggest that VEGF may not only be critically involved in the generation and maintenance of tumor vasculature, but that at least in some tumors of reproductive origin VEGF may subserve an autocrine role, directly supporting the survival and proliferation of the tumor cells. Thus agents which block the actions of VEGF may have particularly beneficial applications to the treatment of tumors of reproductive origin.

Figure 12:
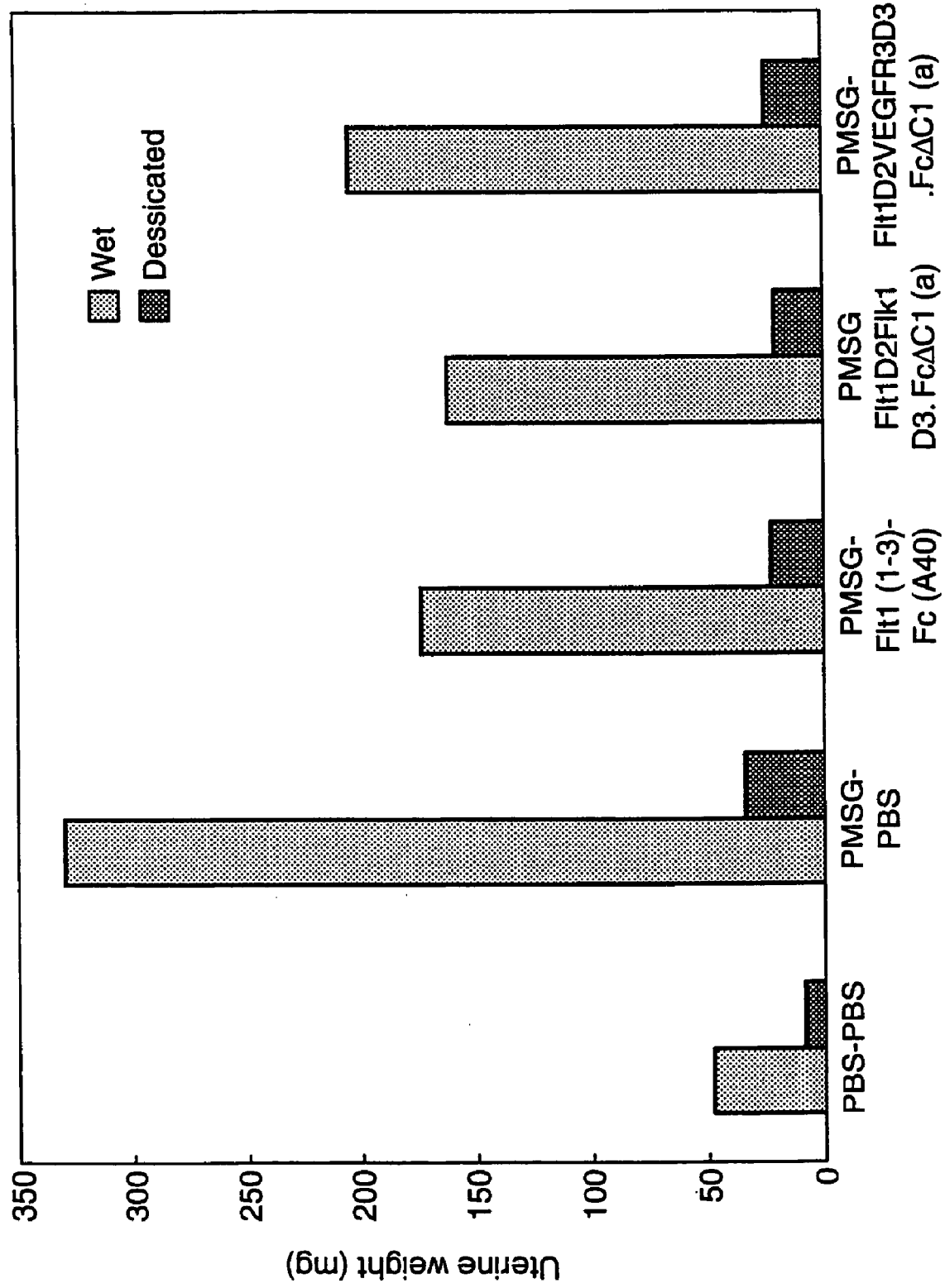
FIG. 12. VEGF-induced uterine hyperpermeability.

Assessment of VEGF-Induced Uterine Hyperpermeability. Pregnant mare's serum gonadotrophin (PMSG) was injected subcutaneously (5 IU) to induce ovulation in prepubertal female rats. This results in a surge of estradiol after 2 days which in turn causes an induction of VEGF in the uterus. It is reported that this induction results in hyperpermeability of the uterus and an increase in uterine wet weight 6 hrs. later and, therefore, could potentially be blocked by the modified Flt receptors Flt1(1-3)-Fc (A40), Flt1D2. Flk1D3FcΔC1(a) and Flt1D2VEGFR3D3FcΔC1(a). In this in vivo model, the normal weight of the rat uterus is about 50 mg and this can be induced to 300-350 mg by PMSG. Desiccation of the tissue reveals that this is all water weight. Subcutaneous injection of Flt1(1-3)-Fc (A40), Flt1D2. Flk1D3. FcΔC1(a) and Flt1D2. VEGFR3D3. Fc1C1(a) at 25 mg/kg at 1 hr. after PMSG injection results in about a 50% inhibition of the increase in uterine wet weight. Increasing the dose of modified Flt receptor does not further reduce the increase in wet weight suggesting that there is a VEGF-independent component to this model (FIG. 12).

Figure 13A:
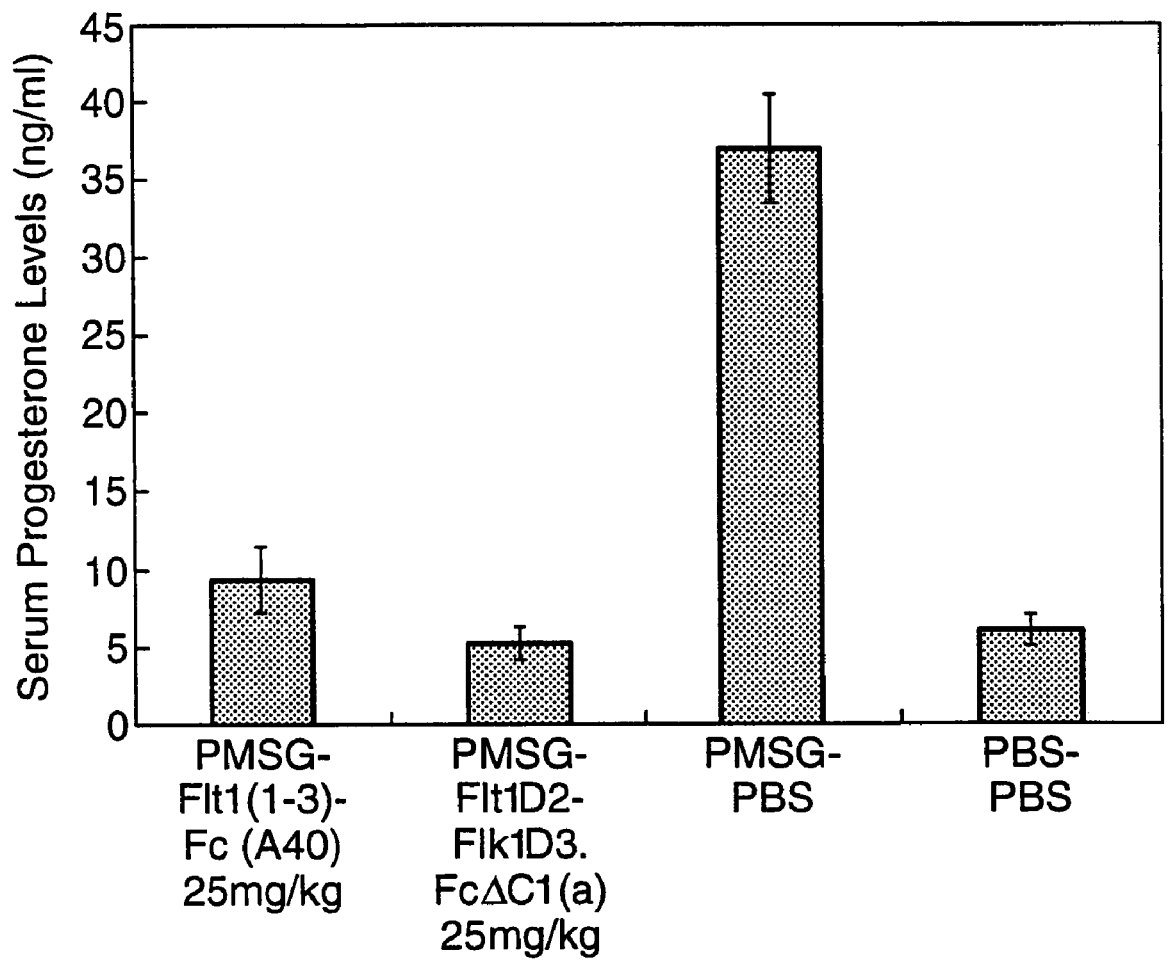
FIGS. 13A-B. Assessment of corpus luteum angiogenesis using progesterone as a readout.
Figure 13B:
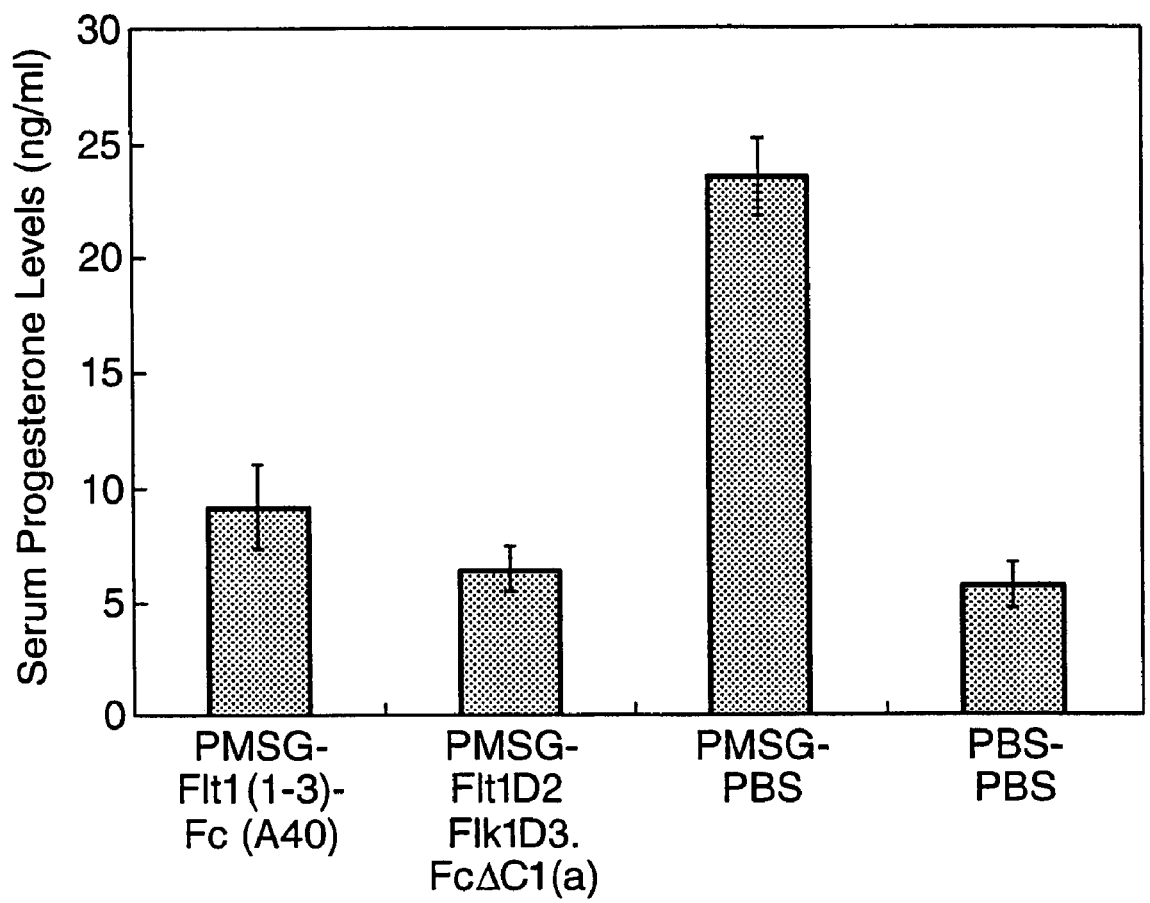
Figure 14:
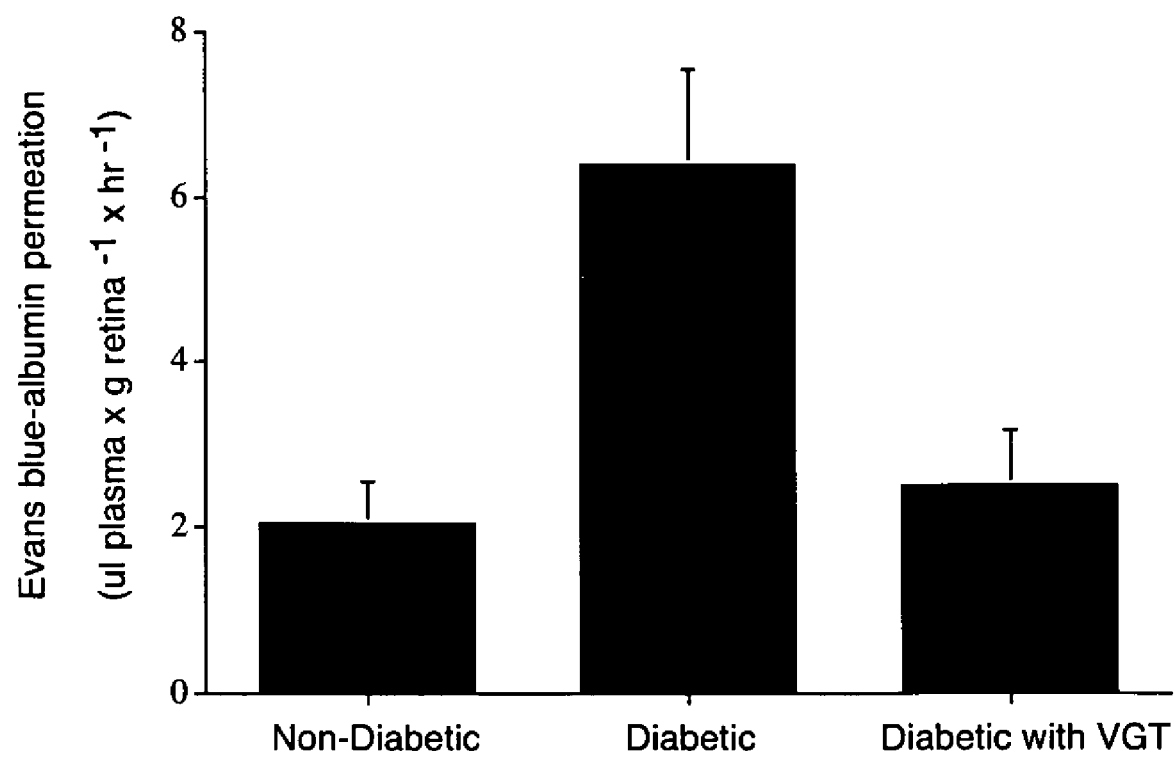
FIG. 14. VEGFR1R2-FcΔC1(a) prevents Evans Blue leakage in streptozotocin-treated rats.

Assessment of corpus luteum angiogenesis using progesterone as a readout. Pregnant mare's serum gonadotrophin (PMSG) is injected subcutaneously (5 IU) to induce ovulation in prepubertal female rats. This results in a fully functioning corpus luteum containing a dense network of blood vessels after 4 days that allows for the secretion of progesterone into the blood stream in order to prepare the uterus for implantation. The induction of angiogenesis in the corpus luteum requires VEGF; therefore, blocking VEGF would result in a lack of new blood vessels and thus a lack of progesterone secreted into the blood stream. In this in vivo model, resting levels of progesterone are about 5 ng/ml and this can be induced to a level of 25-40 ng/ml after PMSG. Subcutaneous injection of Flt1(1-3)-Fc (A40) or Flt1D2. Flk1D3. FcΔC1(a) at 25 mg/kg or 5 mg/kg at 1 hr. after PMSG injection results in a complete inhibition of the progesterone induction on day 4 (FIGS. 13A-B).

Example 33

Pharmacokinetic Analysis of Flt1(1-3)-Fc (A40) and Pegylated Flt1(1-3)-Fc

Flt1(1-3)-Fc was PEGylated with either 10 kD PEG or 20 kD PEG and tested in balb/c mice for their pharmacokinetic profile. Both PEGylated forms of Flt1(1-3)-Fc were found to have much better PK profiles than Flt1(1-3)-Fc (A40), with the Tmax occurring at 24 hrs. for the PEGylated molecules as opposed to 6 hrs. for Flt1(1-3)-Fc (A40).

Example 34

VEGF165 ELISA to Test Affinity of Modified Flt1 Receptor Variants 10 pM of VEGF165 was incubated overnight at room temperature with modified Flt1 receptor variants ranging from 160 pM to 0.1 pM. The modified Flt1 receptor variants used in this experiment were Flt1(1-3)-Fc, Flt1(1-3)-Fc (A40), transiently expressed Flt1D2Flk1D3FcΔC1(a), transiently expressed Flt1D2VEGFR3D3-FcΔC1(a), Flt1-(1-3$_{NAS}$)-Fc, Flt1(1-3$_{R->C}$)-Fc and Tie2-Fc. Flt1(1-3$_{NAS}$)-Fc is a modified version of Flt1(1-3)-Fc in which the highly basic amino acid sequence KNKRASVRRR (SEQ ID NO:32) is replaced by NASVNGSR (SEQ ID NO:33), resulting in the incorporation of two new glycosylation sites and a net reduction of five positive charges, both with the purpose of reducing the unfavorable effects of this sequence on PK. Flt1(1-3$_{R->C}$)-Fc is a modification in which a single arginine (R) residue within the same basic amino acid sequence is changed to a cysteine (C) (KNK<u>R</u>ASVRRR (SEQ ID NO:32)→KNK<u>C</u>ASVRRR (SEQ ID NO:34)) to allow for pegylation at that residue, which could then shield the basic region from exerting its unfavorable effects on PK. After incubation the solution was transferred to a plate containing a capture antibody for VEGF165 (R&D). The amount of free VEGF165 was then determined using an antibody to report free VEGF165. This showed that the modified Flt1 receptor variant with the highest affinity for VEGF165 (determined as the lowest amount of free VEGF165) was Flt1D2Flk1D3. FcΔC1(a), followed by Flt1(1-3)-Fc and Flt1(1-3)-Fc (A40) and then by Flt1(1-3$_{R->C}$)-Fc, Flt1(1-3$_{NAS}$)-Fc and Flt1D2VEGFR3D3-FcΔC1(a). Tie2Fc has no affinity for VEGF165.

Example 35

Breakdown of Blood-retinal Barrier in Diabetes is Reversed by Inhibition of VEGF Rats received a single injection of VEGFR1R2-FcΔC1(a) (SEQ ID NO:16) (25 mg/kg, i.p.) or PBS 4 weeks after induction of diabetes by streptozotocin (65 mg/kg, i.v.). The permeability of retinal vessels was assessed 24 hours later by measuring the extravasation of Evans Blue dye, which binds to albumin in the circulation. Under deep anesthesia, Evans Blue dye (45 mg/kg) was injected intravenously, and allowed to circulate for 60 minutes, and blood samples were taken periodically to assess the concentration of dye in the circulation. The animals were then perfused to flush dye and blood from the vasculature, the eye enucleated and the retinas removed. Evans blue was extracted, and the concentration of dye in the retina was normalized to retinal weight and the time-averaged concentration of Evans blue in the circulation (mL plasma×g retina weight$^{-1}$×hr$^{-1}$) to provide an index of vascular leak. VEGFR1R2-FcΔC1(a) normalized retinal vascular permeability to levels evident in non-diabetic rats.

Example 36

VEGFR1R2-FcΔC1(a) Prevents Neovascularization Induced by Retinal Ischemia

Excessive upregulation of VEGF expression is responsible for pathologic neovascularization in many retinal diseases. The anti-angiogenic properties of VEGFR1R2-FcΔC1 (a) were investigated in a mouse model of oxygen-induced ischemic retinopathy (OIR). OIR was produced by transiently exposing mouse pups to increased ambient oxygen (hyperoxia), resulting in obliteration of the developing microvasculature within the central retina. Subsequent return of the animals to room air results in relatively hypoxic conditions in the retina, which in turn stimulates an angiogenic response that shares features with both diabetic retinopathy, retinopathy of prematurity and other ischemic retinopathies. VEGFR1R2-FcΔC1(a) (25 mg/kg, ip) was administered every other day beginning 12-24 hours after returning the mice from hyperoxia to room air. Littermate controls received injections of human Fc following the same schedule. Retinas were collected 1 week following return to room air. Flat mounts were prepared from one retina obtained from each animal, and the retinal vessels stained with fluoresceinated lectin (*griffonia simplicifolia*). The other retina was embedded and cross-sections were cut and stained with hematoxylin and eosin.

Figure 15:
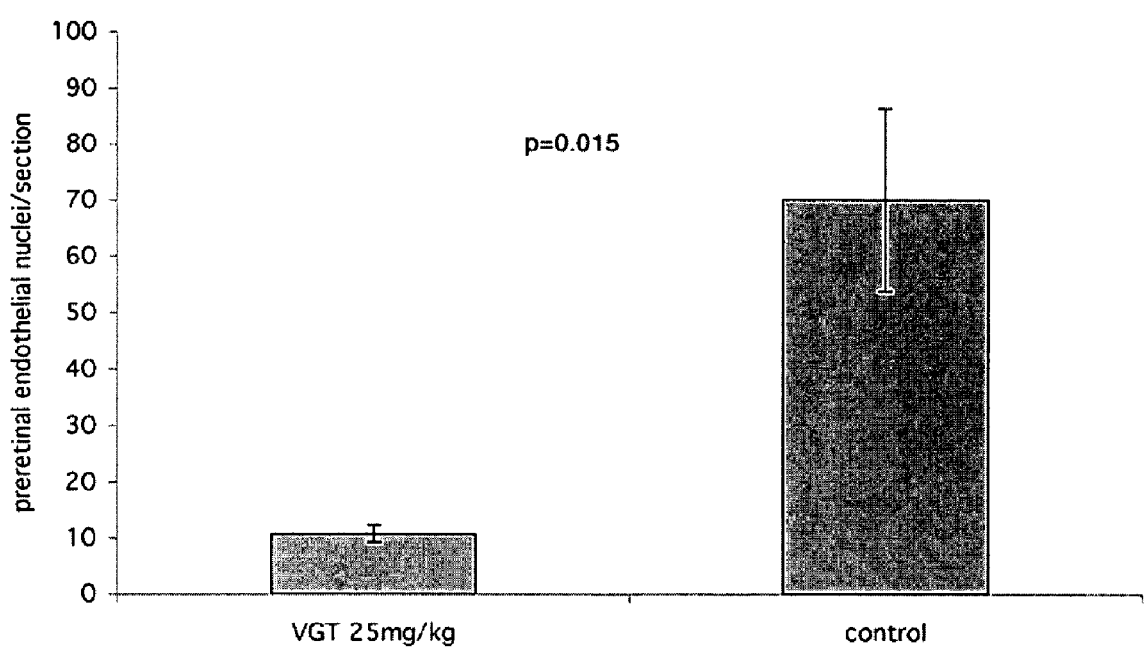
FIG. 15. VEGFR1R2-FcΔC1(a) prevents neovascularization induced by retinal ischemia. Serial 10 μm cross sections were collected and stained with hematoxylin and eosin. For each animal, nuclei in preretinal neovessels were counted in a series of ten sections within 300 microns of the optic nerve head and averaged. Counts were obtained in three independent experiments, n≧4 for each treatment group in each study.

Retinas of all control mice exposed to hyperoxia exhibited marked pathologic angiogenesis, characterized by the presence of vascular tufts penetrating the inner limiting membrane and chaotic sprouting of vessels on the surface of the retina, particularly around the optic nerve head. Administration of VEGFR1R2-FcΔC1(a) almost completely blocked the development of these vascular abnormalities as quantitated by counting endothelial cell nuclei in the abnormal pre-retinal vessels (FIG. 15). Although pathologic angiogenesis was dramatically inhibited, systemic administration of VEGFR1R2-FcΔC1(a) did not block the growth of normal-appearing intraretinal vessels in these animals.

Example 37

Figure 16:
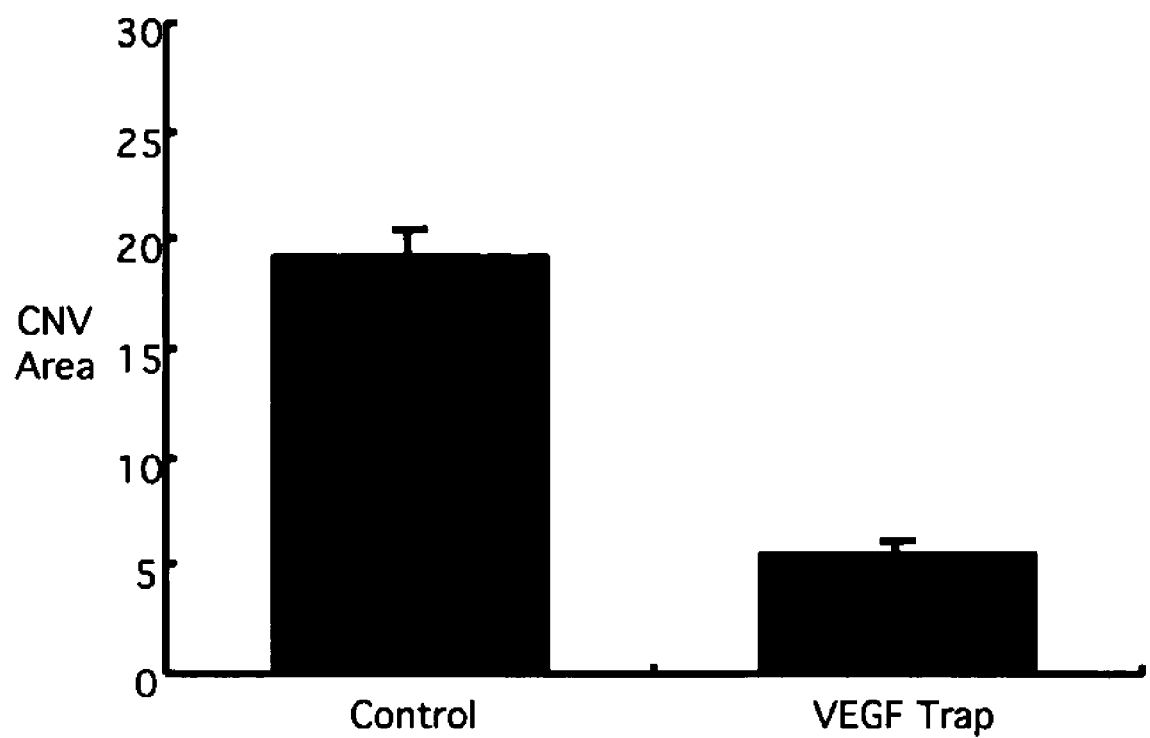
FIG. 16. Effect of subcutaneous VEGFR1R2-FcΔC1(a) injections on choroidal neovascularization area. The size of CNV lesions was measured in choroidal flat mounts. The images were digitized using an Axioskop microscope equipped with a video camera, and the total area of choroidal neovascularization associated with each laser burn was measured using Image-Pro Plus software.

Subcutaneous Administration of VEGFR1R2-FcΔC1(a) Suppresses Choroidal Neovascularization Though animals do not develop age related macular degeneration (AMD) per se, choroidal neovascularization resembling that seen in AMD can be produced by using a laser to produce focal disruptions in Bruch's membrane and the overlying retinal pigment epithelium (RPE). This injury stimulates the abnormal growth of underlying choroidal capillaries into the rpe layer and subretinal space. Disruption of Bruch's membrane is common to all forms of choroidal neovascularization (CNV), including that which characterizes the wet form of AMD. In the laser-induced model of choroidal neovascularization, groups of 9 or 10 mice were treated with sc injections of 25 mg/kg of VEGFR1R2-FcΔC1(a) or human Fc one day prior to laser injury and on days 2, 5, 8, and 11 after laser. At 14 days after laser injury, the mice were injected intravenously with fluorescein-labeled dextran (50 mg), euthanized, and eyes were rapidly dissected for choroidal flat mounts or frozen in optimum cutting temperature embedding compound and sectioned for evaluation of the lesions. VEGFR1R2-FcΔC1(a) administration reduced the area of CNV lesions by approximately 70% (FIG. 16).

Figure 20:
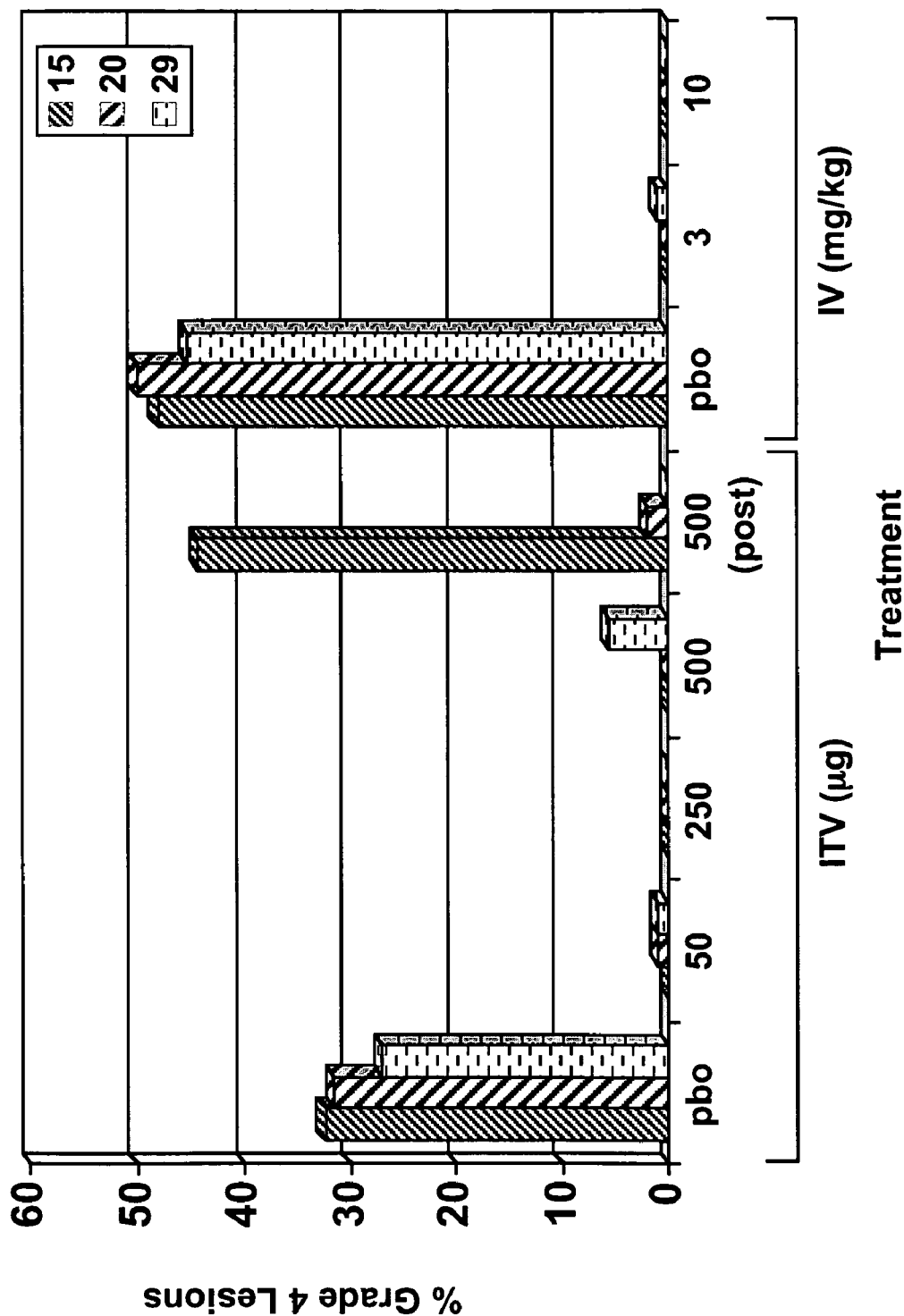
FIG. 20. System or intravitreal VEGF trap administration prevents laser-induced choroidal neovascularization (CNV) and reverses vascular leak in established lesions.

The effect of VEGFR1R2-FcΔC1(a) on laser-induced choroidal neovascularization also was evaluated in adult cynomolgus monkeys. In this experiment, VEGFR1R2-FcΔC1(a) was administered by intravenous or intravitreal injection. Each animal received nine or ten laser burns to each retina, and the development of active choroidal neovascular lesions was assessed by fluorescein angiography, once before the initiation of treatment and 15, 20 and 19 days postlaser. VEGFR1R2-FcΔC1(a) was administered intravenously once per week, beginning one week before laser injury, at a dose of 3 mg/kg or 10 mg/kg. Intravitreal injections were made once every two weeks, at a dose of 50, 250 or 500 mcg/eye beginning one week before laser, or once, two weeks following laser (500 mcg dose only), at which time active CNV lesions had already formed. Control animals received weekly intravenous or biweekly intravitreal injections of placebo, beginning one week before laser. Each of the above experimental and control groups comprised six animals, 3 males and 3 females. CNV lesions were visualized by fluorescein angiography and graded. Active CNV lesions characterized bright hyperflourescence, with late leakage beyond the borders of the laser spot (Grade 4), developed at 32% and 48% of the laser burn sites, in animals receiving intravitreal or intravenous administration of placebo. In contrast, the development of grade 4 lesions was completely or nearly completely prevented in all groups of animals receiving intravenous or intravitreal injections of VEGFR1R2-FcΔC1(a) (FIG. 20). Moreover a single intravitreal injection (500 mcg) of VEGFR1R2-FcΔC1(a) made following the laser injury reduced the incidence of grade 4 lesions from 44% to 0% within 10 days of treatment (FIG. 20).

Example 38

Figure 17:
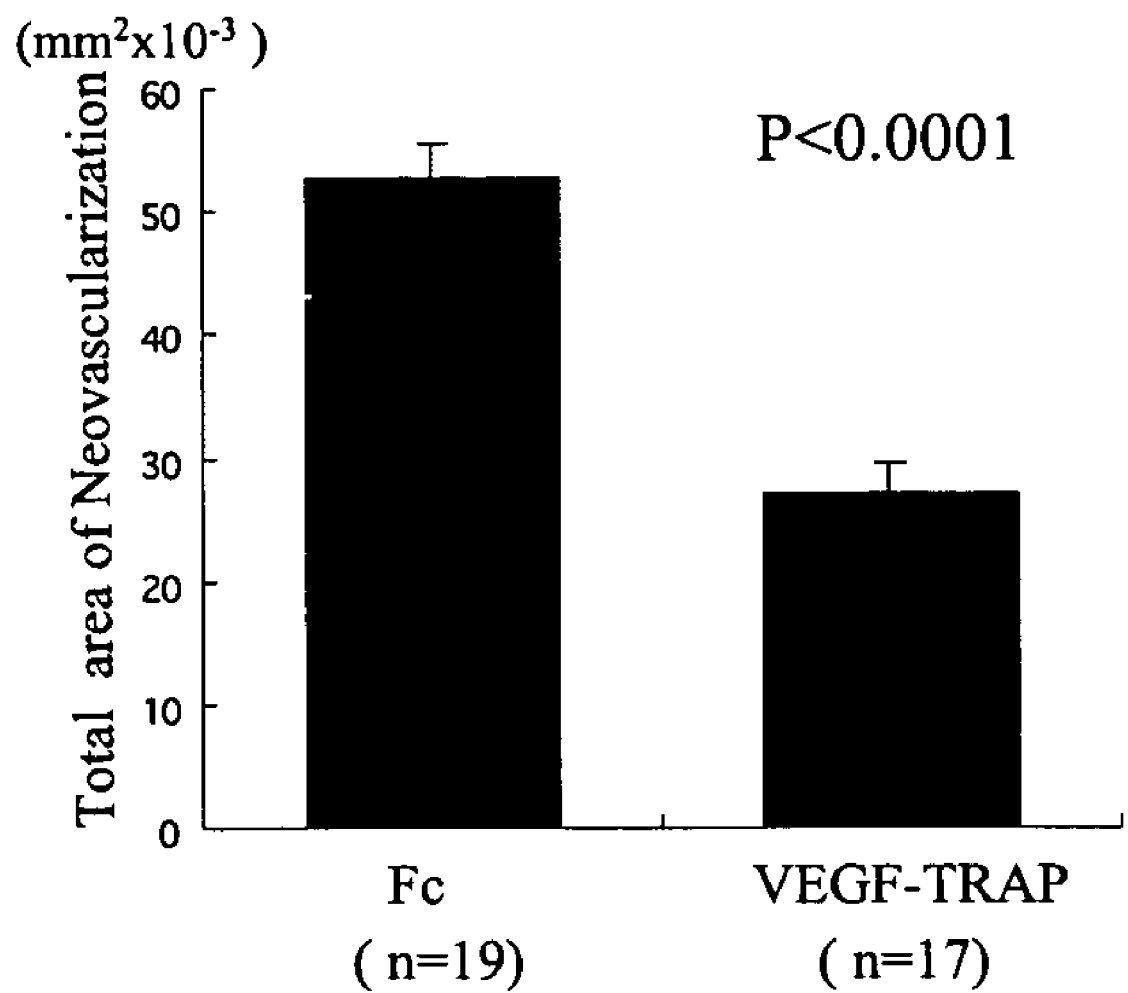
FIG. 17. VEGFR1R2-FcΔC1(a) inhibits subretinal neovascularization in Rho/VEGF transgenic mice.

Subcutaneous Administration of VEGFR1R2-FcΔC1(a) Inhibits Subretinal Neovascularization in Rho/VEGF Transgenic Mice Transgenic mice expressing a recombinant human VEGF transgene under the control of the rhodopsin promoter (Rho/VEGF) were used in these experiments. These animals begin to express VEGF in photoreceptors on about postnatal day (P) 7, which typically results in pronounced subretinal neovascularization by P21. At P7, mice were divided into 2 groups and treated with 25 mg/kg of VEGFR1R2-FcΔC1(a) (9 mice, 17 eyes) or human Fc (10 mice, 19 eyes) on P7, P10, P13, P16, and P19. On P21, the mice were anesthetized and perfused with fluorescein-labeled dextran. Retinal whole mounts from mice treated with VEGFR1R2-FcΔC1(a) showed few areas of neovascularization while many new vessels were present in the subretinal space of mice that had been treated with Fc. Measurement of the total area of neovascularization per retina by image analysis showed significantly less neovascularization in VEGFR1R2-FcΔC1(a)-treated mice, compared to those treated with Fc (FIG. 17).

Example 39

Figure 18A:
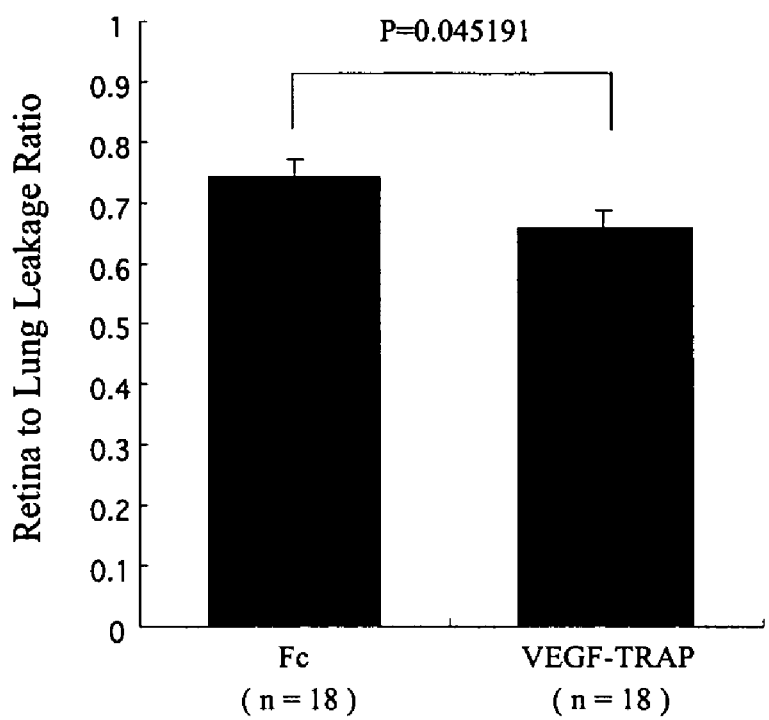
FIGS. 18A-B. VEGF-Induced breakdown of the blood retinal barrier. A. Following intravitreal injections of VEGF, adult mice (C57BL/6) treated with injections of VEGFR1R2-FcΔC1(a) had a significantly smaller retina to lung leakage ration than mice treated with Fc fragment, indicating less breakdown of BRB. B. Double transgenic mice treated with injections of VEGFR1R2-FcΔC1(a) had a significant reduction in the retina to lung leakage ration compared to mice treated with Fc fragment.

Subcutaneous Injections of VEGFR1R2-FcΔC1(a) Suppress VEGF-Induced Breakdown of the Blood-retinal Barrier Adult C57BL/6 mice were given a sc injection of 25 mg/kg of VEGFR1R2-FcΔC1(a) or Fc fragment and on the following day received an intravitreous injection of 1 µl of $10^{-6}$M VEGF. Six hours later, retinal vascular permeability was measured using [$^3$H]-mannitol as a tracer. Mice treated with VEGFR1R2-FcΔC1(a) (9 mice, 18 eyes) had a significantly smaller retina to lung leakage ratio (the ratio of radioactivity in the retina compared to excised lung) than mice treated with Fc fragment (9 mice, 18 eyes) indicating less breakdown of the blood retinal barrier (FIG. 18A).

Figure 18B:
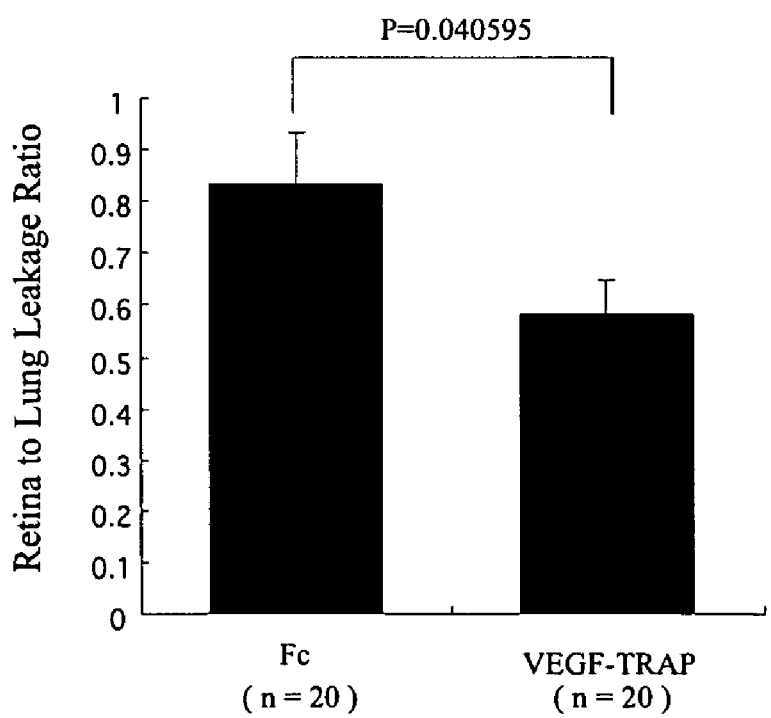

The effect of VEGFR1R2-FcΔC1(a) on VEGF-mediated vascular leak was also evaluated in a second experiment, which employed double transgenic mice (rtTA/rho-TRE/VEGF). These mice are characterized by photoreceptor-specific expression of the VEGF transgene that is inducible by administration of doxycycline. Adult rtTA/rho-TRE/VEGF mice were injected sc with 25 mg/kg VEGFR1R2-FcΔC1(a) (10 mice, 20 eyes) or Fc fragment (10 mice, 20 eyes). On the following day, doxycycline (2 mg/mL) was placed in their drinking water to stimulate over-expression of VEGF within the retina. Two days later, they were given a second sc injection of VEGFR1R2-FcΔC1(a) or Fc fragment and then the next day retinal vascular permeability was measured with [$^3$H]-mannitol. Mice treated with VEGFR1R2-FcΔC1(a) exhibited a significant reduction in the retina to lung leakage ratio compared to mice treated with Fc (FIG. 18B), indicating that impairment in the blood-retinal barrier was ameliorated.

Example 40

VEGFR1R2-FcΔC1(a) Inhibits Injury-induced Corneal Neovascularization, Edema, and Inflammation Corneal neovascularization was induced in male C57Bl/6 mice by intrastromal placement of 3 nylon sutures, or by chemical injury (NaOH) and mechanical debridement of the corneal epithelium. Multiple experiments were conducted in which VEGFR1R2-FcΔC1(a) was administered intraperitoneally once or at multiple time points immediately before or following injury. The growth of corneal neovessels was evaluated by slit-lamp microscopy and histological evaluation. The vasculature was labeled with an endothelial cell specific fluorescein-conjugated lectin, and neovascularization was evaluated in corneal flat-mounts, as well as in cross sections using PECAM immunohistochemistry. The presence of corneal edema was evaluated, using slit lamp microscopy, and corneal thickness was measured in cross-sections; increases in corneal thickness reflect the amount of edema. The numbers of polymorphonuclear leukocytes (PMN) and macrophages were determined by staining cross-sections with HEMA-3 or rat anti-mouse F4/80 monoclonal antibody, respectively.

Figure 19:
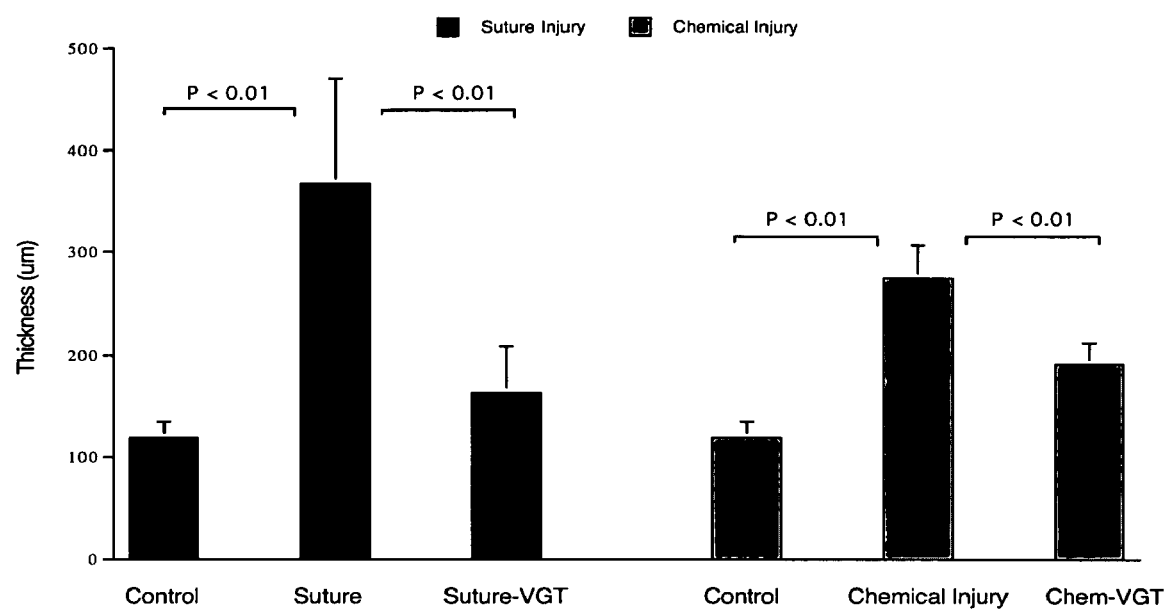
FIG. 19. Effect of VEGFR1R2-FcΔC1(a) administration on corneal thickness in suture and alkali burn models of corneal trauma. Corneas were injured by suture placement or application of NaOH as described, and a single dose of VEGFR1R2-FcΔC1(a) (25 mg/kg, ip) or saline (n=5 per group) was administered immediately following injury. The contralateral cornea served as normal, undamaged controls. Corneas were collected 7 days later and cross-sections were cut and stained with hematoxylin and eosin. Corneal thickness was measured as an index of corneal edema.

Dosing regimens which employed multiple injections of VEGFR1R2-FcΔC1(a) (25 mg/kg, ip) completely inhibited corneal neovascularization in both the suture and chemical injury models. Moreover, single injections of 25 or 12.5 mg/kg VEGFR1R2-FcΔC1(a) given immediately after suture injury effectively blocked corneal neovascularization for at least 9 days, while injections of 6.25 and 2.5 mg/kg ameliorated but did not block corneal neovascularization. The lowest dose of VEGFR1R2-FcΔC1(a) tested (0.5 mg/kg) had no evident effect. Corneal thickness, reflecting the amount of edema present, was significantly reduced in VEGFR1R2-FcΔC1(a)-treated animals compared to vehicle-treated controls (FIG. 19). Histological analyses showed that the infiltration of neutrophils and macrophages into the damaged cornea also was dramatically reduced by VEGFR1R2-FcΔC1(a) treatment.

Example 41

Transient Treatment with VEGFR1R2-FcΔC1(a) Produces Long-lasting Inhibition of Corneal Neovascularization and Conjunctivalization Following Alkali Burn Injury Corneas were injured by application of NaOH and mechanical debridement of the corneal epithelium in adult, male C57Bl/6 mice. VEGFR1R2-FcΔC1(a) or a control protein (human Fc) was administered subcutaneously (12.5 mg/kg) on days 0 (the day of injury), 7 and 14, at which time re-epithelialization of the cornea was complete. The animals were euthanized on days 28 or 42 (14 or 28 days following the last injection of VEGFR1R2-FcΔC1(a) and corneas taken for histological evaluation. Tissues were processed as described above.

Treatment with VEGFR1R2-FcΔC1(a) inhibited corneal neovascularization during the period of active treatment (as determined by slit-lamp microscopy), as well as 2 and 4 weeks following treatment cessation. In eyes evaluated on day 28 (14 days after the last injection of VEGFR1R2-FcΔC1(a), the neovascular response to injury remained completely suppressed and conjunctivalization of the cornea was also inhibited as evidenced by a more normal appearing morphology of the re-epithelialized cornea and a substantial reduction in goblet cell number (~30% relative to controls). Corneal inflammation and edema also were reduced substantially. Evaluation of flat-mounted corneas taken at Day 42 showed that neovascularization was still largely suppressed, though limited, focal sprouting of vessels at the corneal margin was observed in some cases.

The data show that when administered at the time of injury, VEGFR1R2-FcΔC1(a) improves corneal healing by potently inhibiting the development of corneal neovascularization, inflammation, edema and conjunctivalization of the corneal epithelium. These effects persisted for several weeks following cessation of treatment, suggesting that acute inhibition of VEGF following corneal injury may have long-term benefits.

We claim:

1. A method of treating retinal neovascularization, comprising administering a fusion polypeptide capable of binding vascular endothelial growth factor (VEGF) to a patient in need thereof, wherein the fusion polypeptide comprises the amino acid sequence of SEQ ID NO:16.

2. The method of claim 1, wherein neovascularization is induced by ischemia.

3. A method of treating, ameliorating, or inhibiting choroidal neovascularization, comprising administering a fusion polypeptide capable of binding vascular endothelial growth factor (VEGF) to a patient in need thereof, wherein the fusion polypeptide comprises the amino acid sequence of SEQ ID NO:16.

4. A method of treating, ameliorating, or inhibiting vascular leak in the retina, comprising administering a fusion polypeptide capable of binding vascular endothelial growth factor (VEGF) to a patient in need thereof, wherein the fusion polypeptide comprises the amino acid sequence of SEQ ID NO:16.

5. A method of treating, ameliorating, or inhibiting retinal edema, comprising administering a fusion polypeptide capable of binding vascular endothelial growth factor (VEGF) to a patient in need thereof, wherein the fusion polypeptide comprises the amino acid sequence of SEQ ID NO:16.

* * * * *